US011142518B2

(12) United States Patent
Reader et al.

(10) Patent No.: US 11,142,518 B2
(45) Date of Patent: Oct. 12, 2021

(54) 6-PYRIMIDIN-ISOINDOLE DERIVATIVE AS ERK1/2 INHIBITOR

(71) Applicant: OTSUKA PHARMACEUTICAL CO., LTD., Tokyo (JP)

(72) Inventors: Michael Reader, Bishops Stortford (GB); Nicola Elizabeth Wilsher, Cheveley (GB); Mark Henry Saunders, Reading (GB); Paul Anthony Baguley, Didcot (GB); Colin Thomas Lindley, Stanford in the Vale (GB); Robert Craig Melling, Didcot (GB); Bozena Ewa Adamczyk, Peschiera del Garda (IT); Mirka Scarati, Bigarello (IT)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 62 days.

(21) Appl. No.: 16/604,002

(22) PCT Filed: Apr. 20, 2018

(86) PCT No.: PCT/IB2018/052745
§ 371 (c)(1),
(2) Date: Oct. 9, 2019

(87) PCT Pub. No.: WO2018/193410
PCT Pub. Date: Oct. 25, 2018

(65) Prior Publication Data
US 2021/0101889 A1 Apr. 8, 2021

(30) Foreign Application Priority Data

Apr. 20, 2017 (GB) ..................... 1706327

(51) Int. Cl.
*C07D 405/14* (2006.01)
*A61K 9/00* (2006.01)
*A61K 9/19* (2006.01)
*A61K 9/20* (2006.01)
*A61K 9/48* (2006.01)
*A61K 47/10* (2017.01)

(52) U.S. Cl.
CPC .......... *C07D 405/14* (2013.01); *A61K 9/0019* (2013.01); *A61K 9/0053* (2013.01); *A61K 9/19* (2013.01); *A61K 9/2013* (2013.01); *A61K 9/2018* (2013.01); *A61K 9/4858* (2013.01); *A61K 47/10* (2013.01); *C07B 2200/13* (2013.01)

(58) Field of Classification Search
CPC ... C07D 413/14; C07D 405/14; A61K 31/506
USPC .......................................... 544/330; 514/275
See application file for complete search history.

(56) References Cited

U.S. PATENT DOCUMENTS

| | | | |
|---|---|---|---|
| 5,958,934 A | 9/1999 | Berger et al. | |
| 10,457,669 B2* | 10/2019 | Berdini ................ | C07D 487/04 |
| 11,001,575 B1 | 5/2021 | Berdini et al. | |
| 2006/0270686 A1 | 11/2006 | Kelly et al. | |
| 2008/0280891 A1 | 11/2008 | Kelly et al. | |
| 2010/0093698 A1 | 4/2010 | Bahmanyar et al. | |
| 2010/0160303 A1 | 6/2010 | Liu et al. | |
| 2010/0249092 A1 | 9/2010 | Singh et al. | |
| 2010/0267712 A1 | 10/2010 | Heemskerk et al. | |
| 2013/0065897 A1 | 3/2013 | Spicer et al. | |
| 2013/0079306 A1 | 3/2013 | Uchida et al. | |
| 2019/0047990 A1 | 2/2019 | Berdini et al. | |

FOREIGN PATENT DOCUMENTS

| | | |
|---|---|---|
| WO | 9420085 A1 | 9/1994 |
| WO | 9501348 A2 | 1/1995 |
| WO | 9950249 A2 | 10/1999 |
| WO | 02102313 A2 | 12/2002 |
| WO | 2004099159 A1 | 11/2004 |
| WO | 2005020921 A2 | 3/2005 |
| WO | 2005113541 A1 | 12/2005 |
| WO | 2006113769 A1 | 10/2006 |
| WO | 2007070398 A1 | 6/2007 |
| WO | 2008003766 A2 | 1/2008 |
| WO | 2008008059 A1 | 1/2008 |
| WO | 2008124085 A2 | 10/2008 |
| WO | 2009017838 A2 | 2/2009 |
| WO | 2009039635 A1 | 4/2009 |
| WO | 2009092432 A1 | 7/2009 |
| WO | 2009158571 A1 | 12/2009 |
| WO | 2010020432 A2 | 2/2010 |
| WO | 2010057833 A1 | 5/2010 |
| WO | 2010131922 A2 | 11/2010 |
| WO | 2010151747 A1 | 12/2010 |
| WO | 2011008931 A2 | 1/2011 |

(Continued)

OTHER PUBLICATIONS

Bastin et. al., Organic Process Research & Development (2000), 4, 427-435.*
Search Report for Great Britain Patent Application No. GB1706327.2 dated Jan. 26, 2018.
International Search Report for PCT/IB2018/052745 dated Jul. 2, 2018.
Sivaprakasam, Prasanna et al., "Discovery of New Acylaminopyridines as GSK-3 Inhibitors by a Structure Guided In-depth Exploration of Chemical Space Around a Pyrrolopyridinone Core," Bioorg. Med, Chem. Letts, 2015, 25, 9, 1856-1863.

(Continued)

*Primary Examiner* — Jeffrey H Murray
(74) *Attorney, Agent, or Firm* — Heslin Rothenberg Farley & Mesiti P.C.

(57) ABSTRACT

This invention relates to the compound (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, and in particular to novel physical forms of the compound, a process for preparing the compound and synthetic intermediates for use in the process, and novel formulations containing the compound, as well as therapeutic uses of the compound.

26 Claims, 16 Drawing Sheets

(56) References Cited

FOREIGN PATENT DOCUMENTS

| | | |
|---|---|---|
| WO | 2011080718 A1 | 7/2011 |
| WO | 2011087776 A1 | 7/2011 |
| WO | 2011090760 A1 | 7/2011 |
| WO | 2012016217 A1 | 2/2012 |
| WO | 2013000994 A1 | 1/2013 |
| WO | 2013130976 A1 | 9/2013 |
| WO | 2014040555 A1 | 3/2014 |
| WO | 2014055634 A1 | 4/2014 |
| WO | 2014/071109 A1 | 5/2014 |
| WO | 2014124230 A2 | 8/2014 |
| WO | 2014130856 A2 | 8/2014 |
| WO | 2015030847 A1 | 3/2015 |
| WO | 2015048547 A2 | 4/2015 |
| WO | 2015108861 A1 | 7/2015 |
| WO | 2015154039 A2 | 10/2015 |
| WO | 2015157556 A1 | 10/2015 |
| WO | 2016025649 A1 | 2/2016 |
| WO | 2016106029 A1 | 6/2016 |
| WO | 2016162325 A1 | 10/2016 |
| WO | 2016205418 A1 | 12/2016 |
| WO | 2017068412 A1 | 4/2017 |
| WO | 2017080979 A1 | 5/2017 |
| WO | 2018019204 A1 | 2/2018 |

OTHER PUBLICATIONS

Rowe Raymond C. et al., "Handbook of Pharmaceutical Excipients 6th Edition, Pharmaceutical Press," London, England (2009) excerpts p. 1-17.

Oslodkin Dmitry I. et al., "Glycogen Synthase Kinase 3 as an Anticancer Drug Target: Novel Experimental Findings and Trends in the Design of Inhibitors," Current Pharmaceutical Design, 2013, 19, 665-679.

CAS Registry Extracts, 32 pp. (2008-2014).

\* cited by examiner

6-PYRIMIDIN-ISOINDOLE DERIVATIVE AS ERK1/2 INHIBITOR

CROSS REFERENCE TO RELATED APPLICATIONS

This application is a national stage filing under section 371 of International Application No. PCT/IB2018/052745, filed on Apr. 20, 2018, and published on Oct. 25, 2018 as WO 2018/193410, which claims priority to Great Britain Application No. 1706327.2, filed on Apr. 20, 2017. The entire contents of WO 2018/193410 are hereby incorporated herein by reference.

This invention relates to the compound (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, and in particular to novel physical forms of the compound, a process for preparing the compound and synthetic intermediates for use in the process, and novel formulations containing the compound, as well as therapeutic uses of the compound.

BACKGROUND OF THE INVENTION

MAPK Signalling and the Role of ERK1/2

The extracellular signal regulated kinases (ERK1/2) are ubiquitously expressed protein serine/threonine kinases that comprise a key component of the mitogen-activated protein kinase (MAPK) signalling pathway. The MAPK pathway is an evolutionary conserved cell signalling pathway that regulates a variety of cellular processes including cell cycle progression, cell migration, cell survival, differentiation, metabolism, proliferation and transcription. The ERK/MAPK signalling pathway responds to the extracellular stimulation of cell-surface receptor tyrosine kinases (RTKs). Upon activation of RTKs, the RAS GTPases (K-RAS, N-RAS and H-RAS) are converted from an inactive GDP-bound state to an active GTP-bound state. Activated RAS phosphorylates and thereby activates RAF (A-RAF, B-RAF and C-RAF), which in turn phosphorylates and activates the dual-specificity kinase MEK (MEK1/2). Subsequently, activated MEK phosphorylates and activates ERK1/2. Upon activation, ERK1/2 activates multiple nuclear and cytoplasmic substrates. There are currently >200 known ERK1/2 substrates, which include transcription factors, kinases, phosphatases and cytoskeletal proteins (Roskoski, Pharmacol. Res. 2012; 66: 105-143).

A number of isozymes of ERK have been identified (ERK1, ERK2, ERK3/4, ERK5, ERK7) but the two most widely studied isozymes are ERK1 and ERK2: see R. Roberts, *J. Exp. Pharm., The extracellular signal-regulated kinase (ERK) pathway: a potential therapeutic target in hypertension,* 2012: 4, 77-83, and Cargnello et al., *Microbiol. & Mol. Biol. Rev., Activation and Function of the MAPKs and Their Substrates, the MAPK-Activiated Protein Kinases* 2011, 50-83.

Upregulation of ERK1/2 Signalling in Cancer

ERK1/2 activity is commonly upregulated in cancer, as a result of activating mutations within upstream components of the MAPK pathway. Approximately 30% of human cancers contain activating RAS mutations (Roberts and Der, Oncogene. 2007; 26: 3291-3310). K-RAS is the most frequently mutated isoform and is mutated in 22% of all tumours. KRAS mutations are particularly prevalent in pancreatic adenocarcinoma (70-90%), non-small cell carcinoma (10-20%) and colorectal cancer (25-35%) (Neuzillet et al., 2014. Pharmacol. Ther. 141; 160-171). N-RAS and H-RAS mutations occur in 8% and 3% of cancers, respectively (Prior et al., Cancer Res. 2012; 72 (10); 2457-2467). Notably, activating N-RAS mutations have been reported in 15-20% of melanoma cases. Furthermore, activating B-RAF mutations occur in 8% of all tumours and are particularly prevalent in melanoma (50-60%), papillary thyroid cancer (40-60%), colorectal cancer (5-10%) and non-small cell lung cancer (3-5%) (Neuzillet et al., 2014. Pharmacol. Ther. 141; 160-171). In addition to the occurrence of activating RAS and RAF mutations, the MAPK signalling pathway can also be up-regulated in cancer by the over-expression or mutational activation of upstream RTKS such as EGFR (Lynch et al., *N Engl J Med.* 2004; 350: 2129-2139), HER2 (Stephens et al., Nature. 2004; 431: 525-526) and FGFR (Ahmed et al, Biochim. Biophys. Acta Mol. Cell. Res. 2012; 1823: 850-860).

There are multiple mechanisms by which aberrant ERK1/2 signalling can contribute to cancer progression. Upon activation, ERK1/2 phosphorylates and activates a wide range of transcription factors that are involved in promoting cell proliferation and differentiation, such as c-Fos (Murphy et al., Nat. Cell Biol. 2002: 4 (8):556-64) and ELK-1 (Gille et al., EMBO J. 1995; 14 (5):951-62). In addition, ERK1/2 signalling is known to promote cell cycle progression via multiple mechanisms, including the induction of D-type cyclins and repression of the cyclin-dependent kinase inhibitor p27$^{KIP1}$ (Kawada et al., Oncogene. 1997; 15: 629-637, Lavoie et al., J. Biol. Chem. 1996; 271: 20608-20616). Furthermore, ERK1/2 signalling can promote cell survival by regulating a range of apoptotic proteins. Examples of such mechanisms include the ERK1/2-dependent repression of the pro-apoptotic BCL-2 family proteins BIM1 and BAD (She et al., J. Biol Chem. 2002; 277: 24039-24048. Ley et al., J. Biol. Chem.2003; 278: 18811-18816) and the ERK1/2-dependent stabilisation of anti-apoptotic proteins such as MCL-1 (Domina et al., Oncogene. 2004; 23: 5301-5315).

Role of ERK1/2 in MAPK Inhibitor Resistance

A wide range of pre-clinical studies have demonstrated that the inhibition of the MAPK pathway suppresses the growth of cancer cell lines harbouring B-Raf or Ras mutations (Friday & Adjei, Clin. Cancer Res. 2008; 14: 342-346). The RAF inhibitors vemurafenib and dabrafenib, and the MEK inhibitor trametinib are clinically approved for the treatment of BRAF-mutant melanoma. These agents elicit profound anti-tumour responses in the majority of patients, although the duration of response is short-lived, due to the onset of acquired drug resistance (Chapman et al., N. Engl. J. Med. 2011; 364 2507-2516. Hauschild et al., Lancet. 2012; 380: 358-365. Solit and Rosen, N Engl J Med. 2011; 364 (8): 772-774. Flaherty et al., N. Engl. J. Med. 2012; 367: 1694-1703). Multiple mechanisms of acquired B-RAF inhibitor resistance have been identified.

These include the upregulation or activation of alternative MEK activators such as C-RAF or COT1 (Villanueva et al., Cancer Cell. 2010; 18:683-95. Johannessen et al., Nature. 2010; 468: 968-72), the upregulation of RTK or NRAS signalling (Nazarian et al., Nature. 2010; 468:973-7), and the onset of MEK activating mutations (Wagle et al., J Clin Oncol. 2011; 29:3085-96). Mechanisms of MEK inhibitor-resistance include the occurrence of MEK mutations that reduce drug binding or enhance intrinsic MEK activity (Emery et al., Proc Natl. Acad. Sci. 2009; 106: 20411-20416. Wang et al., Cancer Res. 2011; 71: 5535-5545), and BRAF or KRAS amplification (Little et al., Biochem Soc. Trans. 2012; 40(1): 73-8). A common feature of RAF or MEK inhibitor resistance mechanisms is the re-activation of ERK1/2 signalling, which drives proliferation and survival of the cells in the presence of inhibitors. Based on this observation, it has been suggested that direct ERK1/2 inhibition may be an effective therapeutic approach to overcoming acquired RAF or MEK inhibitor resistance. There is pre-clinical evidence that the inhibition of ERK1/2 overcomes acquired RAF or MEK inhibitor resistance (Hatzivassiliou et al., Mol Cancer Ther. 2012; 11(5):1143-54. Morris et al., Cancer Discov. 2013; 3 (7):742-50).

Additional Diseases

In addition to oncology, abnormal ERK1/2 signalling has also been reported in other diseases including cardiovascular disease (Muslin, Clin. Sci. 2008; 115: 203-218), Alzheimer's disease (Giovannini et al., Neuroscience. 2008; 153: 618-633), polycystic kidney disease (Omori et al., J Am Soc Nephrol. 2006; 17:1604-1614), Asthma (Duan et al., J Immunol. 2004; 172: 7053-7059) and emphysema (Mercer et al., J. Biol. Chem. 2004; 279: 17690-17696).

(2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide Our earlier International patent application number PCT/IB2016/001507 (the contents of which are incorporated herein by reference) discloses a class of benzolactam compounds as ERK2 inhibitors. One of the compounds specifically disclosed therein is the compound (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide which has the formula (1):

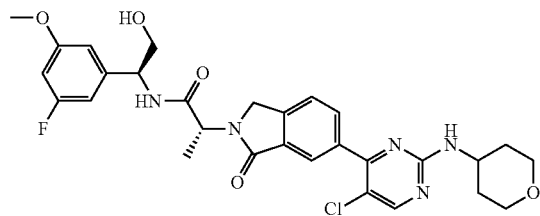

The preparation of this compound is described in Example 685 of PCT/IB2016/001507 and involves the reaction of a compound of the formula (2):

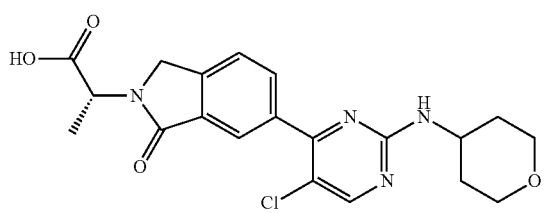

with a compound of formula (3):

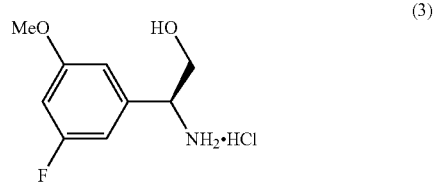

in dimethylformamide (DMF) and triethylamine in the presence of the amide bond-formation promoter O-(benzotriazol-1-yl)-N,N,N',N'-tetramethyluronium tetrafluoroborate (TBTU).

In Example 685, it is disclosed that, after work-up and partial purification by chromatography on silica, the eluate from the chromatography column was evaporated to give a glass which was then triturated with ether to give compound (1) as an amorphous solid.

SUMMARY OF THE INVENTION

In Example 685 of PCT/IB2016/001507, compound (1) is prepared in an amorphous form. However, it has now been found that a crystalline form of the compound of formula (1) can be prepared. Accordingly, in a first aspect, the invention provides the compound of formula (1) in a substantially crystalline form.

The present invention also provides novel methods of making the compound of the formula (1) and synthetic intermediates, and novel formulations comprising the compound of formula (1).

Crystalline Forms of the Compound of Formula (1)

In a first aspect, the invention provides (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, having the formula (1):

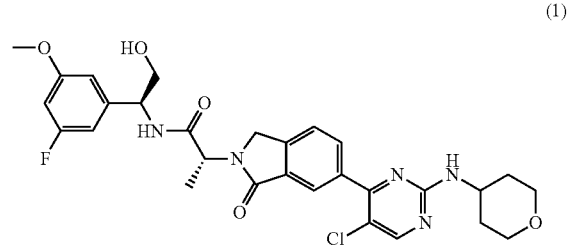 [SMILES: COc1cc(F)cc([C@@H](CO)NC(=O)[C@@H](C)N2Cc3ccc(-c4nc(NC5CCOCC5)ncc4Cl)cc3C2=O)c1]

or a tautomeric form thereof, in a substantially crystalline form.

Although the compound of formula (1) can form salts, references to the compound in a crystalline form are references to the free base.

References to the compound of formula (1), where the context admits, include within their scope all solvates, tautomers and isotopic variations thereof.

In an amorphous solid, the three dimensional structure that normally exists in a crystalline form does not exist and the positions of the molecules relative to one another in the amorphous form are essentially random, see for example Hancock et al. *J. Pharm. Sci.* (1997), 86, 1).

The term "substantially crystalline" refers to forms of the compound of formula (1) in which it is from 50% to 100% crystalline. Within this range, the compound of formula (1) may be at least 55% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline.

In a particular embodiment, the crystalline form is 95% to 100% crystalline, for example at least 98% crystalline, or at least 99% crystalline, or at least 99.5% crystalline, or at least 99.6% crystalline or at least 99.7% crystalline or at least 99.8% crystalline or at least 99.9% crystalline, for example 100% crystalline.

The crystalline forms of the compound of the invention may be solvated (e.g. hydrated) or non-solvated (e.g. anhydrous).

In one embodiment, the compound is anhydrous.

The term "anhydrous" as used herein does not exclude the possibility of the presence of some water on or in the compound (e.g. a crystal of the compound). For example, there may be some water present on the surface of the compound (e.g. compound crystal), or minor amounts within the body of the compound (e.g. crystal). Typically, an anhydrous form contains fewer than 0.4 molecules of water per molecule of compound, and more preferably contains fewer than 0.1 molecules of water per molecule of compound, for example 0 molecules of water.

In another embodiment, the compound is solvated, e.g. hydrated. Where the crystalline forms are hydrated, they can contain, for example, up to three molecules of water of crystallisation, more usually up to two molecules of water, e.g. one molecule of water or two molecules of water. Non-stoichiometric hydrates may also be formed in which the number of molecules of water present is less than one or is otherwise a non-integer. For example, where there is less than one molecule of water present, there may be for example 0.4, or 0.5, or 0.6, or 0.7, or 0.8, or 0.9 molecules of water present per molecule of compound (1).

In one embodiment, the crystalline form of compound (1) is a monohydrate and the crystal form contains one molecule of water of crystallisation.

Other solvates include alcoholates such as ethanolates and isopropanolates.

The crystalline forms described herein, crystals thereof and their crystal structure form further aspects of the invention.

The crystals and their crystal structures can be characterised using a number of techniques including, X-ray powder diffraction (XRPD), single crystal X-ray diffraction, differential scanning calorimetry (DSC) and thermogravimetric analysis (TGA). The behaviour of the crystals under conditions of varying humidity can be analysed by gravimetric vapour sorption studies (such as dynamic vapour sorption).

The crystalline structure of a compound can be analysed by the solid state technique of X-ray Powder Diffraction (XRPD). XRPD can be carried out according to conventional methods such as those described herein (see Example 4A) and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle (2θ) and interplanar spacing (d) parameters of an X-ray diffraction spectrum. These are related by Bragg's equation, $n\lambda = 2d \sin\theta$, (where n=1; λ=wavelength of the X-ray radiation; d=interplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually mean those that coincide in the range of 2θ±0.2°.

Two specific crystalline forms of the free base of compound (1) have been identified to date and these are referred to herein as "form A" and "form B". Of the two, form B appears to be the most stable form. Characterising data for both form A and form B are presented in the Examples below.

Both the A and B forms of crystalline (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide of the invention have been characterised by XRPD (see Examples 3 and 4 and FIGS. 1 and 2).

In each case, the powder X-ray diffraction patterns can be expressed in terms of the diffraction angle (2θ), inter planar spacing (d) and relative intensities of the peaks in the diffractogram.

Form A

A first crystalline form (form A) of the free base of compound (1) can be formed by disproportionation from a solution of the hydrochloric acid salt of compound (1) in a 3:1 water:propanol solvent mixture, as described in Example 3A below. The XRPD diffractogram for form A is shown in FIG. 1. During the disproportionation process, the acid dissociates from the free base and remains in solution to leave a suspension of the free base of compound (1).

Crystalline form A can also be prepared by suspending the amorphous hydrochloric acid salt of compound (1) in water at 70° C. for a prolonged period (e.g 96 hours) and then filtering off the crystalline material.

Form B

A second crystalline form (form B) of the free base can also be prepared by disproportionation of an acid addition salt (such as a hydrochloride, sulfate or hydrobromide salt) by prolonged stirring of an aqueous suspension of the salt in purified water but at a lower temperature than that employed to form the crystalline form A above. Thus, form B can be prepared as described in Examples 3B-3D below by suspending an amorphous mineral acid salt (such as a hydrochloride, sulfate or hydrobromide salt) of compound (1) in purified water at 18-23° C., then stirring the mixture at 45-50° C. for 20 hours, followed by further stirring at 30-35° C. for 96 hours and then filtering off the crystals of form B. The XRPD diffractogram of form B is shown in FIG. 2.

The disproportionation of an amorphous acid addition salt of compound (1) into crystalline form B can be assisted by the addition to the reaction mixture of an alcoholic co-solvent such as isopropanol.

In another method of making crystalline form B, compound (1) in amorphous free base form can be suspended in water which can be unbuffered or buffered up at a pH of about 2 up to pH 7 and then stirred at a slightly elevated temperature (e.g. 30° C.) for a period of time (e.g. up to six days, for example approximately five days) sufficient to allow conversion of the amorphous compound (1) into crystalline form B.

The X-ray diffraction pattern of crystalline form B of compound (1) exhibits peaks of greatest intensity at the diffraction angles set out in Table A, i.e. 14.0°, 20.6°, 24.0° and 24.2° (±0.2°).

TABLE A

| Diffraction Angle (°) | Relative Intensity |
|---|---|
| 14.0 | 100 |
| 20.6 | 85 |
| 24.0 | 74 |
| 24.2 | 71 |

Accordingly, in another embodiment, the invention provides a substantially crystalline form (form B)) of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide having an X-ray powder diffraction pattern characterised by the presence of major peaks at the diffraction angles (2θ) 14.0° and/or 20.6° and/or 24.0° and/or 24.2° (±0.2°).

In one embodiment, the X-ray diffraction pattern is characterised by the presence of at least one peak at a diffraction angle selected from 14.0°, 20.6°, 24.0° and 24.2° (±0.2°).

Thus, for example, in one embodiment, the invention provides a substantially crystalline form (form B) of compound (1) having an X-ray powder diffraction pattern characterised by the presence of a major peak at the diffraction angle 14.0° (±0.2°).

In another embodiment, the invention provides a substantially crystalline form (form B) of compound (1) having an X-ray powder diffraction pattern characterised by the presence of a major peak at the diffraction angle 20.6° (±0.2°).

In yet another embodiment, the invention provides a substantially crystalline form (form B) of compound (1) having an X-ray powder diffraction pattern characterised by the presence of a major peak at the diffraction angle 24.0° (±0.2°).

In yet another embodiment, the invention provides a substantially crystalline form (form B) of compound (1) having an X-ray powder diffraction pattern characterised by the presence of a major peak at the diffraction angle 24.2° (±0.2°).

In other embodiments, the substantially crystalline form (form B) of compound (1) has an X-ray powder diffraction pattern characterised by the presence of major peaks at two or more, e.g. three or more, and in particular four diffraction angle selected from 14.0°, 20.6°, 24.0° and 24.2° (±0.2°).

The X-ray powder diffraction pattern of form B of compound (1) may also have lesser peaks present at the diffraction angles set out in Table B, i.e. 8.8, 13.0, 13.8, 14.4, 17.3, 19.3, 21.3 and 28.7 (±0.2°).

TABLE B

| Diffraction Angle (°) | Relative Intensity |
|---|---|
| 8.8 | 23 |
| 13.0 | 23 |
| 13.8 | 39 |
| 14.4 | 20 |
| 17.3 | 22 |
| 19.3 | 36 |
| 21.3 | 45 |
| 28.7 | 22 |

The invention therefore also provides a substantially crystalline form (form B) of compound (1) having an X-ray powder diffraction pattern characterised by the presence of major peaks at the diffraction angles 14.0° and/or, 20.6° and/or 24.0° and/or 24.2° (±0.2°) as defined above and optionally one or more further peaks at diffraction angles selected from 8.8°, 13.0°, 13.8°, 14.4°, 17.3°, 19.3°, 21.3° and/or 28.7° (±0.2°).

In one embodiment, the substantially crystalline form (form B) of compound (1) has an X-ray powder diffraction pattern characterised by the presence of major peaks at the diffraction angles 14.0° and/or 20.6° and/or 24.0° and/or 24.2° (±0.2°); and optionally one or more further peaks at the diffraction angles 13.8° and/or 19.3° and/or 21.3° (±0.2°).

In a particular embodiment, the substantially crystalline form (form B) of compound (1) has an X-ray powder diffraction pattern characterised by the presence of major peaks at the diffraction angles 14.0°, 20.6°, 24.0°, 24.2°, 13.8°, 19.3° and 21.3° (±0.2°).

In another particular embodiment, the substantially crystalline form (form B) of compound (1) has an X-ray powder diffraction pattern characterised by the presence of major peaks at the diffraction angles 14.0°, 20.6°, 24.0°, 24.2°, 8.8°, 13.0°, 13.8°, 14.4°, 17.3°, 19.3°, 21.3° and 28.7° (±0.2°).

The X-ray powder diffraction pattern may be further characterised by the presence of additional peaks at the diffraction angles (2θ)(±0.2°) set out in Table C.

TABLE C

| Diffraction Angle (°) | Relative Intensity |
|---|---|
| 12.0 | 13 |
| 16.9 | 12 |
| 23.5 | 18 |
| 26.2 | 18 |
| 29.8 | 13 |

The invention further provides a substantially crystalline form (form B) of compound (1) which exhibits peaks at the same diffraction angles as those of the X-ray powder diffraction pattern shown in FIG. 2. Preferably the peaks have the same relative intensity as the peaks in FIG. 2.

In a preferred embodiment, the invention provides a substantially crystalline form (form B) of compound (1) having an X-ray powder diffraction pattern substantially as shown in FIG. 2.

The crystalline form of the invention can also be characterised by differential scanning calorimetry (DSC).

The crystalline form B of compound (1) has been analysed by DSC and has been found to exhibit an endothermic event with an onset temperature between 100° C. to 110° C. (more particularly from 101° C. to 108° C.) and a peak between 110° C. and 125° C. (more particularly between 111° C. and 114° C.) as shown in FIG. 3 of the accompanying drawings. This event is attributed to the release of water.

Accordingly, the invention provides a substantially crystalline form (form B) of compound (1) which exhibits an endothermic event having an onset temperature between 100° C. to 110° C. (more particularly 101° C. to 108° C.) when subjected to DSC. The invention also provides a substantially crystalline form (form B) of compound (1) which exhibits an endothermic event having a peak between 110° C. and 125° C. (more particularly between 111° C. and 113° C.).

The crystalline form (form B) of the invention can also be characterised by thermogravimetric analysis (TGA).

The substantially crystalline form B of compound (1) has been analysed by TGA and exhibits a weight loss transition with an onset temperature of 85° C. to 95° C., for example 90.86° C. which is complete at 110° C. to 130° C., for example 120° C. (see FIG. 4). The weight loss corresponds to the release of water.

On the basis of the DSC and TGA data, it is believed that the substantially crystalline form B of the compound (1) described above is a monohydrate. This has also been confirmed by single crystal X-ray diffraction studies (see Example 4E below).

In the substantially crystalline form B of compound (1), one single crystalline form may predominate, although other crystalline forms may be present in minor and preferably negligible amounts.

In a preferred embodiment, the invention provides compound (1) in a substantially crystalline form (form B) containing a single crystalline form having the XRPD properties described above, and no more than 5% by weight of any other crystalline forms of the compound.

Preferably, the single crystalline form (form B) is accompanied by less than 4%, or less than 3%, or less than 2% of other crystalline forms, and in particular contains less than or equal to about 1% by weight of other crystalline forms. More preferably, the single crystalline form is accompanied by less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, by weight of other crystalline forms, for example 0% by weight of other crystalline forms.

As will be evident from the foregoing paragraphs, the crystalline form (form B) of compound (1) can be characterised by a number of different physicochemical parameters. Accordingly, in one particular embodiment, the invention provides a substantially crystalline form (form B) of compound (1), which is characterised by any one or more (in any combination) or all of the following parameters, namely that it:

(a) has an X-ray powder diffraction pattern characterised by the presence of major peaks at the diffraction angles (2θ) and intensities set out in Table A, and optionally Table B; and further optionally wherein the X-ray powder diffraction pattern is characterised by the presence of major peaks at the diffraction angles (2θ) and intensities set forth in Table C; and/or (b) exhibits peaks at the same diffraction angles as those of the X-ray powder diffraction pattern shown in FIG. 2 and optionally wherein the peaks have the same relative intensities as the peaks in FIG. 2; and/or (c) has an X-ray powder diffraction pattern substantially as shown in FIG. 2; and/or (d) exhibits an endothermic peak between 100° C. and 115° C. when subjected to DSC; and/or (e) exhibits a weight loss between 85° C. and 130° C. (for example 90-120° C.) when subjected to thermogravimetric analysis (TGA).

Processes for Making Crystalline Forms of the Free Base of Compound (1)

The invention also provides processes for making crystalline forms of the free base of compound (1).

Accordingly, in another aspect of the invention, there is provided a process for making a substantially crystalline form of compound (1) free base; which method comprises:

(i) forming an aqueous suspension of an acid addition salt of compound (1) and stirring the suspension at a temperature of between 25° C. and 75° C. for a period of time sufficient to allow disproportionation of the acid addition salt and formation of the crystalline form of compound (1) free base to occur, and thereafter isolating the crystalline form; or (ii) forming an aqueous suspension of an amorphous form of compound (1) free base, wherein the aqueous suspension is unbuffered or is buffered to a pH of from 1.75 to 7.25, and stirring the aqueous suspension at a temperature of between 25° C. and 55° C. for a period of time sufficient to allow conversion of the amorphous form of the compound (1) free base to the crystalline form of compound (1) free base to occur, and thereafter isolating the crystalline form.

In process variant (i), the selection of the temperature and stirring time will have an influence on whether crystalline form A or form B is produced. Thus, for example, the process may be carried out at a higher temperature, for example 65-75° C. (and more particularly approximately 70° C.) in order to give form A. Conversely, the process may be carried out at a lower temperature, for example 25-55° C., to give crystalline form B.

The formation of a crystalline form may be facilitated by the addition to the process mixture of an alcohol such as isopropanol.

The starting material for process variant (i) is an acid addition salt of compound (1). The acid addition salt may be amorphous.

The acid addition salt of compound (1) may be, for example a mineral acid salt, such as a hydrochloride, hydrobromide or sulphate salt. Methods of making such salts will be well-known to those skilled in the art. The salt may be prepared by adding the free base compound to a solution of the counter-ion in a solvent. The solvent may be a polar, protic solvent, such as 2-propanol or methanol, and may include a polar, aprotic cosolvent, such as dichloromethane.

Process Variant (ii) Typically Leads to the Formation of Form B.

In process variant (ii), the aqueous suspension can be buffered or unbuffered. For example, it may either be unbuffered or buffered to a pH of 2, 5 or 7. The aqueous suspension is stirred with gentle heating, for example at a temperature of from about 25° C. to about 35° C., e.g. approximately 30° C. The aqueous suspension is stirred for a period of time sufficient to allow conversion of the amorphous form of the compound (1) free base to the crystalline form of compound (1) free base to occur. Typically, it is stirred for at least one day, more usually at least two days or at least three days and, in one embodiment, is stirred for five days.

In an alternative set of conditions in process variant (ii), the process may be carried out for a shorter period of time (for example at least 12 hours, or at least 15 hours; e.g. 20 hours) at a higher temperature (for example 45-55° C., an in particular approximately 50° C.). A seed crystal or either form A or form B may advantageously be added to assist the formation of the crystalline form B.

Amorphous salts of the compound of formula (1)

A number of amorphous salts of the compounds of formula (1) have been prepared (see Example 2). Accordingly, in a further aspect of the invention there is provided a salt of the compound of formula (1) in an amorphous form.

The salt may be the hydrochloride, sulphate, napadisylate (naphthalene-1,5-disulphonate), edisylate (ethanedisulphonate), tosylate (p-toluenesulphonate), mesylate (methanesulphonate), napsylate (2-naphthalenesulphonate), besylate (benzenesulphonate), isethionate (2-hydroxyethanesulphonate), esylate (ethanesulphonate) or hydrobromide salt of the compound of formula (1).

One set of salts consists of the amorphous hydrochloride, sulphate, hydrobromide or napadisylate salts of the compound of formula (1).

In other embodiments, the invention provides:

the amorphous hydrochloride salt of the compound of formula (1);

the amorphous sulphate salt of the compound of formula (1);

the amorphous hydrobromide salt of the compound of formula (1); and the amorphous napadisylate salt of the compound of formula (1).

The amorphous salts can be prepared by reacting the free base form of the compound with the appropriate acid in an organic solvent, preferably a polar, aprotic solvent (for example, isopropyl acetate) or a mixture of a polar aprotic solvent and a polar protic solvent (for example a mixture of isopropylacetate and 2-propanol).

The amorphous salts of the invention may be provided in the form of particles having a mass median diameter in the range from 1 μm to 100 μm.

The particles may have a mass median diameter in the range from 2 μm to 50 μm, for example from 2 μm to 25 μm or from 2 μm to 10 μm. The particles may be administered orally (typically as an orally administrable formulation optionally comprising one or more pharmaceutically acceptable excipients) or via other means, for example by inhalation. When the particles are intended for administration by inhalation, the particles typically have a mass median diameter of 1 μm to 10 μm or 1 μm to 5 μm.

The sizes of the particles can be determined by image analysis methods, laser diffraction methods or sieving techniques.

The particles may be produced via either mechanical micronisation processes or via solution-based phase separation processes. Examples of mechanical micronisation processes include milling techniques.

Solution-based techniques commonly involve using liquids, compressed gases, near-critical liquids or supercritical fluids as solvents or cryogenic media for rapid freezing. These techniques involve phase separation of the solvent and the pharmaceutical compound by evaporation, expansion, freezing or changing the composition of the solvent.

The particles may be producted by lyophilization. Alternatively, the particles may be formed by spray drying. Accordingly, in one embodiment, the amorphous salts of the invention are spray dried.

The amorphous salts may be used as therapeutic agents or may be used as intermediates in the preparation of crystalline forms of the free base of the compound of formula (1), as described above.

Methods for the Preparation of the Compound of Formula (1)

Compound (1) can be prepared by the series of process steps shown in Scheme 1 below.

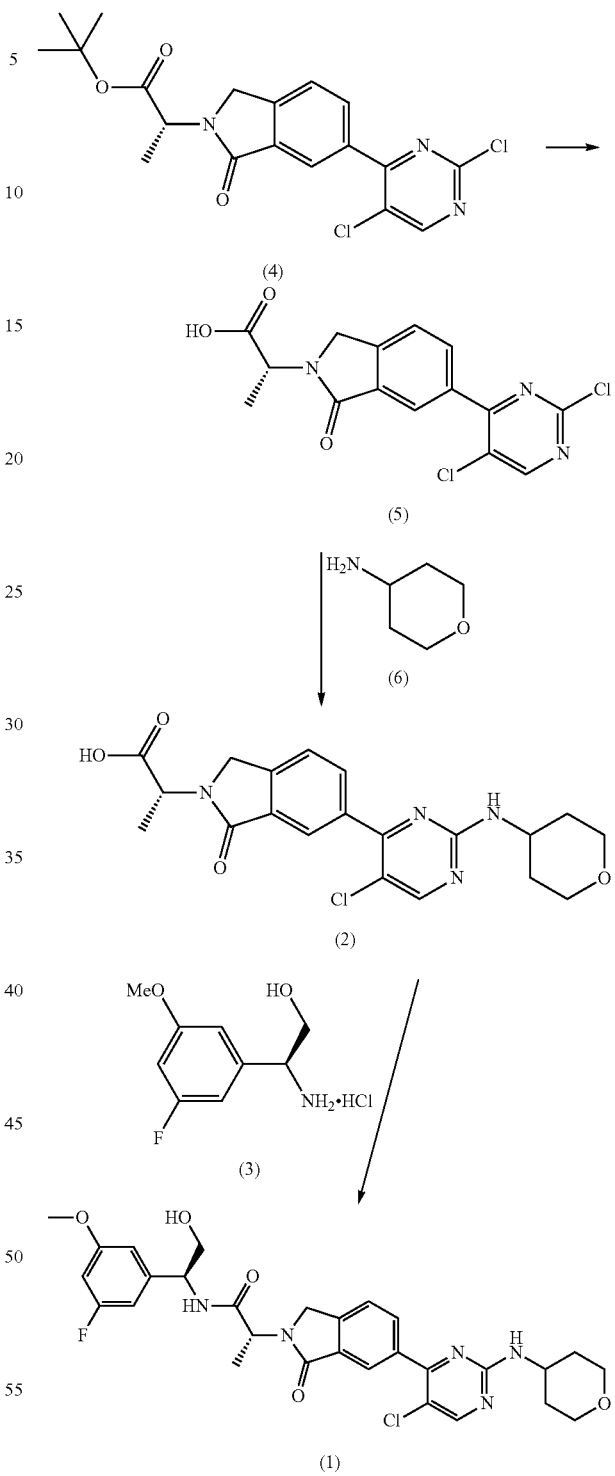

Scheme 1

The reaction of intermediate compound (2) with intermediate compound (3) to give compound (1) is described in Example 685 of our earlier application PCT/IB2016/001507. The reaction is carried out in dimethylformamide (DMF) and trimethylamine in the presence of the amide bond-formation promoter O-(benzotriazol-1-yl)-N,N,N',N'-tetramethyluronium tetrafluoroborate (TBTU). In PCT/IB2016/001507, intermediate compound (2) is prepared by hydrolysis of the corresponding tert-butyl ester which is itself prepared by reaction of intermediate compound (4) with the amine (6).

According to the present invention, a number of modifications have been made to the process described in In PCT/IB2016/001507.

Firstly, the process conditions for the final step, the reaction of intermediate compounds (2) and (3) have been modified. Thus, instead of using the coupling reagent TBTU, alternative coupling reagents such as N,N,N',N'-tetramethyl-O-(7-azabenzotriazol-1-yl)uronium hexafluorophosphate (HATU) and 1-ethyl-3-(3-dimethylaminopropyl)carbodiimide (EDOI) have been used. In addition, as well as triethylamine, alternative bases such as diisopropylethylamine (DIPEA) and 4-dimethylaminopyridine (DMAP) have been used.

Secondly, instead of reacting intermediate compound (4) with the amine (6) and then hydrolysing the tert-butyl ester moiety to give compound (2) as described in PCT/IB2016/001507, the tert-butyl ester moiety in intermediate compound (4) is first hydrolysed to give the carboxylic acid (5) which is then reacted with the amine (6) to give compound (2).

According to a further aspect of the invention, there is provided a process for preparing the compound of formula (1), which process comprises reacting a compound of the formula (2) with a compound of the formula (3):

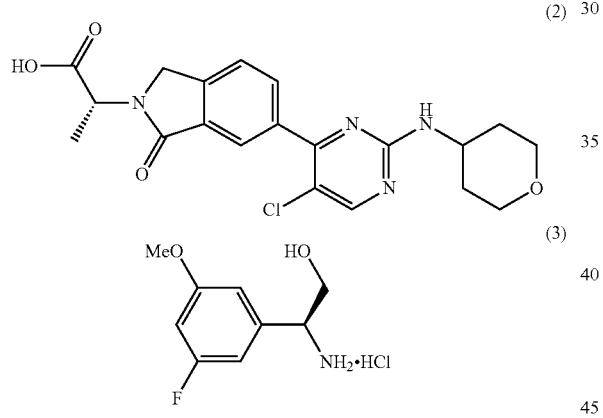

an aprotic solvent in the presence of a tertiary amine base and an amide-bond promoting agent wherein the amide-bond promoting agent is selected from N,N,N',N'-tetramethyl-O-(7-azabenzotriazol-1-yluronium hexafluorophosphate (HATU) and 1-ethyl-3-(3-dimethylaminopropyl)carbodiimide (EDOI).

In a particular embodiment, the amide-bond promoting agent is N,N,N',N'-tetramethyl-O-(7-azabenzotriazol-1-yl)uronium hexafluorophosphate (HATU).

Examples of tertiary amine bases for use in the process are diisopropylethylamine (DIPEA), 4-dimethylaminopyridine (DMAP) and triethylamine and mixtures thereof.

In a particular embodiment, the tertiary amine base is diisopropylethylamine (DIPEA).

Examples of aprotic solvents are dichloromethane, ethyl acetate and dimethylformamide.

In a particular embodiment, the aprotic solvent is dichloromethane.

In a preferred embodiment, there is provided a process for preparing the compound of formula (1), which process comprises reacting a compound of the formula (2) with a compound of the formula (3) in an aprotic solvent which is dichloromethane in the presence of a tertiary amine base which is diisopropylethylamine (DIPEA) and an amide-bond promoting agent which is N,N,N',N'-tetramethyl-O-(7-azabenzotriazol-1-yl)uronium hexafluorophosphate (HATU).

The reaction between compounds (2) and (3) is typically carried out without external heating and may, for example, be carried out at a temperature no greater than 25° C. Thus, for example, once the reactants have been mixed to form a reaction mixture, the reaction mixture may be stirred at a temperature in the range 15-25° C. until the reaction is complete.

In another aspect, the invention provides a process for making a compound of formula (1) as defined herein, which process comprises:

a) reacting a compound of formula (5):

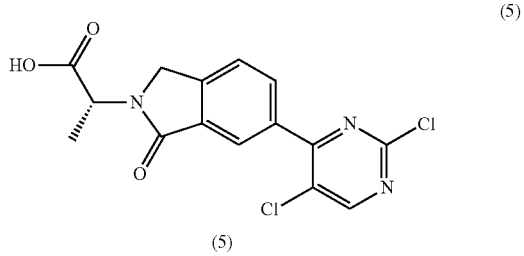 [SMILES: C[C@H](C(=O)O)N1Cc2ccc(-c3nc(Cl)ncc3Cl)cc2C1=O]

with a compound of formula (6)

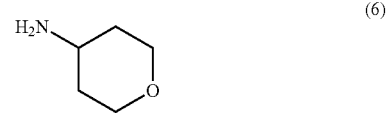

to give a compound of formula (2):

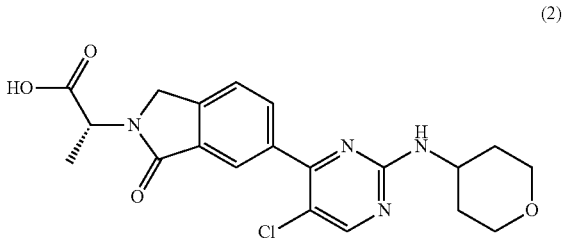 [SMILES: C[C@H](C(=O)O)N1Cc2ccc(-c3nc(NC4CCOCC4)ncc3Cl)cc2C1=O]

and b) reacting the compound of formula (2) with a compound of formula (3):

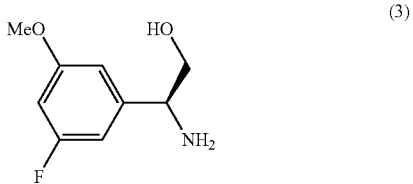 [SMILES: COc1cc(F)cc([C@H](N)CO)c1]

to give the compound of formula (1) and thereafter optionally forming a salt or crystalline form thereof.

Step (a) is typically carried out in a polar, aprotic solvent, such as 1-methyl-2-pyrrolidine (NMP). The reaction may be conducted at elevated temperatures; for example a temperature in excess of 60° C., more usually in excess of 70° C., an in particular a temperature in the range from 75-95° C. (e.g. 80 to 95° C.).

Step (a) is conducted in the presence of a base, which may be an inorganic base such as an alkali metal carbonate, e.g. potassium carbonate.

The progress of the reaction between the compounds of formulae (5) and (6) can be monitored to determine the extent of the reaction. For example, the reaction may be monitored until the residual amount of the compound of formula (5) is less than a desired level (for example, less than 1 mol % of its original amount). Step (a) typically has a reaction time between 1 to 8 hours, for example 2 to 7 hours, and typically 4 to 6 hours.

Step (b) is carried out under the conditions described above for the reaction between compounds (2) and (3) to give compound (1).

In a further aspect of the invention, there is provided a process for preparing the compound of formula (2), which process comprises:

a) reacting a compound of formula (5):

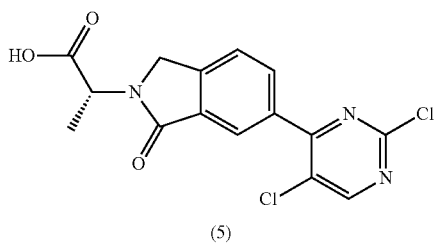

(5)

with a compound of formula (6)

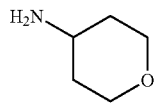

(6)

to give the compound of formula (2):

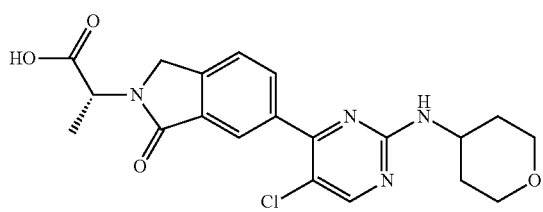

(2)

The reaction can be carried out under the conditions described in respect of step (b) above.

Compound (5) can be prepared by the hydrolysis of a tert-butyl ester compound of the formula (4):

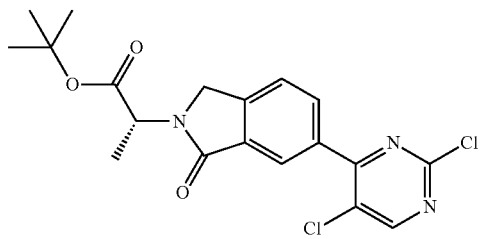

(4)

for example using a mineral acid such as concentrated hydrochloric acid. The hydrolysis reaction may be assisted by gentle heating, for example to a temperature in the range from 30-45° C., and more typically in the range 35-40° C. A co-solvent which may be a hydrocarbon or chlorinated hydrocarbon solvent may be used. Once such co-solvent is toluene.

Compound (4) can be prepared by the methods described in PCT/IB2016/001507; see for example Preparation 94 therein.

Compositions Comprising the Compound of Formula (1)

The compound of formula (1) has relatively poor solubility in water. The present invention therefore provides compositions of compound (1) in which comprise a main vehicle which is other than water. Such compositions are suitable for oral administration.

It has been found that compound (1) has good solubility in a number of non-aqueous solvents. Accordingly, the invention provides a pharmaceutical composition comprising the compound of formula (1) and a vehicle selected from:

a $C_{2-4}$ alcohol;
a polyether compound;
mono-esters of $C_8$ to $C_{18}$ long chain fatty acids with glycerol or propylene glycol;
di- or tri-glycerides of $C_8$ to $C_{10}$ long chain fatty acids; and mixtures thereof.

The pharmaceutical composition may take the form of a solution of compound (1) in the vehicle.

In a further aspect of the invention, there is provided a method of making a pharmaceutical composition comprising the compound of formula (1), the method comprising dispersing a compound of formula (1) in a vehicle selected from:

a $C_{2-4}$ alcohol;
a polyether compound;
mono-esters of $C_8$ to $C_{18}$ long chain fatty acids with glycerol or propylene glycol;
di- or tri-glycerides of $C_8$ to $C_{10}$ long chain fatty acids; and mixtures thereof.

Usually, the compound of formula (1) is dispersed in the vehicle to form a solution or a suspension. In one embodiment, the compound of formula (1) is suspended in the vehicle. In another embodiment, the compound of formula (1) is dissolved in the vehicle to form a suspension.

The vehicle may comprise a monohydric or polyhydric $C_{2-4}$ alcohol, preferably a $C_{2-3}$ alcohol, for example ethanol or propylene glycol.

Where the vehicle comprises a polyether compound, the polyether compound may be a polyethylene glycol (PEG). The polyethylene glycol may have an average molecular weight of 200 to 10,000 g/mol, for example 300 to 8,000 g/mol. In one embodiment, the polyethylene glycol has an average molecular weight of approximately 200 to 400 g/mol, for example 300 to 450 g/mol.

Depending upon the nature and relative quantities of the components of the vehicle, the compositions may be liquid, semi-solid or solid. For example, when a higher molecular weight PEG is used, the viscosity of the composition may be increased to the extent that it can be regarded as being a "semi-solid" or solid whereas lower molecular weight PEGs may give rise to liquid compositions. References to solutions in the context of such compositions includes solid solutions as well as liquid (or semi-solid) solutions Alternatively or additionally, the vehicle may comprise caprylic or capric acid and mono-, di- and tri-esters of caprylic or capric acids. Examples of such esters include propylene glycol monocaprylate, glycerol monocaprylate, glycerol dicaprylate, glycerol tricaprylate, glycerol mono-caprate, glycerol dicaprate, and glycerol tricaprate. Caprylocaproyl macrogol-8 glycerides (Labrasol® ALF) is a commerically available vehicle which contains a mixture of mono-, di- and tri-glycerol esters of caprylic and capric acids and also mono- and di-esters of polyethylene glycols with a average molecular weight of between 200 and 400 g/mol.

In another alternative, the vehicle may comprise a mono-glyceride of a longer chain fatty acid, such as linolic acid or oleic acid. Examples of such vehicles include Glycerol monolinoleate (Maisine CC™) and Glycerol monooleates (type 40, Peceol™)

In one embodiment, the vehicle is selected from ethanol, propylene glycol, polyethylene glycol and mixtures thereof. For example, the vehicle may comprise a combination of propylene glycol and ethanol, such as a combination of propylene glycol and ethanol in a 50:50 to 90:10% w/w ratio (for example, propylene glycol and ethanol in a 75:25 or 85:15% w/w ratio). In one embodiment, the vehicle comprises a combination of propylene glycol and ethanol in a ratio of 75:25 to 90:10% w/w.

In another embodiment, the vehicle is selected from ethanol, polyethylene glycol 400 (PEG 400) and propylene glycol, and mixtures thereof.

The composition typically allows for oral administration of the compound (1) to give a total daily dose of up to 1.2 g per day. In the compositions of the invention, the concentration of compound (1) in the vehicle may be in the range from 10 mg/ml to 130 mg/ml, for example 40 mg/ml to 125 mg/ml, and more particularly 110 mg/ml to 125 mg/ml. A concentration of 120 mg/ml allows for a 1.2 g dose of compound (1) to be administered in 10 ml of the composition.

Alternatively, the composition may be contained within a capsule. Suitable capsules for delivering compositions described herein include hard or soft gelatin capsules. In one embodiment, the composition is contained within a soft gelatin capsule. The term "gelatin" as used herein refers not only to capsules made from gelatin as such but also to capsules made from non-gelatin equivalents such as pullulan or modified celluloses such as hydroxypropylmethylcellulose.

The composition may also comprise one or more surfactants to aid the solubility of compound (1) in the selected vehicle(s). The surfactants may also act to inhibit precipitation of the compound of formula (1) when the composition is diluted in the gastro-intestinal tract.

The surfactants are typically non-ionic surfactants.

The non-ionic surfactant may be, for example, a polyol ester, polyoxyethylene ester or poloxamer.

In one embodiment, the surfactant is a tocopherol polyethylene glycol (TPG), such as D-α-tocopherol polyethylene glycol succinate (TPGS), having the formula:

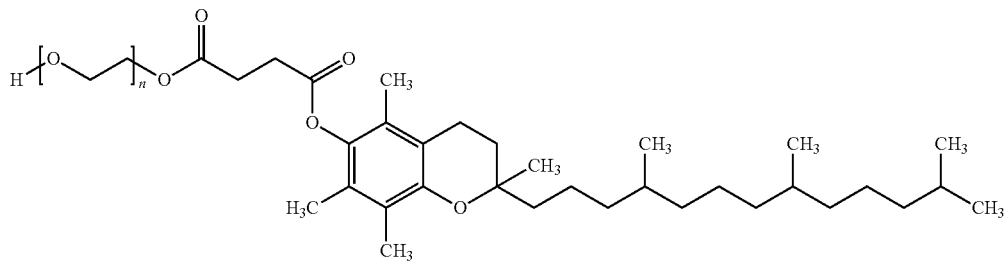

where the average value of n is in the region from about 10 to about 30, more typically in the range from about 15 to about 27; for example in the range from about 20 to 25. One particular TPGS is α-tocopherol polyethylene glycol 1000 succinate (approximate average molecular weight 1513) wherein the polyoxyethylene moiety [—O—CH$_2$—CH$_2$]$_n$ has a molecular weight of about 1000 (e.g. 950 to 1050) and the average value of n is about 22. Examples of polyol esters includes glycol and glycerol esters and sorbitan derivatives.

Fatty acid esters of sorbitan (generally referred to as Spans) and their ethoxylated derivatives (generally referred to as Tweens) include Sorbitan monolaurate (Span 20), Sorbitan monopalmitate (Span 40), Sorbitan monostearate (Span 60), Sorbitan mono-oleate (Span 80), Sorbitan tristearate (Span 65), Sorbitan trioleate (Span 8), Polyoxyethylene (20) sorbitan monolaurate (Tween 20), Polyoxyethylene (20) sorbitan monopalmitate (Tween 40), Polyoxyethylene (20) sorbitan monostearate (Tween 60), Polyoxyethylene (20) sorbitan mono-oleate (Tween 80), Polyoxyethylene (20) sorbitan tristearate (Tween 65) and Polyoxyethylene (20) sorbitan tri-oleate (Tween 85).

Other particular examples of surfactants include polyoxyl 40 hydrogenated castor oil (Cremophor RH 40, Kolliphor® RH40), polyoxyl 35 castor oil (Cremophor EL, Kolliphor® EL), polysorbate 80 (Tween 80), Gelucire 44/14 (Lauroyl macrogol-32 glycerides), Solutol HS-15 (Macrogol 15 hydroxystearate) and Labrasol® ALF (caprylocaproyl macrogol-8 glycerides). In one embodiment the surfactant is Cremophor RH 40.

In one embodiment, the composition comprises the compound of formula (1), ethanol and a tocopherol polyethylene glycol (TPG), for example D-α-Tocopherol polyethylene glycol 1000 succinate (TPGS). The ethanol and TPG may be present in a ratio in the range of 20:80 ethanol:TPG to 60:40 ethanol:TPG, for example, 30:70 ethanol:TPG to 50:50 ethanol.

In another embodiment, the composition comprises, in addition to the compound of formula (1), a vehicle comprising:

(i) propylene glycol;
(ii) a non-ionic surfactant (such as Cremophor RH40 and a tocopherol polyethylene glycol); and optionally
(iii) ethanol.

In another embodiment, the composition comprises, in addition to the compound of formula (1), a vehicle comprising:
(i) propylene glycol;
(ii) a polyoxyethylene ester non-ionic surfactant; and optionally
(iii) ethanol.

The polyoxyethylene ester non-ionic surfactant may be, for example, a tocopherol polyethylene glycol (TPG), such as D-α-tocopherol polyethylene glycol succinate (TPGS) as hereinbefore defined.

In one particular embodiment, the compositions contains no ethanol (iii).

In another particular embodiment, the compositions contains ethanol (iii).

In another particular embodiment, the vehicle comprises propylene glycol and a tocopherol polyethylene glycol (TPG). In this embodiment, the vehicle may comprise TPGS in a weight ratio of 1:2 to 10:1 propylene glycol:TPGS and may optionally further comprise ethanol in a weight ratio of 1:10 to 2:1 ethanol:propylene glycol (for example D-α-Tocopherol polyethylene glycol 1000 succinate (TPGS)) in a weight ratio of from 1:2 to 5:1 propylene glycol:tocopherol polyethylene glycol; and optionally further comprising ethanol in a weight ratio of ethanol:propylene glycol of from 1:10 to 2:1.

The compositions comprising the compound of formula (1), propylene glycol, polyoxyethylene ester non-ionic surfactant; and optionally the ethanol may conveniently be contained within a capsule, for example a hard gelatin or soft gelatin capsule.

The compound of formula (1) in step a) may be in a crystalline form. In one embodiment, the compound of formula (1) in step a) is in a crystalline form as described herein.

The low aqueous solubility of pharmaceutical compounds may be improved by reducing the solid particle size of the compounds. By reducing the particle size of the pharmaceutical compound, the surface area available for solvation is increased.

Accordingly, in a further aspect of the invention, there is provided a compound of formula (1) in the form of particles having a mass median diameter of between 1 μm and 100 μm.

The particles may have a mass median diameter of between 2 μm and 50 μm, for example between 2 μm and 25 μm or between 2 μm and 10 μm. The particles may be administered orally (typically as an orally administrable formulation optionally comprising one or more pharmaceutically acceptable excipients) or via other means, for example by inhalation. When the particles are intended for administration by inhalation, the particles typically have a mass median diameter of 1 μm to 10 μm or 1 μm to 5 μm.

The sizes of the particles can be determined by image analysis methods, laser diffraction methods or sieving techniques.

The particles may be produced via either mechanical micronisation processes or via solution-based phase separation processes. Examples of mechanical micronisation processes include milling techniques.

Solution-based techniques commonly involve using liquids, compressed gases, near-critical liquids or supercritical fluids as solvents or cryogenic media for rapid freezing. These techniques involve phase separation of the solvent and the pharmaceutical compound by evaporation, expansion, freezing or changing the composition of the solvent.

The particles may be producted by lyophilization. Alternatively, the particles may be formed by spray drying.

Definitions

The compound of formula (1) may be referred to in this application by its chemical name or, for convenience, as "the compound", "the compound of formula (1)", "compound (1)" or "the compound of the invention". Each of these synonyms refers to the compound shown in formula (1) above and having the chemical name (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

The term mass median diameter, as used herein to define particle sizes, is defined as the diameter at which 50% of the particles by mass are larger in diameter and 50% are smaller in diameter. The diameter refers to the equivalent spherical diameter, which for a non-spherical particle is equal to the diameter of a spherical particle having the same volume of the non-spherical particle.

By ERK1/2 we mean either or both of the ERK1 and ERK2 isozymes of extracellular signal regulated kinases (ERK).

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to an enzyme. Efficacy is the relationship between target occupancy and the ability to initiate a response at the molecular, cellular, tissue or system level.

The term "inhibitor" refers to an enzyme inhibitor that is a type of ligand or drug that blocks or dampens biological responses mediated by ERK1/2. Inhibitors mediate their effects by binding to the active site or to allosteric sites on enzymes, or they may interact at unique binding sites not normally involved in the biological regulation of the enzyme's activity. The inhibition may arise directly or indirectly, and may be mediated by any mechanism and at any physiological level. As a result, inhibition by ligands or drugs may under different circumstances manifest itself in functionally different ways. Inhibitory activity may be reversible or irreversible depending on the longevity of the inhibitor-enzyme complex, which, in turn, depends on the nature of inhibitor-enzyme binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur and does not include amelioration of the condition, diminishment or alleviation of at least one symptom associated or caused by the condition being treated and cure of the condition.

References to the prophylaxis or treatment of a disease state or condition such as cancer include within their scope alleviating or reducing the incidence e.g. of cancer.

As used herein, the term "mediated", as used e.g. in conjunction with ERK1/2 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50% provided that it is greater than 0%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

Salts, Solvates, Tautomers and Isotopes

A reference to the compound of the formula (1) includes ionic forms, salts, solvates, tautomers and isotopic variants thereof, unless the context indicates otherwise.

Salts

The compound of the formula (1) can exist in the form of salts, and in particular acid addition salts. All such salts are within the scope of this invention, and references to compound of the formula (1) include the salt forms of the compound, unless the context indicates otherwise otherwise.

Salts of compound (1) can be synthesized from compound (1) by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the appropriate acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

The salt forms of the compound of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compound of the invention, also form part of the invention.

Geometric Isomers and Tautomers

The compound of the formula (1) may exist in a number of different tautomeric forms and references to compound of the formula (1) include all such forms, unless the context indicates otherwise. For the avoidance of doubt, where the compound can exist in one of or tautomeric forms and only one is specifically described or shown, all others are nevertheless embraced by formula (1).

The convention of using 'hashed' or 'wedged' lines to indicate stereochemistry has been used to designate particular stereochemical forms, for example as illustrated by the two molecules depicted below.

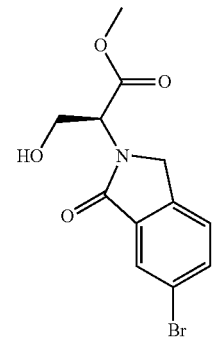

Methyl (S)-2-(6-bromo-1-oxoisoindolin-2-yl)-3-hydroxypropanoate

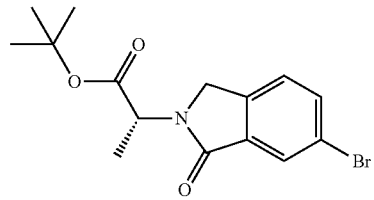

tert-butyl (R)-2-(6-bromo-1-oxoisoindolin-2-yl)propanoate

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic, separating the diastereoisomers by preferential crystallisation, and then dissociating the salts to give the individual enantiomer of the free base. Likewise, optical isomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product. For example, optical isomers of chiral compounds containing a free hydroxyl group can be separated by forming Mosher's acid esters and then separating the resulting diastereoisomers by chromatography, followed by cleavage of the ester to regenerate the free hydroxyl group.

Where a specific stereochemical configuration is shown in compounds in the present application, this may be taken to mean that at least 55% (e.g. at least 60%, 65%, 70%, 75%, 80%, 85%, 90% or 95%) of the compound is present in that stereochemical form as distinct from other isomeric forms of the compound. In one general embodiment, 99% or more (e.g. substantially all) of the total amount of the compound of the formula (1) is present in the stereochemical configuration depicted.

Isotopic Variations

References herein to compound (1) include all pharmaceutically acceptable isotopically-labeled variations thereof, wherein one or more atoms are replaced by atoms having the same atomic number, but an atomic mass or mass number different from the atomic mass or mass number usually found in nature.

Examples of isotopes suitable for inclusion in the compound of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, nitrogen, such as $^{13}$N and $^{15}$N, and oxygen, such as $^{15}$O, $^{17}$O and $^{18}$O.

Certain isotopically-labelled compounds of formula (1), for example, those incorporating a radioactive isotope, are useful in drug and/or substrate tissue distribution studies. The compound of formula (1) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$O, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances. In particular, every reference to hydrogen in the application should be construed as covering $^1$H and $^2$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O, and $^{13}$N, can be useful in Positron Emission Topography (PET) studies for examining target occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed.

Complexes

Formula (1) also includes within its scope complexes (e.g. inclusion complexes or clathrates with compounds such as cyclodextrins, or complexes with metals) of the compound. Inclusion complexes, clathrates and metal complexes can be formed by means of methods well known the skilled person.

Biological Properties

It is envisaged that compound (1) will be useful in medicine or therapy.

The compound of the invention is an inhibitor of ERK1/2, and will be useful in preventing or treating disease states or conditions described herein, for example the diseases and conditions discussed below and the diseases and conditions described in the "Background of the Invention" section above in which ERK1/2 plays a role. In addition the compound of the invention will be useful in preventing or treating diseases or conditions mediated by ERK1/2, for example diseases or conditions such as cancers in which ERK1/2 activity is required or upregulated as a result of activating mutations within upstream components (such as RAS, K-RAS, NRAS and RAF) of the MAPK pathway.

References to the prevention or prophylaxis or treatment of a disease state or condition such as cancer include within their scope alleviating or reducing the incidence of the disease or condition. Thus, for example, it is envisaged that the compound of the invention will be useful in alleviating or reducing the incidence of cancer.

References to the compound of formula (1) below include the crystalline forms of the compound of formula (1) described herein and the compound of formula (1) prepared according to the methods described herein.

Accordingly, in further embodiments of the invention, there are provided:

The compound of formula (1) for use in medicine.

The compound of formula (1) for use in preventing or treating a disease or condition mediated by ERK1/2.

The use of the compound of formula (1) for the manufacture of a medicament for preventing or treating a disease or condition mediated by ERK1/2.

A method of preventing or treating a disease or condition mediated by ERK1/2 in a subject (e.g. a mammalian subject, such as a human, in need thereof), which method comprises administering to the subject a therapeutically effective amount of the compound of formula (1).

The compound of formula (1) for use in alleviating or reducing the incidence of a disease or condition mediated by ERK1/2.

The use of the compound of formula (1) for the manufacture of a medicament for alleviating or reducing the incidence of a disease or condition mediated by ERK1/2.

A method of alleviating or reducing the incidence of a disease or condition mediated by ERK1/2 in a subject (e.g. a mammalian subject, such as a human, in need thereof), which method comprises administering to the subject a therapeutically effective amount of the compound of formula (1).

More particularly, compound (1) is an inhibitor of ERK1/2. For example, the compound of the invention has inhibitory potency against ERK1 or ERK2, and in particular against ERK1/2.

The ERK inhibitor compound of formula (1) is capable of binding to ERK1/2 and exhibiting potency for ERK1/2. In one embodiment the inhibitor compound of formula (1) exhibits selectivity for ERK1/2 over other kinase family members, and may be capable of binding to and/or exhibiting inhibition of ERK1 and/or ERK2 in preference to binding to and/or exhibiting inhibition of other of the kinase family members.

ERK1/2 function in controlling cell signalling has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

The disease or condition mediated by ERK1/2 referred to in any of the foregoing embodiments may be any one or more of the above diseases and disorders.

Therefore, it is also envisaged that the compound of the invention as defined herein may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of its affinity for ERK1/2, the compound of the invention will be useful in providing a means of controlling cell signalling. It is therefore anticipated that the compound may prove useful in treating or preventing proliferative disorders such as cancers.

Accordingly, in further embodiments, the invention provides:

The compound of formula (1) for use in preventing or treating proliferative disorders such as cancers.

The use of the compound of formula (1) for the manufacture of a medicament for preventing or treating proliferative disorders such as cancers.

A method of preventing or treating proliferative disorders such as cancers in a subject (e.g. a mammalian subject, such as a human, in need thereof), which method comprises administering to the subject a therapeutically effective amount of the compound of formula (1).

The compound of formula (1) for use in alleviating or reducing the incidence of proliferative disorders such as cancers.

The use of the compound of formula (1) for the manufacture of a medicament for alleviating or reducing the incidence of proliferative disorders such as cancers.

A method of alleviating or reducing the incidence of proliferative disorders such as cancers in a subject (e.g. a mammalian subject, such as a human, in need thereof), which method comprises administering to the subject a therapeutically effective amount of the compound of formula (1).

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; neural crest cell-derived tumours including melanocytic tumours (for example malignant melanoma or uveal melanoma), tumours of peripheral and cranial nerves, peripheral neuroblastic tumours (for example neuroblastoma), embryonal tumors of the CNS, paraganglioma; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum). Further examples of cancers (and their benign counterparts) which may be treated (or inhibited) include, but are not limited to tumours of testes and brain (e.g. neuromas).

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancy is leukaemia. In another embodiment the haematological malignancy is lymphoma. In one embodiment, the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment, the compound of the invention is for use in the prophylaxis or treatment of lymphoma, such as acute or chronic lymphoma in particular Burkitt lymphoma, Hodgkin lymphoma, non-Hodgkin lymphoma or diffuse large B-cell lymphoma. In one embodiment, the compound of the invention is for use in the prophylaxis or treatment of acute myeloid leukaemia (AML) or acute lymphocytic leukaemia (ALL). In one embodiment, the cancer is AML. In another embodiment, the cancer is CLL.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. The compound of the invention may therefore be useful in preventing and disrupting initiation of tumour angiogenesis. In particular, the compound of the invention may be useful in the treatment of metastasis and metastatic cancers.

Metastasis or metastatic disease is the spread of a disease from one organ or part to another non-adjacent organ or part. The cancers which can be treated by the compound of the invention include primary tumours (i.e. cancer cells at the originating site), local invasion (cancer cells which penetrate and infiltrate surrounding normal tissues in the local area), and metastatic (or secondary) tumours i.e. tumours that have formed from malignant cells which have circulated through the bloodstream (haematogenous spread) or via lymphatics or across body cavities (trans-coelomic) to other sites and tissues in the body.

In the foregoing embodiments, particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

Another subset of cancers consists of renal, melanoma, colon, lung, breast, ovarian and prostate cancers.

Another subset of cancers consists of pancreatic cancers.

Another subset of cancers consists of leukemaia, such as acute and chronic leukaemias, acute myeloid leukaemia (AML), and chronic lymphocytic leukaemia (CLL).

A further subset of cancers consists of mesothelioma including malignant peritoneal mesothelioma or malignant pleural mesothelioma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia. In this regard, references to prostate cancer include prostate cancers with resistance towards anti-androgen therapy, in particular abiraterone or enzalutamide, or castrate-resistant prostate cancer. References to melanoma include melanomas that are resistant to treatment with BRAF and/or MEK inhibitors.

The cancers may be cancers which are sensitive to inhibition of either ERK1 or ERK2 or most particularly ERK1/2.

It is further envisaged that the compound of the invention will be particularly useful in the treatment or prevention of cancers of a type associated with or characterised by the presence of elevated Ras, BRAF and/or MEK signalling.

Elevated levels of Ras, BRAF or MEK signalling are found in many cancers and are associated with a poor prognosis. In addition, cancers with activating Ras, BRAF or MEK mutations may also be sensitive to an ERK1/2 inhibitor. The elevated levels of Ras, BRAF or MEK signalling and mutations in Ras, BRAF or MEK can be identified by the techniques outlined herein. Whether a particular cancer is one which is sensitive to ERK1/2 inhibition may be determined by a method as set out in the section headed "Methods of Diagnosis".

A further subset of cancers consists of NRas melanoma and NRas AML.

Another subset of cancers consists of KRas lung cancer, KRas pancreatic cancer and KRas colorectal cancer (CRC).

Another subset of cancers consists of BRAF colorectal cancer (CRC), BRAF lung cancer and BRAF melanoma.

In further embodiments, the invention provides:

The compound of formula (1) for use in preventing or treating a disease or condition with mutant Ras, mutant BRAF or mutant MEK.

The use of the compound of formula (1) for the manufacture of a medicament for preventing or treating a disease or condition with mutant Ras, mutant BRAF or mutant MEK.

A method of preventing or treating a disease or condition with mutant Ras, mutant BRAF or mutant MEK in a subject (e.g. a mammalian subject, such as a human, in need thereof), which method comprises administering to the subject a therapeutically effective amount of the compound of formula (1).

The compound of formula (1) for use in alleviating or reducing the incidence of a disease or condition with mutant Ras, mutant BRAF or mutant MEK.

The use of the compound of formula (1) for the manufacture of a medicament for alleviating or reducing the incidence of a disease or condition with mutant Ras, mutant BRAF or mutant MEK.

A method of alleviating or reducing the incidence of a disease or condition with mutant Ras, mutant BRAF or mutant MEK in a subject (e.g. a mammalian subject, such as a human, in need thereof), which method comprises administering to the subject a therapeutically effective amount of the compound of formula (1).

The compound of formula (1) for use in the treatment of (or reduction in the incidence of) a cancer selected from NRas melanoma and NRas AML.

The compound of formula (1) for use in the treatment of (or reduction in the incidence of) a cancer selected from KRas lung cancer, KRas pancreatic cancer and KRas colorectal cancer (CRC).

The compound of formula (1) for use in the treatment of (or reduction in the incidence of) a cancer selected from BRAF colorectal cancer (CRC), BRAF lung cancer and BRAF melanoma.

The compound of formula (1) for use in the treatment of (or reduction in the incidence of) a cancer which is BRAF melanoma.

The use of the compound of formula (1) for the manufacture of a medicament for preventing or treating a cancer as defined herein.

A method of treating (or reducing the incidence of) a cancer in a subject (e.g. a mammalian subject such as a human), which method comprises administering to the subject a therapeutically effective amount of the compound of formula (1).

The compound of formula (1) for use in the treatment of a disease or condition as described herein, in particular cancer.

The use of the compound of formula (1) for the manufacture of a medicament for the treatment of a disease or condition as described herein, in particular cancer.

A method of preventing or treating a disease or condition as described herein, in particular cancer, in a subject (e.g. a mammalian subject, such as a human, in need thereof), which method comprises administering to the subject a therapeutically effective amount of the compound of formula (1).

The compound of formula (1) for use in alleviating or reducing the incidence of a disease or condition as described herein, in particular cancer.

The use of the compound of formula (1) for the manufacture of a medicament for alleviating or reducing the incidence of a disease or condition as described herein, in particular cancer.

A method of alleviating or reducing the incidence of a disease or condition as described herein, in particular cancer, in a subject (e.g. a mammalian subject, such as a human, in need thereof), which method comprises administering to the subject a therapeutically effective amount of the compound of formula (1).

The compound (1) may also be useful in the treatment of tumour growth, pathogenesis, resistance to chemo- and radio-therapy by sensitising cells to chemotherapy, and as an anti-metastatic agent.

Therapeutic anticancer interventions of all types necessarily increase the stresses imposed on the target tumour cells. In mitigating the deleterious effects of such stresses, ERK1/2 are directly implicated in resisting the effects of cancer drugs and treatment regimens. Thus, inhibitors of ERK1/2 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of its inhibition of ERK1/2, the compound will be useful in providing a means of controlling cell signalling. Therefore, it is also envisaged that the compound of the invention may be useful in treating other conditions such as inflammatory disorders such as hepatitis, ulcerative colitis, and gastritis; neurodegenerative conditions such as Alzheimer's disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compound of the invention as an inhibitor of ERK1/2 can be measured using the biological and biophysical assays set forth in the examples herein.

Methods of Diagnosis

Prior to administration of a compound of the formula (1), a subject (e.g. a patient) may be screened to determine whether a disease or condition from which the patient is or may be suffering is one which would be susceptible to treatment with a compound showing inhibition of ERK1/2. The term 'patient' includes human and veterinary patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of ERK1/2 signalling or to sensitisation of a pathway to normal ERK1/2 function or to upregulation of a biochemical pathway downstream of ERK1/2 activation.

Examples of such abnormalities that result in activation or sensitisation of the ERK1/2 pathway, include activating mutations in a Ras isoform such as KRAS or in BRAF, as discussed in the Background section.

Mutations of Ras have been detected in cell lines and primary tumours including but not limited to melanoma, colorectal cancer, non-small cell lung cancer, and cancers of the pancreas, prostate, thyroid, urinary tract and upper respiratory tract (Cancer Res. 2012; 72: 2457-2467).

The term up-regulation includes elevated expression or over-expression, including gene amplification (i.e. multiple gene copies), cytogenetic aberration and increased expression by a transcriptional effect, or increased signalling through activation of ERK1/2. Thus, the patient may be subjected to a diagnostic test to detect a marker characteristic of up-regulation of ERK1/2. The term diagnosis includes screening. By marker we include genetic markers including, for example, the measurement of DNA composition to identify presence of mutations of Ras (e.g. KRAS) or BRAF. The term marker also includes markers which are characteristic of up regulation of ERK1/2, including protein levels, protein state and mRNA levels of the aforementioned proteins. Gene amplification includes greater than 7 copies, as well as gains of between 2 and 7 copies.

Diagnostic assays for detecting KRAS and BRAF mutations are described in de Castro et al. Br. J. Cancer. 2012 Jul. 10; 107(2):345-51. doi: 10.1038/bjc.2012.259. Epub 2012 Jun. 19, "A comparison of three methods for detecting KRAS mutations in formalin-fixed colorectal cancer specimens."; and Gonzalez et al., Br J Dermatol. 2013, April; 168(4): 700-7. doi: 10.1111/bjd.12248, "BRAF mutation testing algorithm for vemurafenib treatment in melanoma: recommendations from an expert panel" and references cited therein.

A number of diagnostic tests for BRAF mutations have been approved by the FDA and details of the tests can be found on the FDA website. Examples of such diagnostic tests are the cobas 4800 BRAF V600 Mutation Test, a companion assay for Roche's vemurafenib product, and the THxID BRAF test, a companion test for the Tafinlar (dabrafenib) and Mekinist (trametinib) products.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Clinical testing for most genetic variants could include, but are not limited to, standard methods such as allele-specific polymerase chain reaction (PCR), reverse-transcriptase polymerase chain reaction (RT-PCR), DNA sequence analysis by conventional Sanger or next-generation sequencing methods, Sanger dideoxy sequencing, pyrosequencing, multiplex ligation-dependent probe amplification (MLPA), or ARMS PCR. Clinical testing for gene copy number and structural gene variations could include, but are not limited to, standard methods such as RNA sequencing (RNAseq), nanostring hybridisation proximity RNA nCounter assays, or in-situ hybridization such as fluorescence in situ hybridization (FISH). Newer, next-generation sequencing (NGS) technologies, such as massively parallel sequencing allow for whole exome sequencing or whole genome sequencing.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Particular probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis e.g. from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays or to gene-specific oligonucleotide probes on Human Genome Arrays. Alternatively, single nucleotide polymorphism (SNP) arrays, a type of DNA microarray, can be used to detect polymorphisms within a population.

Alternatively, the protein products expressed from the mRNAs may be assayed by immunohistochemistry or immunofluorescence of tumour samples, solid phase immunoassay with microtitre plates, Western blotting, capillary electrophoresis, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of ERK1/2, detection of ERK1/2 variants or mutants, or detection of 11q22 amplification could be applicable in the present case.

Abnormal levels of proteins such as ERK1/2 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

ERK overexpression can be measured by tumour biopsy. Methods for assessing gene copy changes include techniques commonly used in cytogenetic laboratories such as MLPA (Multiplex Ligation-dependent Probe Amplification), a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an inhibitor.

Therefore, all of these techniques could also be used to identify tumours particularly suitable for treatment with the compound of the invention.

Accordingly, in further embodiments, the invention provides:

The compound of formula (1) for use in the treatment or prophylaxis of (or for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor).

The use of the compound of formula (1) for the manufacture of a medicament for the treatment or prophylaxis of (for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor).

A method for the treatment or prophylaxis of (for use in alleviating or reducing the incidence of) a disease state or condition in a patient who has been screened and has been determined as suffering from, or being at risk of suffering from, a disease or condition which would be susceptible to treatment with a compound showing inhibition of ERK1/2 (i.e. an ERK1/2 inhibitor), which method comprises administering to the subject a therapeutically effective amount of the compound of formula (1).

Another aspect of the invention includes a compound of the invention for use in the prophylaxis or treatment of cancer in a patient selected from a sub-population possessing overexpression or an activating mutation in the ERK1/2 signalling pathway (e.g. Ras, BRAF or MEK). Accordingly, in further embodiments, the invention provides:

The compound of formula (1) for use in the treatment or prophylaxis of (or for use in alleviating or reducing the incidence of) cancer in a patient selected from a sub-population possessing overexpression or an activating mutation in the ERK1/2 signalling pathway, for example Ras (e.g. KRAS), BRAF or MEK.

The use of the compound of formula (1) for the manufacture of a medicament for the treatment or prophylaxis of (for use in alleviating or reducing the incidence of) cancer in a patient selected from a sub-population possessing overexpression or an activating mutation in the ERK1/2 signalling pathway Ras (e.g. KRAS), BRAF or MEK.

A method for the treatment or prophylaxis of (for use in alleviating or reducing the incidence of) cancer in a patient selected from a sub-population possessing overexpression or an activating mutation in the ERK1/2 signalling pathway Ras (e.g. KRAS), BRAF or MEK, which method comprises administering to the subject a therapeutically effective amount of the compound of formula (1).

A method for the diagnosis and treatment of a disease state or condition mediated by ERK1/2, which method comprises (i) screening a patient to determine whether a disease or condition from which the patient is or may be suffering is one which would be susceptible to treatment with a compound having affinity for ERK1/2; and (ii) where it is indicated that the disease or condition from which the patient is thus susceptible, thereafter administering to the patient the compound of formula (1).

Pharmaceutical Formulations

Compound (1) made by the novel process of the invention and novel crystalline forms of compound (1) can be administered to a subject on their own but are more typically presented as a pharmaceutical composition (e.g. formulation).

Thus, in a further embodiment, the present invention provides a pharmaceutical composition comprising the compound of formula (1) and least one pharmaceutically acceptable excipient and optionally other therapeutic or prophylactic agents as described herein.

The invention further provides methods of making a pharmaceutical composition comprising bringing into association (e.g. admixing) the compound of formula (1), at least one said pharmaceutically acceptable excipient and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein refers to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compound (1) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient (e.g. in freeze-dried or other finely divided dried form) in a bottle for subsequent reconstitution using an appropriate diluent.

The pharmaceutical formulation can be prepared by lyophilising the compound of formula (1). Lyophilisation refers to the procedure of freeze-drying a composition. Freeze-drying and lyophilisation are therefore used herein as synonyms. Lyophilization is a method of dehydration in which a solvent-containing substrate is frozen and then subjected to a vacuum so that solvent is removed by sublimation, i.e. direct conversion from the solid frozen state into the gaseous state. Lyophilization typically comprises three stages; a freezing stage; a primary drying stage; and a secondary drying stage. During the freezing stage, the substrate is frozen to a temperature well below its melting point. In the subsequent primary drying stage, the frozen substrate is subjected to a vacuum thereby allowing removal of solvent by sublimation. Most of the solvent is removed from the substrate during this stage. However, a small amount of solvent may remain bound or adsorbed to the substrate at the end of the primary drying stage. In order to remove this residual solvent, the vacuum is maintained but the partially dried substrate is warmed to a temperature at which it is no longer frozen. The residual solvent is thus removed by evaporation.

The freeze-drying procedure may be carried out in a lyophilization apparatus, the construction of which may be entirely conventional. The lyophilization apparatus typically has a chamber in which lyophilization containers containing solution can be placed for freeze-drying. The chamber is typically connected to a vacuum source (e.g. a vacuum pump) to enable the pressure within the chamber to be reduced. The apparatus may also have means for freezing or heating the contents of the chamber.

The pharmaceutical formulation can also be prepared by spray drying the compound of formula (1). Spray drying is a method of producing micron-sized particles in which a solution or suspension of a substrate in a solvent is finely sprayed to form a dispersion of droplets of the solution or suspension and then subjected to heat and/or a partial vacuum so that the solvent is removed by evaporation. The substrate is firstly dissolved or suspended in a suitable solvent, and then the solution is passed through an atomiser or spray nozzle into a drying chamber. A heated gas (for example, air or nitrogen) may also injected into the drying chamber to contact the atomised feed or the drying chamber may be subject to a partial vacuum, in order to initiate evaporation of the solvent. As the solvent evaporates, solid particles of the substrate are formed and can be recovered. The size of the resultant particles in the powder can be altered by selection of the appropriate atomiser or spray nozzle.

The spray drying procedure may be carried out with a spray drier, the construction of which may be entirely conventional. The spray drier typically has an atomizer or spray nozzle that disperses the solution into a fine spray (typically less than 500 μm in diameter). The fine spray is directed into a drying chamber. The drying chamber typically also has an inlet for receiving a heated gas (such as air or nitrogen) and is optionally also connected to a vacuum source (e.g. a vacuum pump) to enable the pressure within the chamber to be reduced. The drying chamber may also have an outlet through which the solid particles formed from evaporation of the solvent from the spray droplets can be collected.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil, sunflower oil, safflower oil, or corn oil), and injectable organic esters such as ethyl oleate. Proper fluidity can be maintained, for example, by the use of coating (or thickening) materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g. tablets, capsules etc.) can be coated or un-coated. Coatings may act either as a protective film (e.g. a polymer, wax or varnish) or as a mechanism for controlling drug release or may serve aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, colon or jejenum.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (1) may be formulated with a carrier and administered in the form of nanoparticles. Nanoparticles increase surface area, assisting the absorption of the compound, and offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions may comprise from approximately 1% (w/w) to approximately 95% active ingredient and from 99% (w/w) to 5% (w/w) of a pharmaceutically acceptable excipient or combination of excipients. More particularly, the compositions may comprise from approximately 20% (w/w) to approximately 90% (w/w) active ingredient and from 80% (w/w) to 10% of a pharmaceutically excipient or combination of excipients.

Pharmaceutical compositions according to the invention may be, for example, in unit dose form, such as in the form of ampoules, vials, suppositories, dragees, tablets or capsules, or pre-filled syringes.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compound of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see Chiou and Riegelman, J. Pharm. Sci., 60, 1281-1300 (1971)) and are useful in increasing dissolution rates and increasing the bioavailability of poorly water-soluble drugs.

The invention also provides solid dosage forms comprising the solid solution described above. Solid dosage forms include tablets, capsules and chewable tablets, or dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads (non-pareils). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped mouldable or waxy material containing the active compound. Solutions of the active compound may also be used for rectal administration.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compound of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The compound of the invention will be administered to a patient in need thereof (for example a human or animal patient) in an amount sufficient to achieve the desired therapeutic effect.

Methods of Treatment

The compound of the formula (1) may be useful in the prophylaxis or treatment of a range of disease states or conditions mediated by ERK1/2. Examples of such disease states and conditions are set out above.

The compound is generally administered to a subject in need of such administration, for example a human or animal patient, particularly a human.

The compound will typically be administered in amounts that are therapeutically or prophylactically useful and which generally are non-toxic. However, in certain situations (for example in the case of life threatening diseases), the benefits of administering a compound of the formula (1) may outweigh the disadvantages of any toxic effects or side effects, in which case it may be considered desirable to administer the compound in amounts that are associated with a degree of toxicity.

The compound may be administered over a prolonged term to maintain beneficial therapeutic effects or may be administered for a short period only. Alternatively it may be administered in a continuous manner or in a manner that provides intermittent dosing (e.g. a pulsatile manner).

A typical daily dose of the compound of formula (1) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (1) and subformulae thereof can be administered on a daily basis or on a repeat basis every 2, or 3, or 4, or 5, or 6, or 7, or 10 or 14, or 21, or 28 days for example.

The compound of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day to obtain the desired therapeutic effect. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one particular dosing schedule, a patient will be given an infusion of a compound of the formula (1) thereof for periods of one hour daily for up to ten days in particular up to five days for one week, and the treatment repeated at a desired interval such as two to four weeks, in particular every three weeks.

The compound of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days, with the pattern repeating during the treatment cycle.

In one dosing schedule, a patient may be given an infusion of a compound of the formula (1) thereof for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has been discovered that ERK1/2 inhibitors can be used as a single agent or in combination with other anticancer agents. For example, it may be beneficial to combine an inhibitor that suppresses ERK signalling with another agent which acts via a different point in the signal transduction cascade or a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compound of the invention can be administered as the sole therapeutic agent or it can be administered in combination therapy with one or more other compounds (or therapies) for treatment of a particular disease state, for example a neoplastic disease such as a cancer as hereinbefore defined. For the treatment of the above conditions, the compound of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compound of the formula (1) include but are not limited to:

Topoisomerase I inhibitors
Antimetabolites
Tubulin targeting agents
DNA binder and topoisomerase II inhibitors
Alkylating Agents
Monoclonal Antibodies
Anti-Hormones
Signal Transduction Inhibitors
Ubiquitin-proteasome pathway Inhibitors
Immunotherapies
Regulators of Cell Death
DNA methyl transferase inhibitors
Cytokines and retinoids
Chromatin targeted therapies
Radiotherapy, and,
Other therapeutic or prophylactic agents.

Particular examples of anti-cancer agents or adjuvants (or salts thereof), include but are not limited to any one or more of the agents selected from groups (i)-(xlviii), and optionally group (xlix) and or (I), below:
(i) Platinum compounds, for example cisplatin (optionally combined with amifostine), carboplatin or oxaliplatin;
(ii) Taxane compounds, for example paclitaxel, paclitaxel protein bound particles (Abraxane™), docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide) or trifluridine (optionally in combination with tipiracil);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);
(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;
(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;
(xi) DNA methyl transferase inhibitors, for example temozolomide, azacytidine, decitabine or guadecitabine (SGI-110);
(xii) Antifolates, for example methotrexate, pemetrexed disodium, or raltitrexed;
(xiii) Cytotoxic antibiotics, for example antinomycin D, bleomycin, mitomycin C, dactinomycin, carminomycin, daunomycin, levamisole, plicamycin, or mithramycin;
(xiv) Tubulin-binding agents, for example combrestatin, colchicines or nocodazole;
(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.
(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;
(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);
(xviii) PKA/B inhibitors and PKB (akt) pathway inhibitors for example AT13148, AZD5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);
(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylamino-ethylamino-17-demethoxygeldanamycin hydrochloride (17-DMAG) e.g. NSC-707545 and Kos-1022, NVP-AUY922 (VER-52296), NVP-BEP800, CNF-2024 (BUB-021 an oral purine), ganetespib (STA-9090), SNX-5422 (SC-102112), or IPI-504 or TAS-116;
(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MED14736 (anti-PD-L1), or tremelimumab (formerly ticilimumab, CP-675,206, anti-CTLA-4);
(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;
(xxii) Aromatase inhibitors and related drugs, such as exemestane, anastrozole, letrazole, testolactone aminoglutethimide, mitotane or vorozole;
(xxiii) Antiandrogens (i.e. androgen receptor antagonists) and related agents for example bicalutamide, nilutamide, flutamide, cyproterone, or ketoconazole;
(xxiv) Hormones and analogues thereof such as medroxyprogesterone, diethylstilbestrol (a.k.a. diethylstilboestrol) or octreotide;
(xxv) Steroids for example dromostanolone propionate, megestrol acetate, nandrolone (decanoate, phenpropionate), fluoxymestrone or gossypol,
(xxvi) Steroidal cytochrome P450 17alpha-hydroxylase-17,20-lyase inhibitor (CYP17), e.g. abiraterone;
(xxvii) Gonadotropin releasing hormone agonists or antagonists (GnRAs) for example abarelix, goserelin acetate, histrelin acetate, leuprolide acetate, triptorelin, buserelin, or deslorelin;
(xxviii) Glucocorticoids, for example prednisone, prednisolone, dexamethasone;
(xxix) Differentiating agents, such as retinoids, rexinoids, vitamin D or retinoic acid and retinoic acid metabolism blocking agents (RAMBA) for example accutane, alitretinoin, bexarotene, or tretinoin;
(xxx) Farnesyltransferase inhibitors for example tipifarnib;
(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;
(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);
(xxxiii) Photodynamic drugs for example porfimer sodium or temoporfin;
(xxxiv) Marine organism-derived anticancer agents such as trabectidin;
(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab,r Iodine tositumomab or alpha radium;
(xxxvi) Telomerase inhibitors for example telomestatin;
(xxxvii) Matrix metalloproteinase inhibitors for example batimastat, marimastat, prinostat or metastat;
(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;
(xxxix) Selective immunoresponse modulators for example thalidomide, or lenalidomide;
(xl) Therapeutic Vaccines such as sipuleucel-T (Provenge) or OncoVex;
(xli) Cytokine-activating agents include Picibanil, Romurtide, Sizofiran, Virulizin, or Thymosin;
(xlii) Arsenic trioxide;
(xliii) Inhibitors of G-protein coupled receptors (GPCR) for example atrasentan;
(xliv) Enzymes such as L-asparaginase, pegaspargase, rasburicase, or pegademase;
(xlv) DNA repair inhibitors such as PARP inhibitors for example, olaparib, velaparib, iniparib, INO-1001, AG-014699, or ONO-2231;
(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;
(xlvii) Immunotherapies such as immune checkpoint inhibitors; cancer vaccines and CAR-T cell therapy;
(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech), HGS-1029/AEG-40826 (HGS/Aegera) or ASTX-660;

(xlix) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate; and
(l) radiotherapy for radical, palliative or prophylactic purposes (or, for adjuvant or neoadjuvant purposes).

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be used in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, particularly 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (1) is administered in combination therapy with one, two, three, four or more other therapeutic agents (particularly one or two, more particularly one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the particular method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. The ratio and the exact dosage and frequency of administration will depend on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of the instant invention. A particular weight ratio for the present compound of formula (1) and another anticancer agent may range from 1/10 to 10/1, more in particular from 1/5 to 5/1, even more in particular from 1/3 to 3/1.

The compound of the invention may also be administered in conjunction with non-chemotherapeutic treatments such as radiotherapy, photodynamic therapy, gene therapy; surgery and controlled diets.

The compound of the present invention may also have therapeutic applications in sensitising tumour cells for radiotherapy and chemotherapy. Hence the compound of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: haematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (1) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

It will be appreciated from the foregoing that, in a further embodiment, the invention provides a combination of the compound of formula (1) and another therapeutic agent, for example another therapeutic agent as defined above.

In another embodiment, the invention provides a pharmaceutical composition comprising the compound of formula (1) together with a pharmaceutically acceptable carrier and one or more therapeutic agent(s) as defined above.

In further embodiments, the invention provides:

A combination as defined herein for use in the treatment of (for use in alleviating or reducing the incidence of) a disease or condition as described herein, in particular cancer.

The use of a combination as defined herein for the manufacture of a medicament for the treatment of (for use in alleviating or reducing the incidence of) a disease or condition as described herein, in particular cancer.

A method of preventing or treating (for use in alleviating or reducing the incidence of) a disease or condition as described herein, in particular cancer, in a subject (e.g. a mammalian subject, such as a human, in need thereof), which method comprises administering to the subject a therapeutically effective amount of a combination as defined herein.

A combination as defined herein for use in for inhibiting the growth of tumour cells (e.g. in a patient).

The use of a combination as defined herein for the manufacture of a medicament for inhibiting growth of tumour cells in a patient.

A method of inhibiting the growth of tumour cells (e.g. in a patient), which method comprises contacting the tumour cells with the compound of formula (1) or a combination as defined herein.

In each of the foregoing embodiments, the compound of formula (1) and one or more other therapeutic agents, at least one of which is an anticancer agent, can be administered simultaneously, separately or sequentially in the treatment of patients suffering from cancer.

In a further embodiment, the invention provides a method for the prophylaxis or treatment of (or alleviating or reducing the incidence of) cancer, which method comprises administering to a patient in combination with radiotherapy or chemotherapy the compound of formula (1).

In another embodiment, the invention provides the compound of formula (1) for use the prophylaxis or treatment of (or alleviating or reducing the incidence of) cancer in combination with radiotherapy or chemotherapy.

EXAMPLES

The invention will now be illustrated, but not limited, by reference to the specific embodiments described in the following examples. Compounds are named using an automated naming package such as AutoNom (MDL) or ChemAxon Structure to Name or are as named by the chemical supplier. In the examples, the following abbreviations are used.

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Abbreviations ca. Approximately
conc. Concentrated
Corr. Corrected
DCM Dichloromethane
DIPEA N,N-Diisopropylethylamine
1,4-DMB 1,4-Dimethoxybenzene
DMF N,N,-Dimethylformamide
$d_6$-DMSO Deuterated dimethylsulfoxide
eq. Equivalents
EtOAc Ethyl acetate
FaSSGF Fasted state simulated gastric fluid
FaSSIF Fasted state simulated intestinal fluid
g gram
GF/F Glass microfibre filter grade
h hours
$^1$H Proton
1-[Bis(dimethylamino)methylene]-1H-1,2,3-triazolo[4,5-b]pyridinium 3-oxide
HATU hexafluorophosphate
HPLC High Performance Liquid Chromatography
Kg Kilogram
L Litre
LC-MS Liquid Chromatography-Mass Spectrometry
M Molar
MeCN Acetonitrile
MeOH Methanol
2-MeTHF 2-Methyltetrahydrofuran
mg milligram
Mins Minutes
mL millilitre
mol Moles
MW Molecular weight
NMP 1-Methyl-2-pyrrolidinone
NMR Nuclear Magnetic Resonance
TFA Trifluoroacetic acid
th Theory
TLC Thin layer chromatography
TPGS D-α-Tocopherol polyethylene glycol 1000 succinate
Uncorr. Uncorrected
UV Ultraviolet
vol Volumes
w/v Weight/volume
w/w Weight/weight
wrt With respect to
wt Weights BINAP, 2,2'-bis(diphenylphosphino)-1,1-binaphthalene; CDI, 1,1'-carbonyldiimidazole; DCE, 1,2-dichloroethane; DCM, Dichloromethane; DIPEA, diisopropylethylamine; DMSO, dimethylsulfoxide; DMF, N,N-dimethylformamide; DMAP, -(dimethylamino)pyridine; EtOAc, ethyl acetate; h, hour; HATU, N,N,N',N'-tetramethyl-O-(7-azabenzotriazol-1-yl)uronium hexafluorophosphate; HBTU, 3-[Bis(dimethylamino)methyliumyl]-3H-benzotriazol-1-oxide hexafluorophosphate; HCl, Hydrochloric acid; HPLC, High pressure liquid chromatography; LC-MS, Liquid chromatography-mass spectrometry; LiHMDS, lithium bis(trimethylsilyl) amide; mins., Minutes; MeCN, acetonitrile; MS, Mass Spectrometry; NBS, N-bromosuccinimide; NMR, Nuclear Magnetic Resonance Spectroscopy; $PdCl_2(dppf)_2$, (1,1'-Bis (diphenylphosphino)-ferrocene)palladium(II) dichloride; $Pd_2(dba)_3$, tris(dibenzylidine acetone)palladium (0); Petrol, petroleum ether fraction with boiling point range 40-60° C.; PyBOP, benzotriazol-1-yloxy)tris(dimethylam ino)phosphonium hexafluorophosphate; RT, room temperature; Sat., Saturated; SCX, solid phase cation exchange resin; SPhos, 2-Dicyclohexylphosphino-2',6'-dimethoxybiphenyl; S-Phos Pd G3, (2-Dicyclohexylphosphino-2',6'-dimethoxybiphenyl) [2-(2'-amino-1,1'-biphenyl)]palladium(II) methanesulfonate; TBDMSCl, tert-butyldimethylsilyl chloride; TBTU, O-(Benzotriazol-1-yl)-N,N,N',N'-tetramethyluronium tetrafluoroborate; TFA, trifluoroacetic acid; THF, Tetrahydrofuran; XPhos, 2-Dicyclohexylphosphino-2',4', 6'-triisopropylbiphenyl; XantPhos, 4,5-Bis(diphenylphosphino)-9,9-dimethylxanthene.

Where quantities are given in weight equivalents (wt) and volume equivalents (vol), 1 vol is equal to 1 mL per gram of the starting material (which is defined of having a weight equivalence value of 1 wt). For example, where 50 mg (0.05 g) of the starting material (defined as having a weight equivalence of 1 wt) are used, an amount of 20 vol is equal to 1 mL (0.05×20=1).

Synthetic Methods

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Parr hydrogenator, a Thales H-cube flow reactor under the conditions stated or under a balloon of hydrogen. Microwave reactions were performed in a CEM Discover and Smithcreator microwave reactor, heating to a constant temperature using variable power microwave irradiation. Normal phase column chromatography was routinely carried out on an automated flash chromatography system such as CombiFlash Companion or CombiFlash RF system using pre-packed silica (230-400 mesh, 40-63 µm) cartridges. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% $NH_3$ in MeOH.

Where a compound is described as a mixture of two diastereoisomers/epimers, the configuration of the stereocentre is not specified and is represented by straight lines.

NMR Data $^1$H NMR spectra were acquired on a Bruker Avance III spectrometer at 400 MHz. Either the central peaks of chloroform-d, dimethylsulfoxide-$d_6$ or an internal standard of tetramethylsilane were used as references. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

EXAMPLE 1

Figure 1:
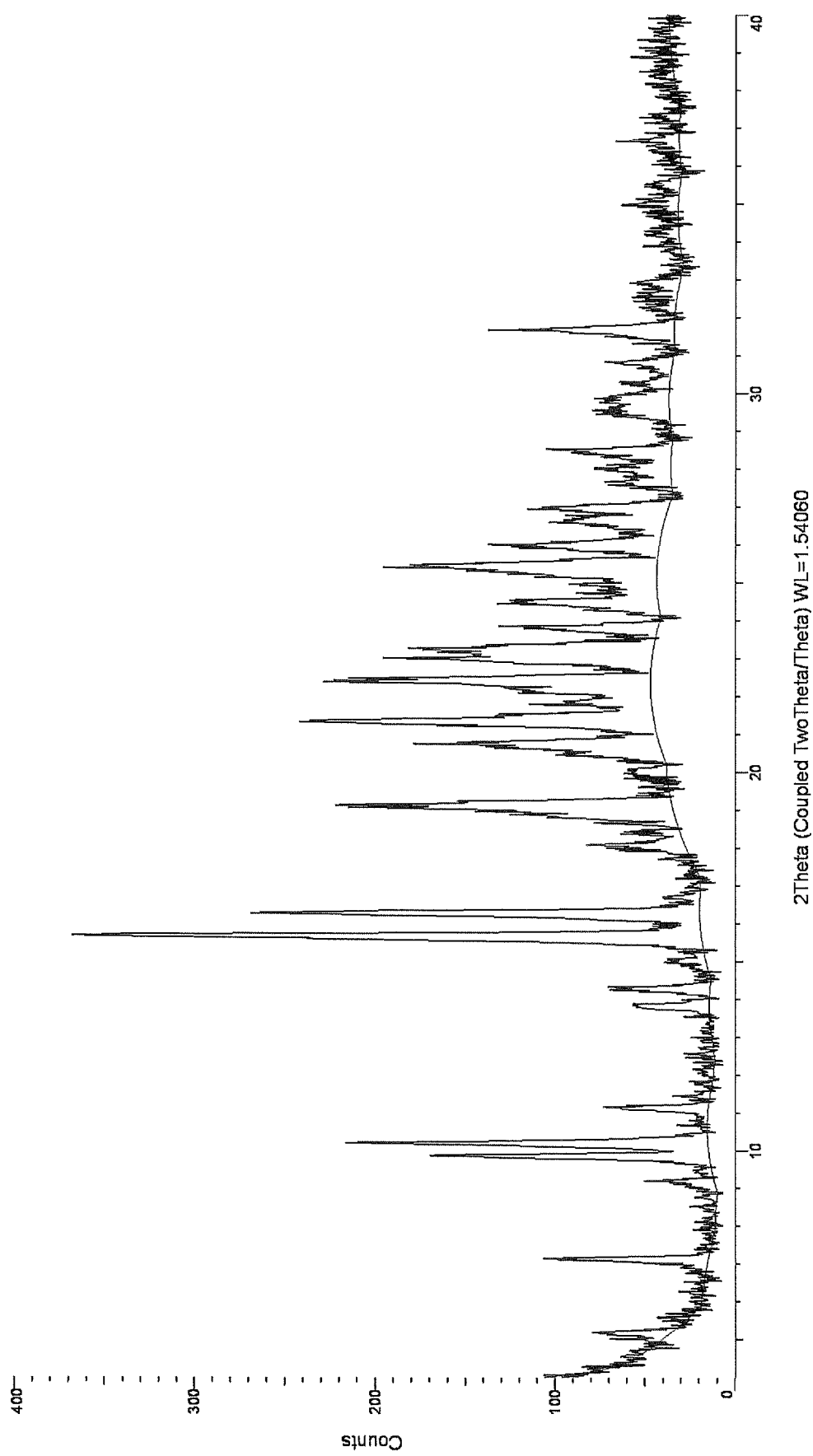
FIG. 1 is an X-ray powder diffractogram of one crystalline form ("Form A") of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

Synthesis of Amorphous (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide Step 1: methyl 5-bromo-2-(bromomethyl)benzoate

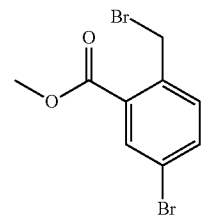

To a 10 L five necked flask fitted with condenser, stirrer bar, $N_2$ inlet and bubbler was added methyl-5-bromo-2-methylbenzoate (500.0 g, 2.18 mol, 1.0 eq.) and N-bromosuccinimide (Fluorochem, 388.5 g, 2.18 mol, 1.0 eq.) to a stirring solution of 1,2-dichloroethane (1.9 L). The mixture was heated to 90° C. (oil bath). Azobisisobutyronitrile (5.0 g, 0.03 mol, 0.014 eq.) was dissolved into DCE (100 mL) and 20 mL was added into a dropping funnel. This was added slowly when the reaction mixture reached 85° C.

When the violent reflux and foaming ceased, the remaining 80 mL was added in one portion to the reaction mixture and left to stir at 90° C. for 1 hr. NMR showed the reaction to be complete with around 11% of starting material still remaining. The reaction mixture was then cooled to room temperature using cardice in the oil bath and once the internal temperature had fallen to −30° C., the reaction mixture was quenched with water (2.0 L). After 5 minutes, two identical reaction mixtures were combined, transferred to a separating funnel and the organic layer was collected. The aqueous layer was extracted again using DCM (2×2.0 L). All the organic layers were combined and washed with water (2 L) and brine (2 L), dried with MgSO$_4$, filtered and concentrated under vacuo to give an orange liquid (1.397 kg, 104%, from 2×500 g runs).

Step 2—tert-butyl (2R)-2-(6-bromo-1-oxo-2,3-dihydro-1H-isoindol-2-yl)propanoate

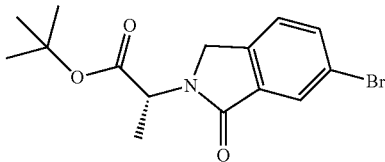 [SMILES: C[C@H](C(=O)OC(C)(C)C)N1Cc2ccc(Br)cc2C1=O]

To a 10 L five necked flask fitted with condenser, stirrer bar, N$_2$ inlet and bubbler was added methyl 5-bromo-2-(bromomethyl)benzoate (from step 1) (660 g, 2.14 mol, 1.0 eq), t-butyl (2R)-2-aminopropanoate.HCl (467 g, 2.57 mol, 1.2 eq) and diisopropylethylamine (1.0 L, 6.42 mol, 3.0 eq., d=0.742) to a stirred solution of THF (5.0 L). The mixture was heated to 80° C. in an oil bath overnight. The reaction mixture was then cooled to room temperature using cardice and then two identical reaction mixtures were poured into a large separating funnel. A saturated aqueous solution of NaHCO$_3$ (5.6 L) was added and the mixture was stirred for 5 minutes. The organic layer was collected and the aqueous phase was extracted using ethyl acetate (2×4 L). The organic phases were combined and washed with brine (5.6 L) and stirred for 3 minutes, dried over MgSO$_4$, filtered and concentrated under vacuum to give an orange-brown residual sticky solid which was put in a vacuum oven at 40° C. overnight. The solid (1.4 kg) was slurried in petroleum ether 40-60 (2.5 L) and stirred vigorously overnight before being filtered and washed with petroleum ether, 2×300 mL) to give a yellow solid (480 g).

Step 3: tert-butyl (2R)-2-[1-oxo-6-(4,4,5,5-tetramethyl-1,3,2-dioxaborolan-2-yl)-2,3-dihydro-1H-isoindol-2-yl]propanoate

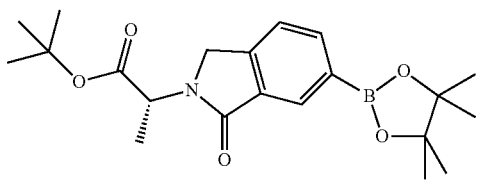 [SMILES: C[C@H](C(=O)OC(C)(C)C)N1Cc2ccc(B3OC(C)(C)C(C)(C)O3)cc2C1=O]

To a 10 L five necked flask fitted with overhead stirrer, condenser, thermoprobe and N$_2$ inlet and bubbler was added tert-butyl (2R)-2-(6-bromo-1-oxo-2,3-dihydro-1H-isoindol-2-yl)propanoate (from step 2) (500 g, 1.469 mol, 1.0 eq), bis(pinacolato)diboron (446.3 g, 1.764 mol, 1.2 eq) and anhydrous potassium acetate (433.9 g, 4.409 mol, 3 eq) to a stirred solution of dioxane (4 L). This was then de-gassed with N$_2$ for 30 minutes before Pd(dppf)Cl$_2$ (21.5 g, 0.029 mol, 0.02 eq) was added and the reaction mixture was further de-gassed for 10 minutes and then heated to 90° C. in an oil bath. This was allowed to stir overnight (NOTE: after 2-3 hours at 90° C., the reaction exotherms from 88° C. to 104° C. with large refluxing and the solution turning from an orange-red solution to a dark brown for ~30 mins before cooling back to 90° C.). The reactions were cooled to room temperature using cardice before being combined and filtered through a celite pad (4 L sinter, ~2 inch thick pad). The pad was washed with dioxane (1 L) until all the colour had been washed through.

Step 4: tert-butyl (2R)-2-[6-(2,5-dichloropyrimidin-4-yl)-1-oxo-2,3-dihydro-1H-isoindolin-2-yl]propanoate

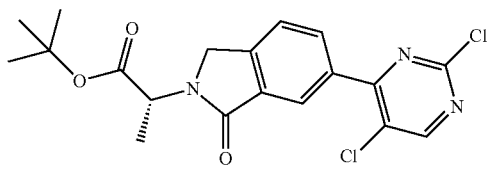 [SMILES: C[C@H](C(=O)OC(C)(C)C)N1Cc2ccc(-c3nc(Cl)ncc3Cl)cc2C1=O]

The solution from Step 3 was then halved and each half placed into a five-necked flask fitted the same as the previous step. To this five necked flask was added 2,4,5-trichloropyrimidine (404.4 g, 252.8 mL, 2.205 mol, 1.5 eq, D=1.6), potassium carbonate (609.4 g, 4.409 mol, 3 eq) and then de-gassed with N$_2$ for 30 minutes before Pd(dppf)Cl$_2$ (21.5 g, 0.029 mol, 0.02 eq) was added and further de-gassed for 10 minutes. The reaction mixture was heated to 65° C. in an oil bath and then water (500 mL) was added via a dropping funnel over 5 minutes (Note: exotherm from 62° C. to 72° C. a few minutes after initial addition of water). The reaction was left overnight. The reactions were cooled to room temperature using cardice and filtered through a celite pad (4 L sinter, ~3 inch thick pad), washing the pad with DCM (2 L). The filtrate was then concentrated to almost dryness to give a black-brown tar crude material (1909 g).

The crude material was split into two and dry loaded upon a silica column and eluted with 6×4 L of 40% ethyl acetate/petrol. (Note: all fractions were mixed so combined and concentrated to almost dryness—TLC of product in 30% ethyl acetate/petrol Rf=~0.5). The remaining brown mixture was cooled to room temperature and petrol (4 L) added and stirred on the rotary for 2 hours to crystallise out the product. This was filtered and the cake was washed with petrol (2×2 L) to yield a white solid (548 g).

Alternatively, tert-butyl (2R)-2-[6-(2,5-dichloropyrimidin-4-yl)-1-oxo-2,3-dihydro-1H-isoindolin-2-yl]propanoate (Intermediate compound (4)) can be prepared as described in PCT/IB2016/001507 (International publication number WO2017/068412)—see Preparations 76, 89 and 94 therein.

Amorphous (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide (Compound 1) was synthesised from tert-butyl (2R)-2-[6-(2,5-dichloropyrimidin-4-yl)-1-oxo-2,3-dihydro- 1H-isoindolin-2-yl]propanoate (from Step 4) in accordance with the synthetic scheme shown below:

Step 5: (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide

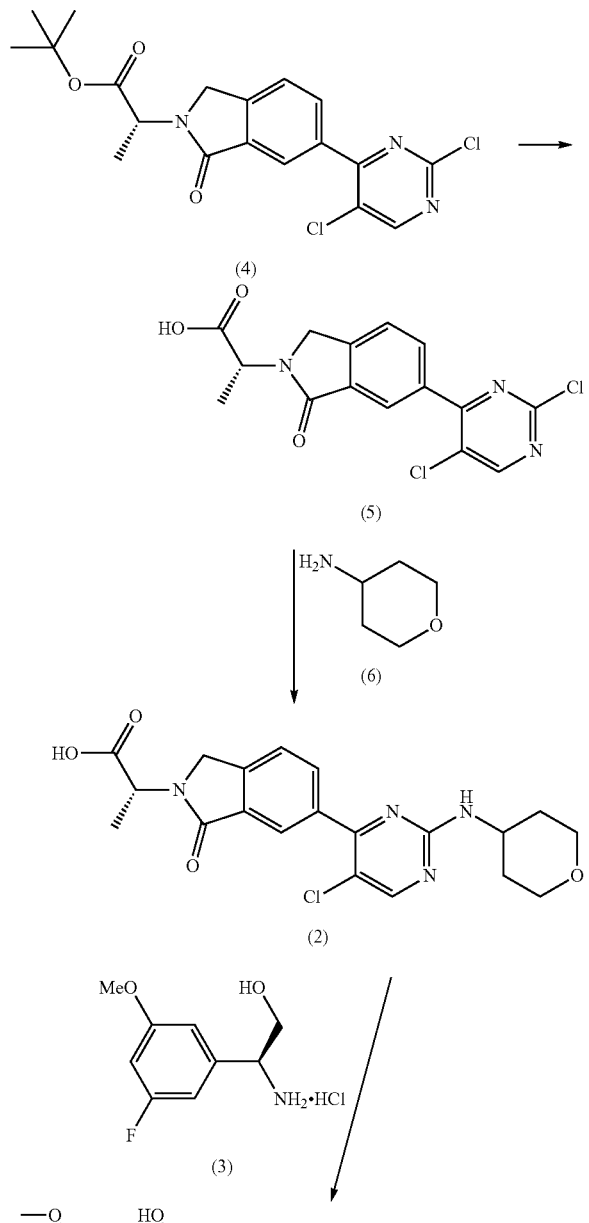

Stage 1: Boc-Deprotection of (4)

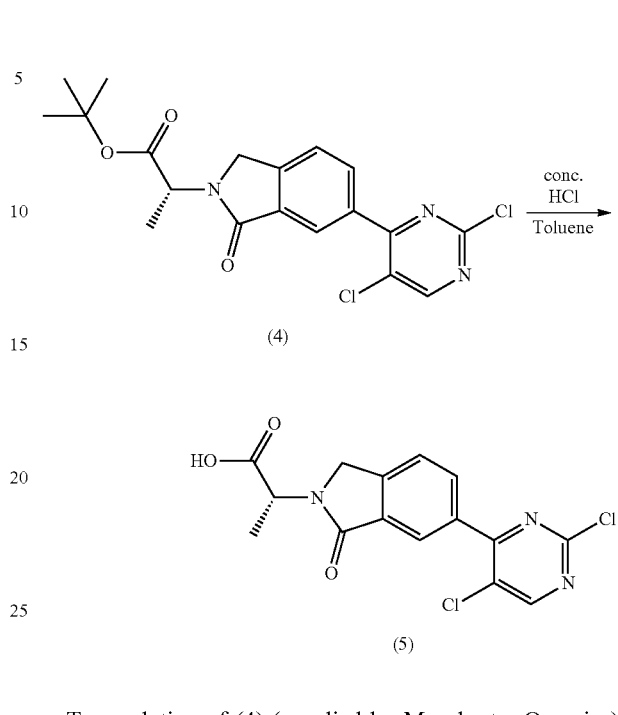

To a solution of (4) (supplied by Manchester Organics) (1.0 wt) in toluene (13 vol) at 15 to 25° C. was added concentrated hydrochloric acid (1 vol) followed by a line rinse of toluene (1 vol). The mixture was heated to 35 to 40° C. and stirred at this temperature until reaction completion was reached (pass criterion: 2.0% area of (4), expected reaction time 16 to 24 hours). The suspension was concentrated under reduced pressure at up to 50° C. until a wet solid was obtained. Toluene (3×10 vol) was charged with concentration under reduced pressure at up to 50° C. to give a wet solid after each successive charge. Toluene (4 vol) was charged and the suspension was rotated on the rotary evaporator at atmospheric pressure at up to 50° C. for 10 to 20 minutes. The flask was removed from the rotary evaporator and the contents were aged for at least 1 h at 15 to 25° C. The solids were collected by filtration, washed with toluene (2×2 vol) and pulled dry under nitrogen until the toluene content was 6.0% w/w and the water content was ≤2.0% w/w. Intermediate (5) was isolated as an off-white to pale beige solid (74 to 95% th, 64 to 82% w/w).

Stage 2: Intermediate (5) Coupling with 4-aminotetrahydropyran

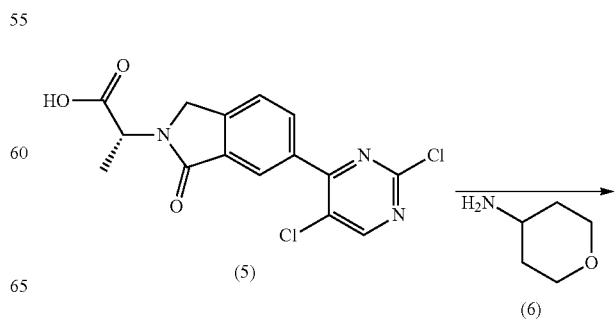

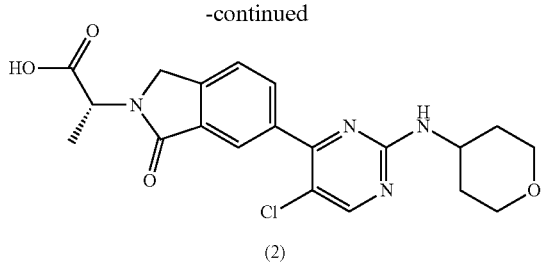

(2)

To a solution of (5) (1.0 wt corrected, 1.0 mol eq) in 1-methyl-2-pyrrolidinone (NMP) (9.5 vol) at 15 to 25° C. was added potassium carbonate (0.86 wt, 2.2 mol eq), followed by 4-aminotetrahydropyran (6) (0.4 vol, 1.3 mol eq) at 15 to 40° C. and a line rinse of NMP (0.5 vol). The mixture was heated to 80 to 95° C. and stirred at this temperature until reaction completion was reached (pass criterion: 1.0 mol % Intermediate (5), reaction time 4 to 6 hours). The mixture was cooled to 15 to 25° C. and 3M hydrochloric acid (10 vol) was charged, maintaining the temperature between 15 and 30° C. Dichloromethane (DCM) (10 vol) was added and the phases were separated. The acidic aqueous phase was back-extracted with DCM (5 vol) and the combined organic phases were washed with purified water (8×10 vol) until the NMP content was controlled to 15.0% w/w. The organic phase was washed with 13% w/w NaCl solution (10 vol), treated with activated charcoal (0.3 wt) and dried over magnesium sulphate (1.0 wt). The mixture was filtered to remove the drying agent, washed with DCM (2×2 vol) and the combined filtrates concentrated under reduced pressure at up to 35° C. to yield (2) as a light brown foam (74 to 90% th, 88 to 107% w/w).

Stage 3: Preparation of Compound 1

To a solution of (2) (1.0 wt, 1.0 mol eq) in DCM (12.5 vol) was added amine (3) (0.68 wt, 1.27 mol eq). The suspension was cooled to 10 to 15° C. and DIPEA (1.67 vol, 4.0 mol eq) was charged. The resulting solution was stirred for 5 to 10 minutes prior to the portion wise addition of HATU (1.15 wt, 1.27 mol eq), maintaining the reaction temperature <25° C. The mixture was stirred at 15 to 25° C. until deemed complete by HPLC (<0.5% area (2), typically 1 h). Upon completion the reaction was concentrated under reduced pressure at up to 38° C. to give a thick, mobile orange oil. The residue was dissolved in EtOAc (10 vol) and washed with purified water (10 vol), 25% w/w ammonium chloride solution (2×10 vol), 8% w/w NaHCO$_3$ solution (2×10 vol) and 13% w/w NaCl solution (6×10 vol), then dried over MgSO$_4$ (1.0 wt). The solid was removed by filtration and the filter cake washed with ethyl acetate (2×2 vol). The filtrates were concentrated on a rotary evaporator at up to 40° C. to give crude Compound 1 as a pale yellow foam. Crude Compound 1 was purified by dry flash chromatography.

Full conversion of (2) to Compound 1 was also observed when subjected to the above conditions but wherein 1-ethyl-3-(3-dimethylaminopropyl)carbodiimide (EDCI) was used as the coupling agent instead of HATU, 4-dimethylamino-pyridine (4-DMAP) was used as the base instead of DIPEA and dimethylformamide (DMF) was used as a solvent instead of DCM.

Chromatographic Procedure:

Silica (20 wts) was charged to the dry flash column and the silica was washed and packed by eluting through ethyl acetate (2×20 vol typical). The crude Compound 1 (1 wt uncorrected) was dissolved in DCM (4 vol) and carefully loaded onto the column. The column was then eluted as follows:

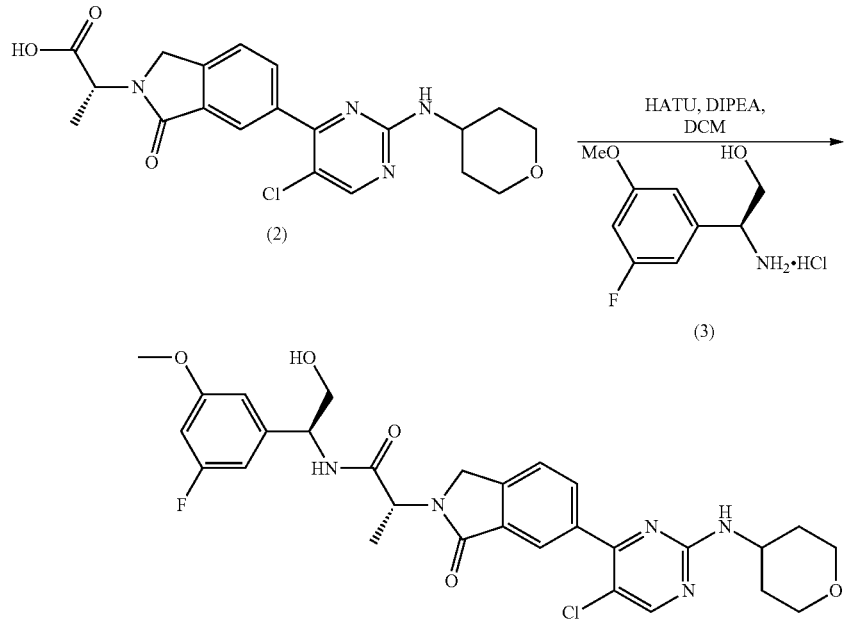

Compound 1

| | | |
|---|---|---|
| Neat EtOAc | 40 × 20 vol | F1-240 |
| 1% MeOH in EtOAc | 10 × 20 vol | F41-50 |
| 5 to 10% MeOH in EtOAc | 3 × 20 vol | F51-53 column flush |

All of the collected fractions were analyzed by HPLC and the product typically eluted in fractions 12 through to 45.

Only those fractions which appeared to be the cleanest and most intense by TLC (e.g. fractions 15 to 25 in the above example range of product elution) were grouped together in the absence of HPLC data. The outer product containing fractions were analysed by HPLC to determine if these were of suitable purity for combining with the main product fractions. Once all of the fractions had been combined and concentrated either to a foam or low volume, the product was diluted with ethyl acetate (e.g. 10 vol), stirred to give a solution and then clarified through glass fibre filter paper. The filtrates were then concentrated to give amorphous Compound 1 as an off-white to pale yellow foam (65 to 85% th, 91 to 119% w/w).

EXAMPLE 2

Preparation of the Amorphous Salts of Compound 1

Stock solutions of the various counter-ions were prepared in 2-propanol. The relevant stock solution (500 μl, 10 vol) was charged to a solution of compound 1 (as prepared according to Example 1) in isopropyl acetate (2.5 ml, 50 vol) and stirred. Solids that failed to crystallise or gave faint precipitates were cooled, concentrated by evaporation or further treated with t-butylmethylether (TBME).

The solids were isolated by filtration, dried under a stream of nitrogen for 96 h, off-loaded and analysed by $^1$H NMR and XRPD (see the following table).

Figure 6:
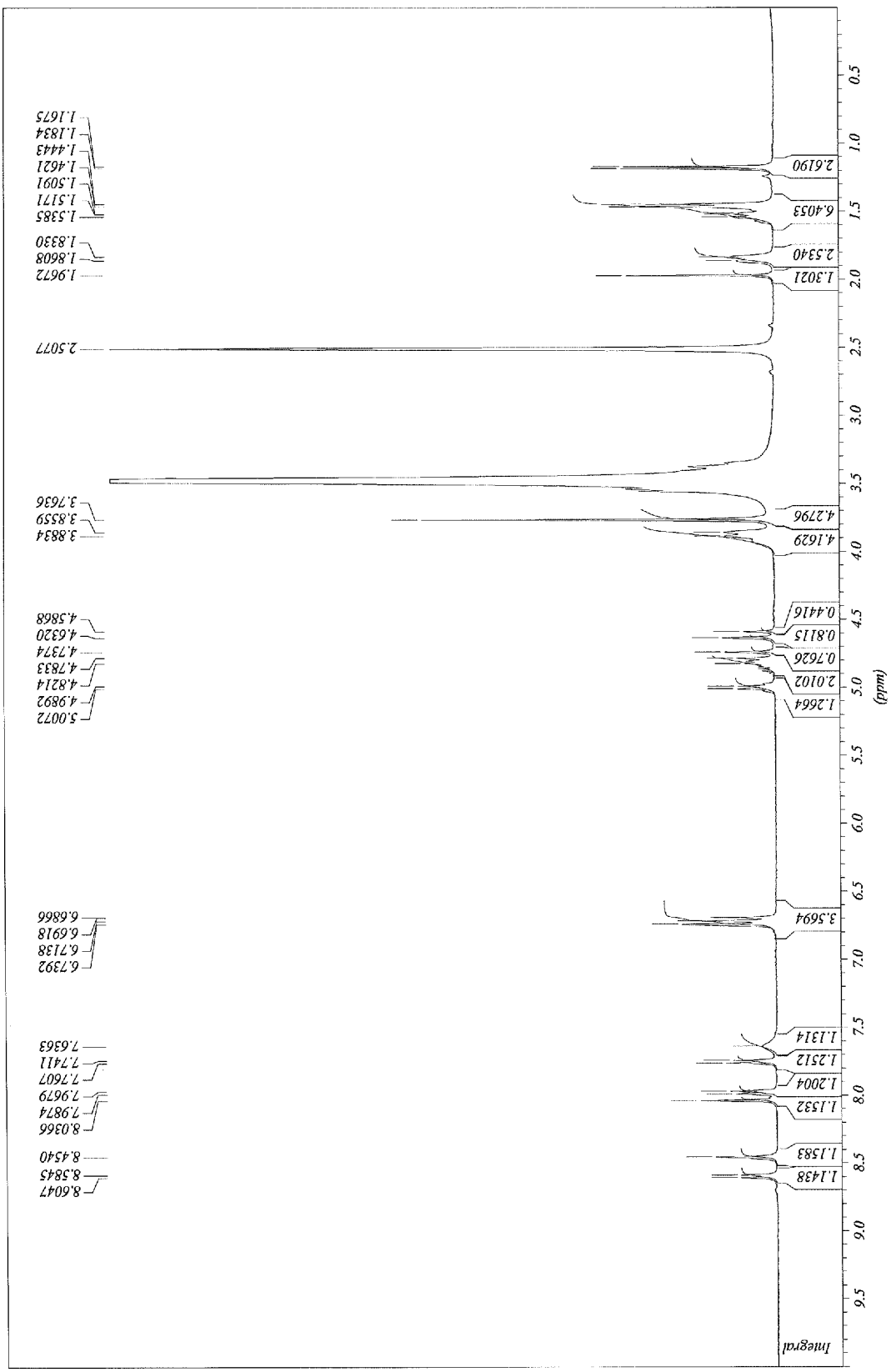
FIG. 6 shows the $^1$H-NMR spectrum of the amorphous hydrochloride salt of the compound of formula (1) obtained in Example 2.
Figure 7:
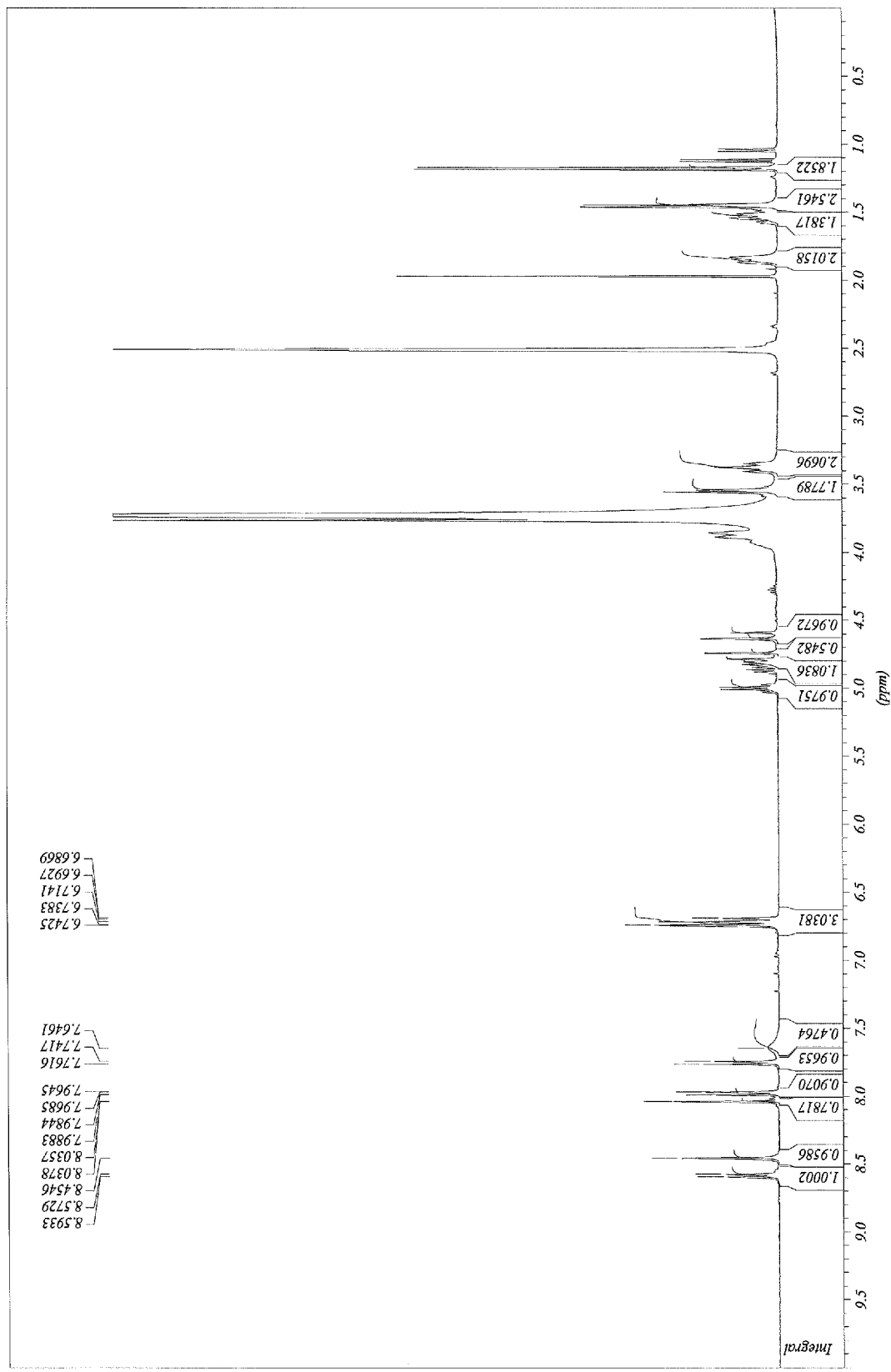
FIG. 7 shows the $^1$H-NMR spectrum of the amorphous sulphate salt of the compound of formula (1) obtained in Example 2.
Figure 8:
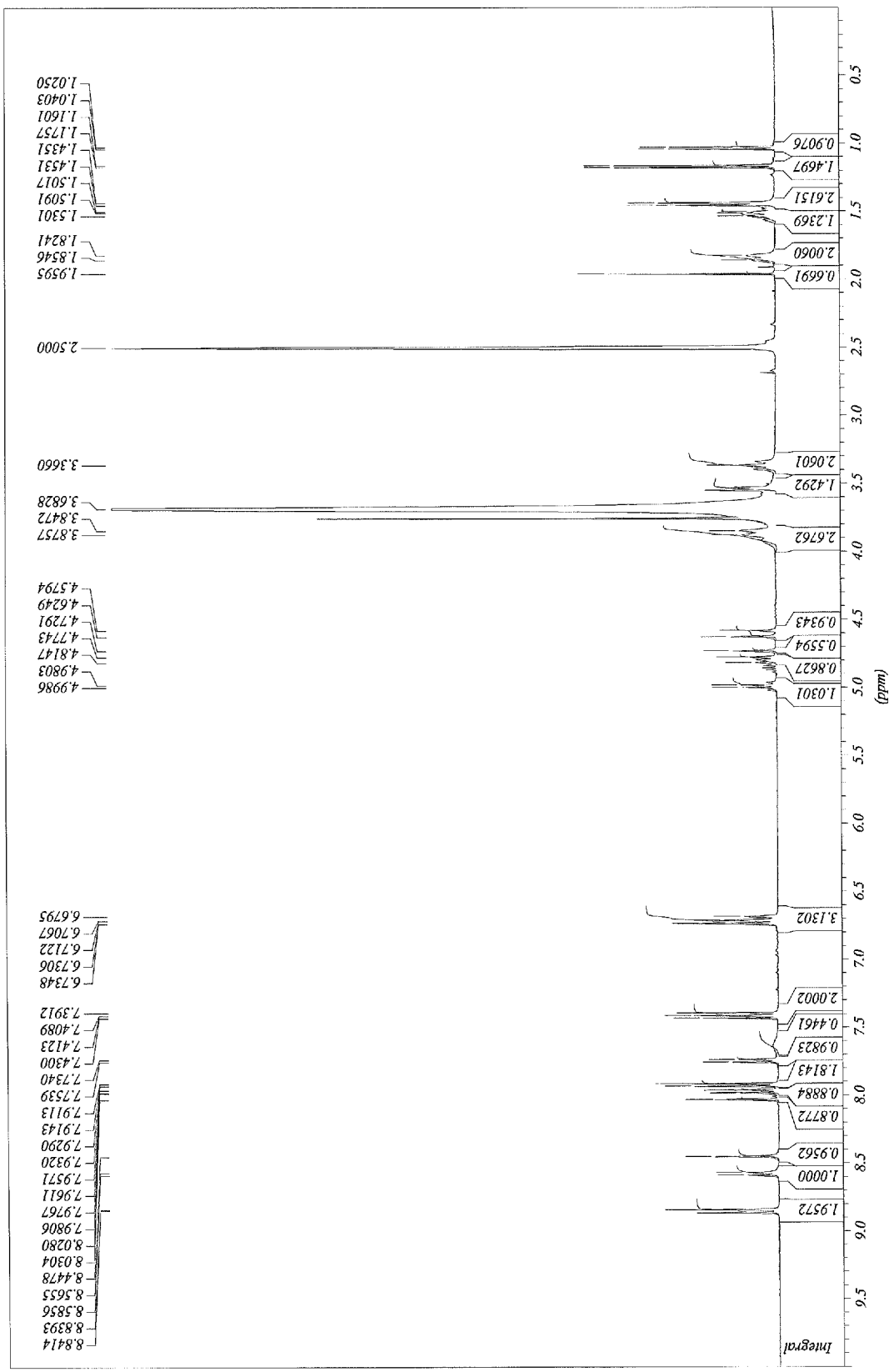
FIG. 8 shows the $^1$H-NMR spectrum of the amorphous napadisilate salt of the compound of formula (1) obtained in Example 2.
Figure 9:
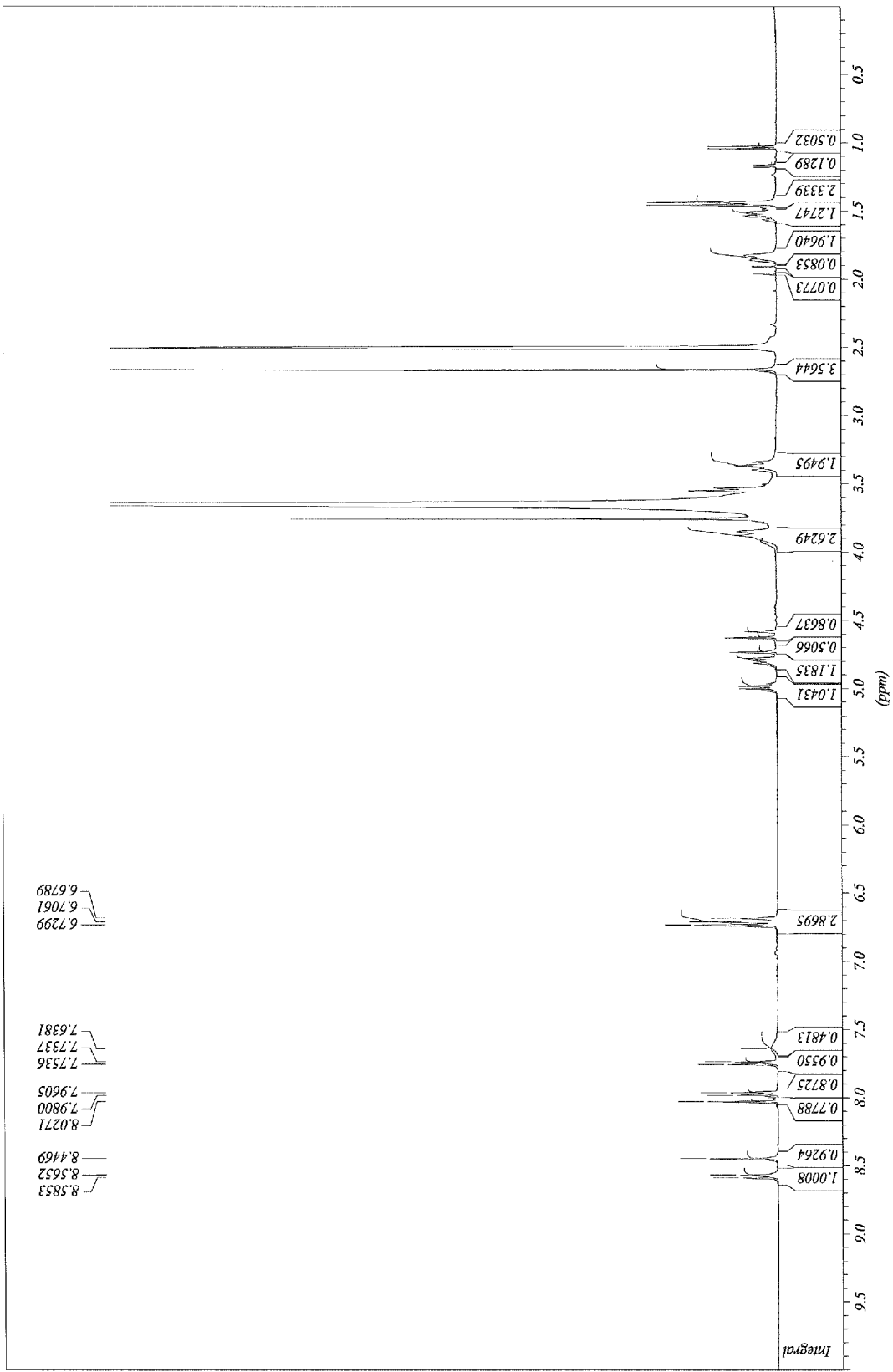
FIG. 9 shows the $^1$H-NMR spectrum of the amorphous edisylate salt of the compound of formula (1) obtained in Example 2.
Figure 10:
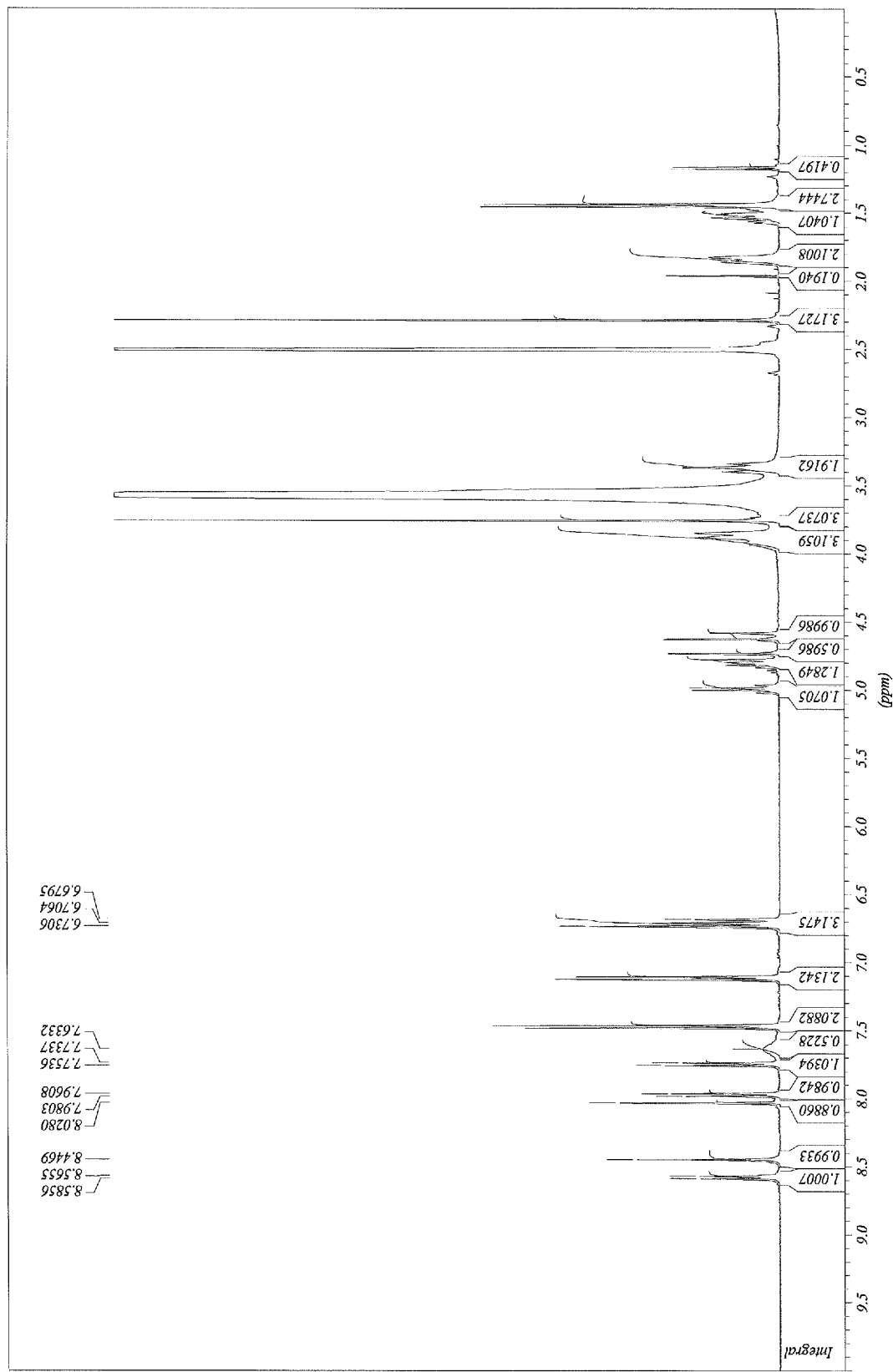
FIG. 10 shows the $^1$H-NMR spectrum of the amorphous tosylate salt of the compound of formula (1) obtained in Example 2.
Figure 11:
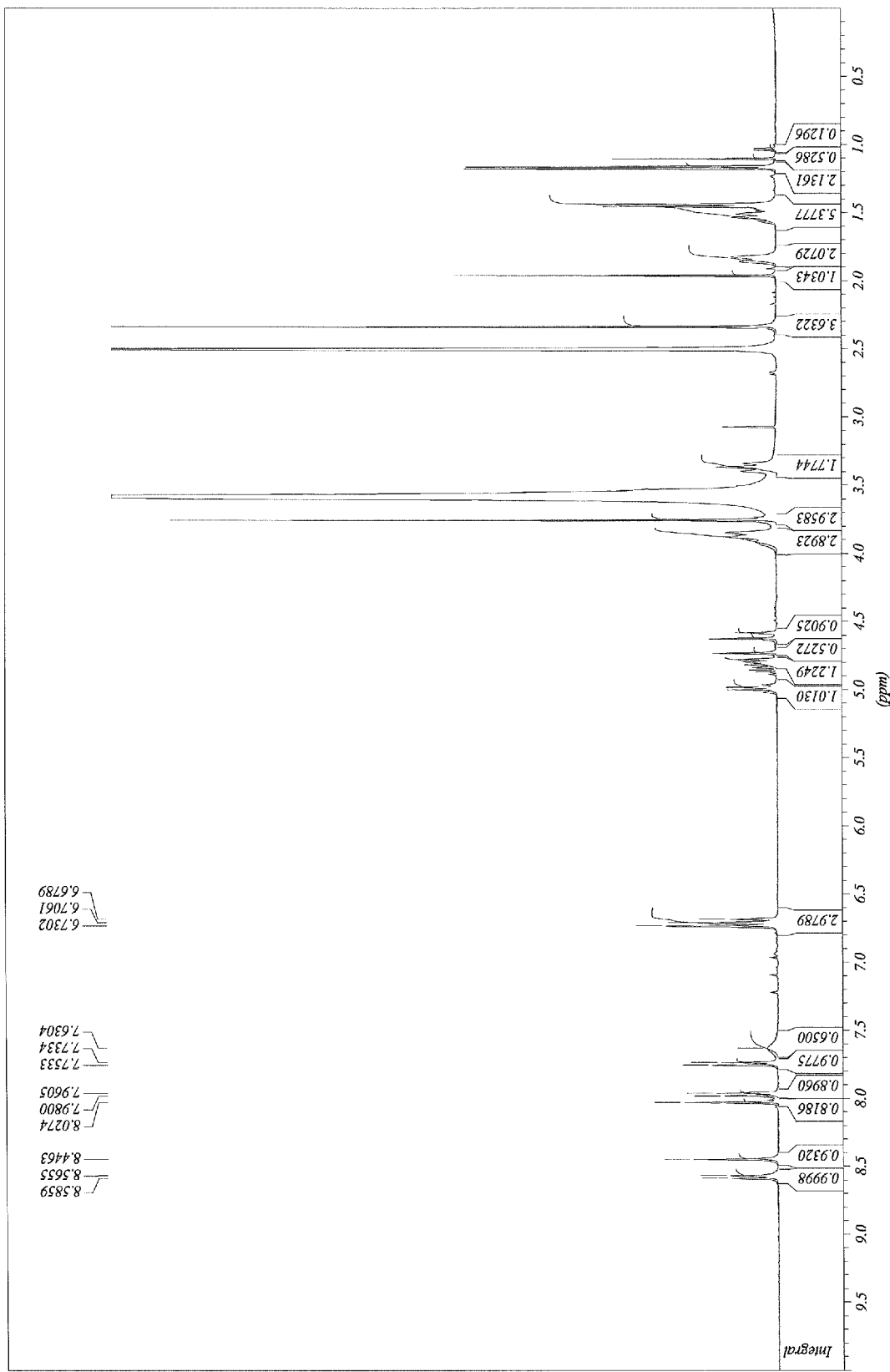
FIG. 11 shows the $^1$H-NMR spectrum of the amorphous mesylate salt of the compound of formula (1) obtained in Example 2.
Figure 12:
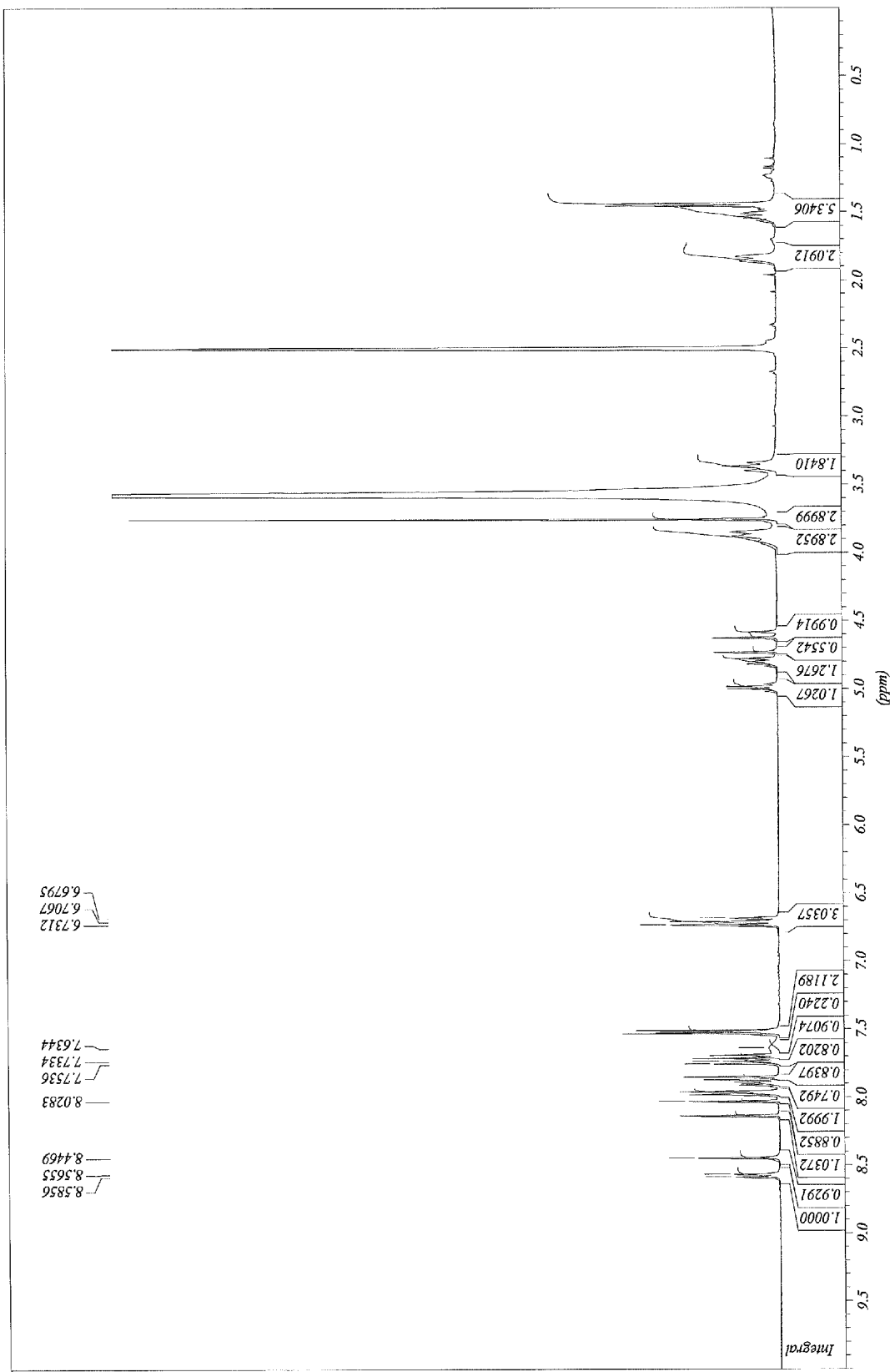
FIG. 12 shows the $^1$H-NMR spectrum of the amorphous napsylate salt of the compound of formula (1) obtained in Example 2.
Figure 13:
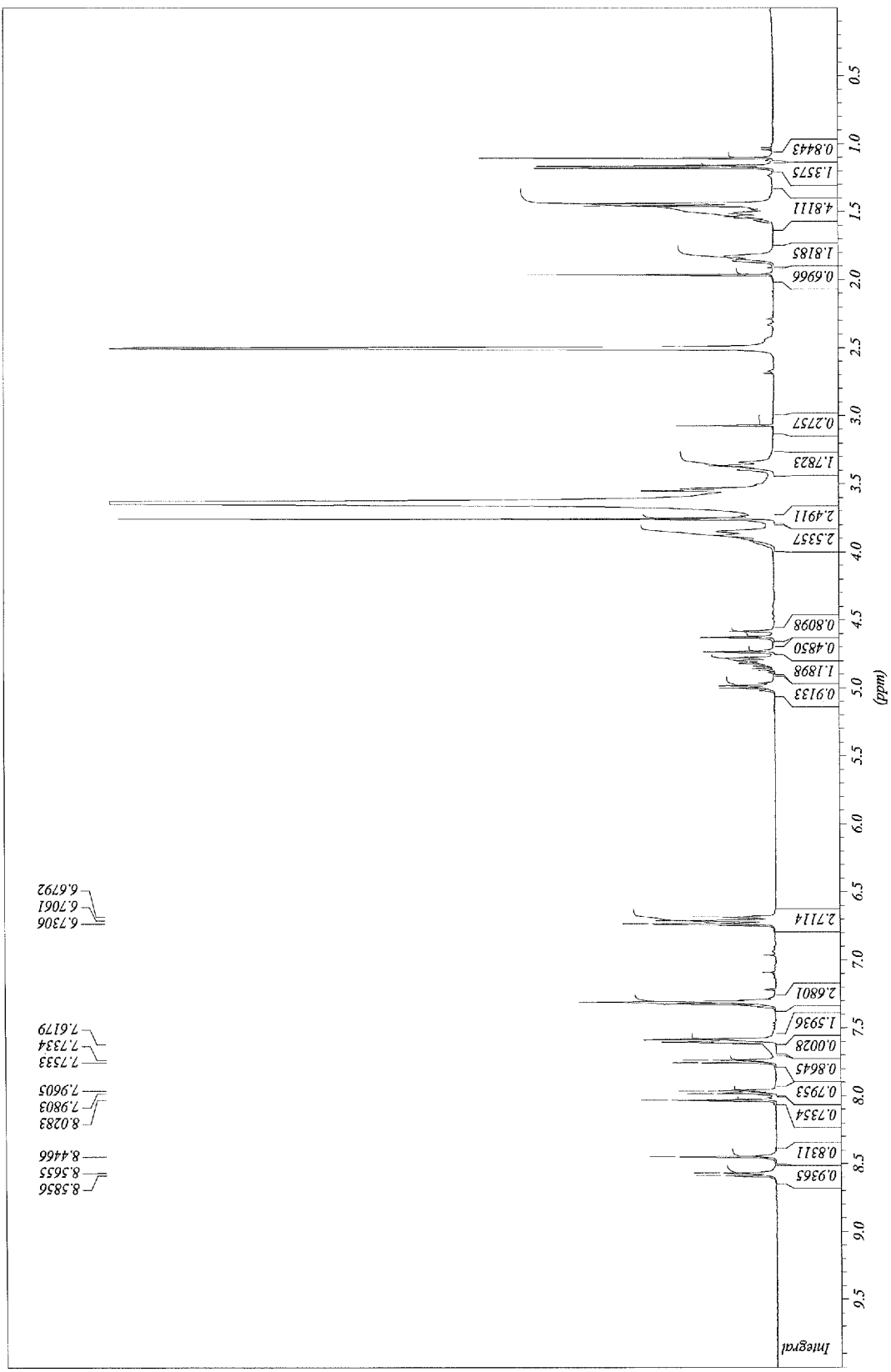
FIG. 13 shows the $^1$H-NMR spectrum of the amorphous besylate salt of the compound of formula (1) obtained in Example 2.
Figure 14:
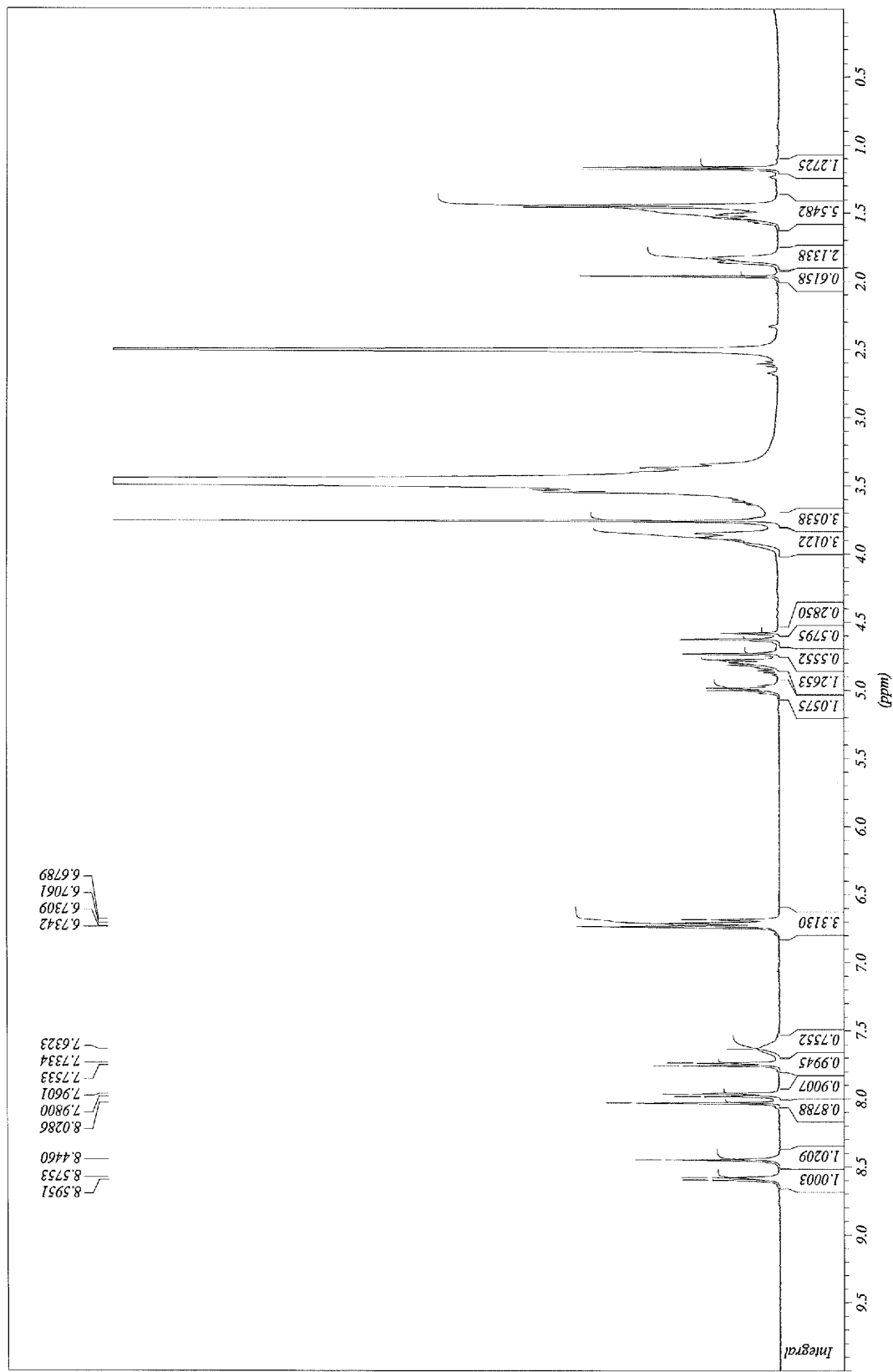
FIG. 14 shows the $^1$H-NMR spectrum of the amorphous isethionate salt of the compound of formula (1) obtained in Example 2.
Figure 15:
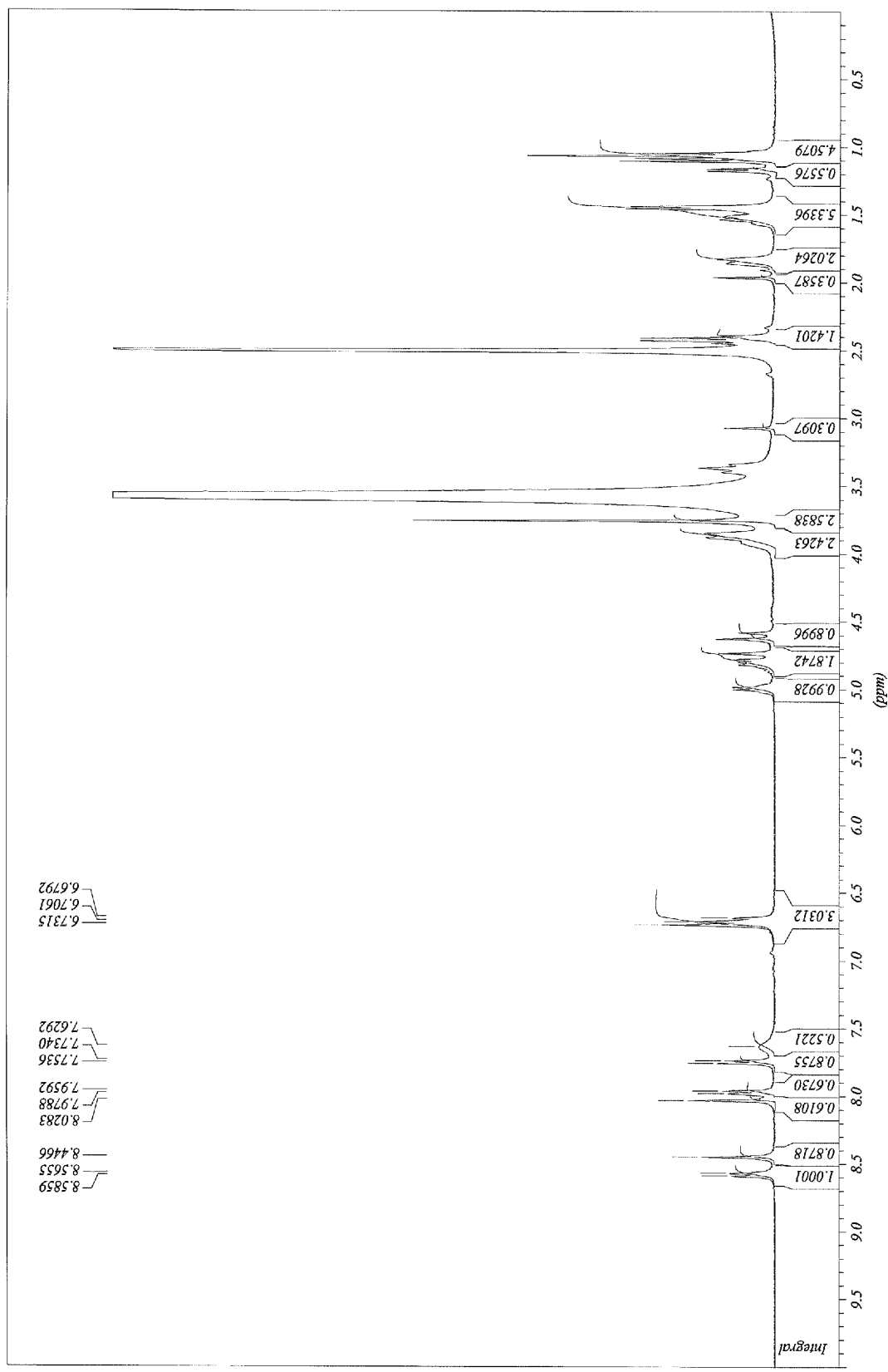
FIG. 15 shows the $^1$H-NMR spectrum of the amorphous esylate salt of the compound of formula (1) obtained in Example 2.
Figure 16:
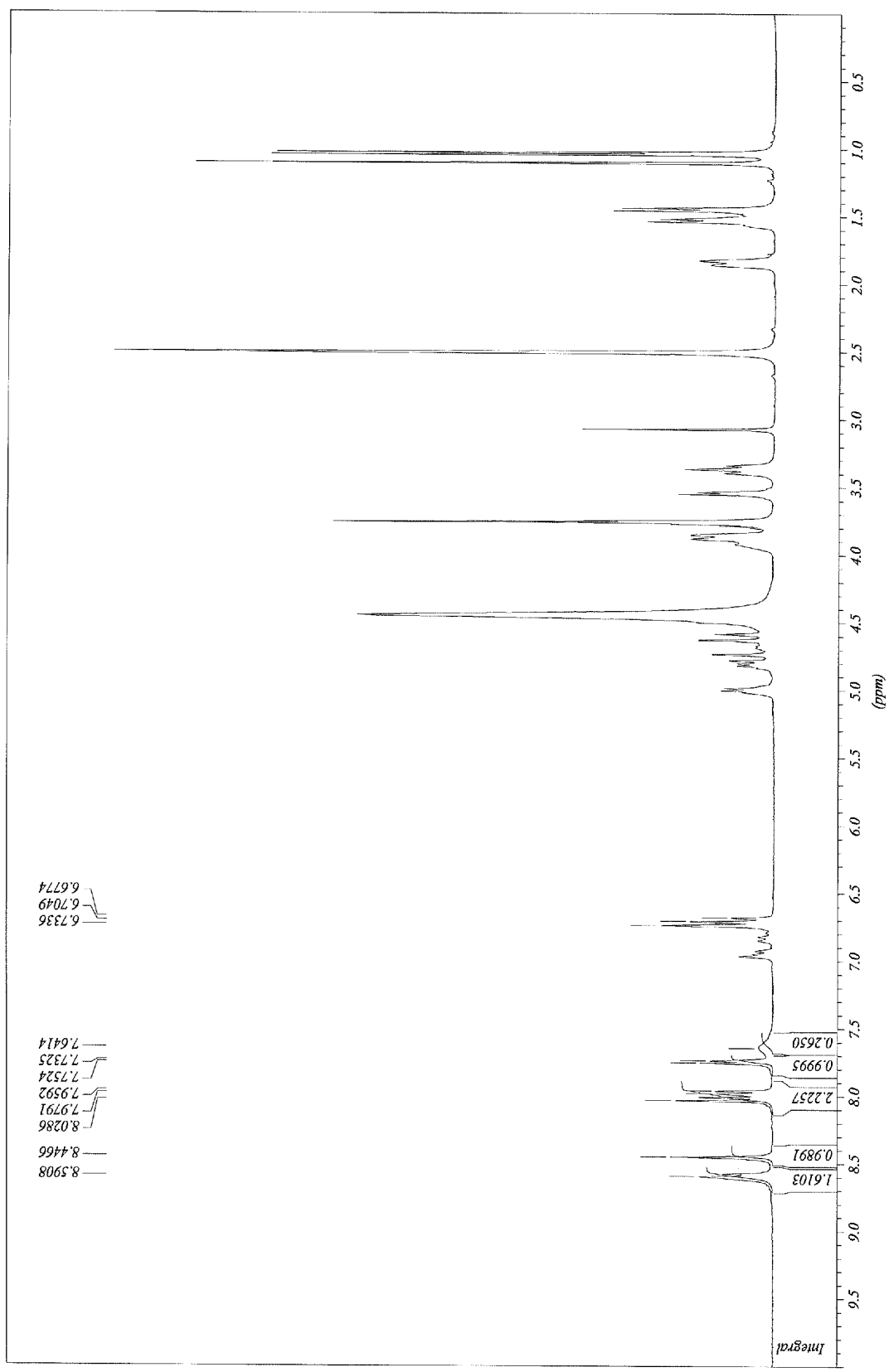
FIG. 16 shows the $^1$H-NMR spectrum of the amorphous hydrobromide salt of the compound of formula (1) obtained in Example 2.

| Acid Counter-ion | Counter-ion Stoichiometry | Common usage salt name | Compound 1: Counter-ion stoichiometry as determined by $^1$H NMR ($^1$H NMR Spectrum) | XRPD Pattern |
|---|---|---|---|---|
| Non-ionised form | N/A | Free Based | N/A | Amorphous |
| 4M Hydrochloric acid (soln. 1,4-dioxane, 99%) | 1 | Hydrochloride | (See FIG. 6) | Amorphous |
| Sulphuric acid (95%) | 2 | Sulphate | (See FIG. 7) | Amorphous |
| Naphthalene-1,5-disulfonic acid tetrahydrate (97%) | 1 | Napadisilate | 1 to 1 (See FIG. 8) | Amorphous |
| Ethane-1,2-disulfonic acid trihydrate (98%) | 1 | Edisylate | 1 to 1 (See FIG. 9) | Amorphous |
| 4-Toluenesulfonic acid monohydrate | 1 | Tosylate | 1 to 1 (See FIG. 10) | Amorphous |
| Methanesulphonic acid (99.5%) | 1 | Mesylate | 1 to 1 (See FIG. 11) | Amorphous |
| Naphthalene-2-sulfonic acid monohydrate (99%) | 1 | Napsylate | 1 to 1 (See FIG. 12) | Amorphous |
| Benzenesulphonic acid (90%) | 1 | Besylate | 1 to 1 (See FIG. 13) | Amorphous |
| 2-Hydroxyethane sulfonic acid sodium salt (98%) | 1 | Isethionate | (See FIG. 14) | Amorphous |
| Ethane sulfonic acid (95%) | 1 | Esylate | 1 to 1 (See FIG. 15) | Amorphous |
| Hydrobromic acid (99%), (48% in water) | 1 | Hydrobromide | (See FIG. 16) | Amorphous |

EXAMPLE 3

Preparation of Crystalline Forms of Compound 1

Example 3A—Preparation of Crystalline Form A

The hydrochloride salt of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide (as prepared in Example 2) was suspended in purified water (35 volumes) at 70° C. for a period of 96 hours. The solid was isolated by filtration, dried under a stream of nitrogen for 96 h, off-loaded and analysed by XRPD (see FIG. 1).

Example 3B—Preparation of Crystalline Form B (Method I)

The hydrochloride salt of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide (as prepared in Example 2) was suspended in purified water (2 ml, 20 vol) at 18 to 23° C. The solutions were stirred at 45 to 50° C. for 20 h. The temperature was then lowered to 30 to 35° C. and the solution stirred for a further 96 h. The XRPD of the solid obtained is shown was consistent with the XRPD pattern of FIG. 2.

Example 3C—Preparation of Crystalline Form B (Method II)

The hydrochloride salt of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide (as prepared in Example 2) was suspended in purified water (20 vol) and the mixture was stirred at 40° C. under nitrogen for 20 h. 2-Propanol (7.6 vol) was charged and the mixture was stirred at 40° C. for 20 h. Progress of the conversion was monitored by XRPD. The XRPD of the solid obtained is shown was consistent with the XRPD pattern of FIG. 2.

Example 3D—Preparation of Crystalline Form B (Method III)

(2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide (as prepared in Example 1) (100 mg, 1.0 wt.) was charged into a vessel, followed by the either ethyl acetate or toluene (15 vol) and tert-butylmethylether (15 vol). The suspension was stirred for 7 days at 30° C. After this time the product was isolated by filtration, washed with recycled maturation solvent, dried under a stream of nitrogen at 18-23° C. and analysed by XRPD for evidence of crystallisation. The XRPD pattern of the solid obtained was consistent with the XRPD pattern of FIG. 2.

EXAMPLE 4

Further Characterisation of the Crystalline Form B of Compound 1

The crystalline Form B of Compound 1 obtained in Examples 3B, 3C and 3D was studied using X-Ray Powder Diffraction, Differential Scanning Calorimetry, Thermogravimetric Analysis and Dynamic Vapour Sorption.

Example 4A—X-Ray Powder Diffraction

Figure 2:
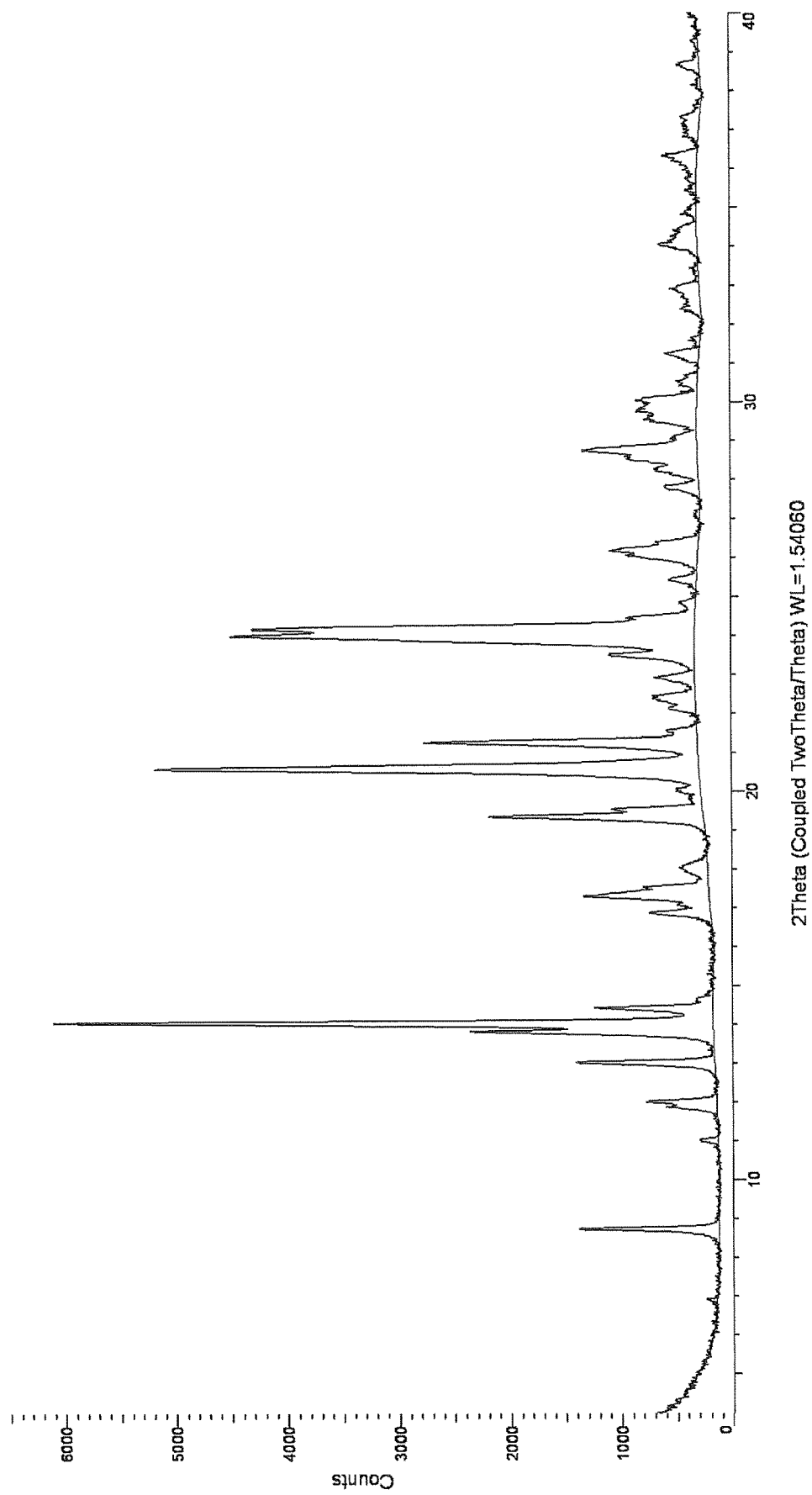
FIG. 2 is an X-ray powder diffractogram of another crystalline form ("Form B") of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

Crystals of crystalline Form B Compound 1 were prepared according to the method of Example 3. X-Ray powder diffraction (XRPD) analysis was carried out using a Bruker D2 Phaser powder diffractometer equipped with a LynxEye detector. The samples underwent minimum preparation but, if necessary they were lightly milled in a pestle and mortar before acquisition. The specimens were located at the centre of a silicon sample holder within a 5 mm pocket (ca. 5 to 10 mg). The samples were continuously spun during data collection and scanned using a step size of 0.02° two theta (2θ) between the range of 4° to 40° two theta and a step time of 34.5 seconds. Data were processed using Bruker Diffrac.Suite. The X-Ray Powder Diffractogram of the crystalline Form B of compound is shown in FIG. 2 and the 2θ diffraction angles and intensities associates with each peak are shown in the table below.

| Diffraction Angle (°) | Relative Intensity |
|---|---|
| 8.75 | 23 |
| 12.00 | 13 |
| 13.03 | 23 |
| 13.82 | 39 |
| 14.05 | 100 |
| 14.43 | 20 |
| 16.89 | 12 |
| 17.31 | 22 |
| 19.34 | 36 |
| 20.56 | 85 |
| 21.25 | 45 |
| 23.52 | 18 |
| 23.97 | 74 |
| 24.15 | 71 |
| 26.18 | 18 |
| 28.74 | 22 |
| 29.84 | 13 |

Example 4B—Differential Scanning Calorimetry (DSC)

Figure 3:
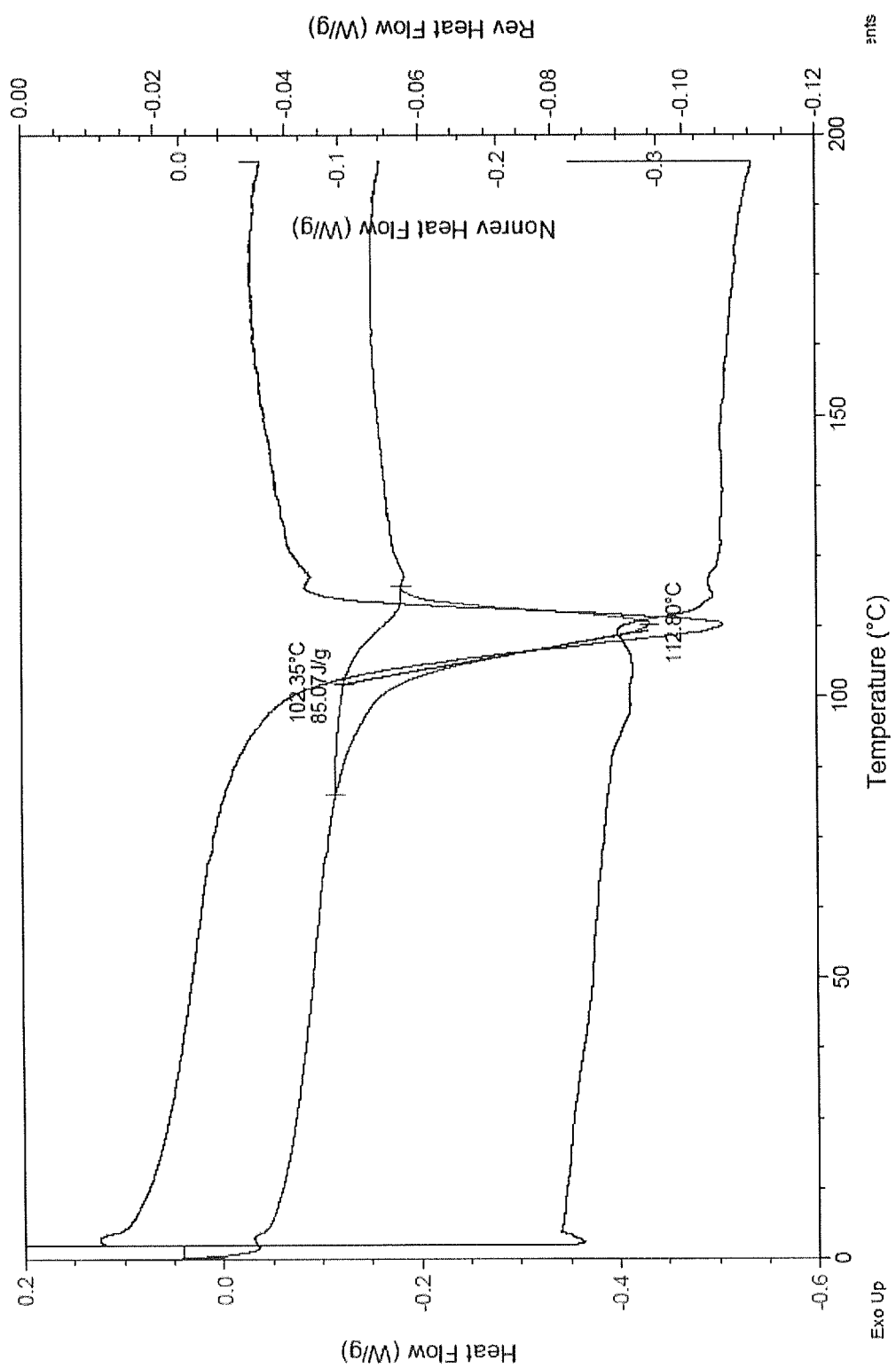
FIG. 3 is a Differential Scanning calorimetry (DSC) scan of crystalline form B of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

Crystals of crystalline Form B Compound 1 were prepared according to the method of Example 3. A Mettler Toledo DSC 821 instrument was used for the thermal analysis operating with STARe™ software. The analysis was conducted in 40 μL open aluminium pans, under nitrogen and sample sizes ranged from 1 to 10 mg. Typically, the analysis was carried out by over a temperature range of 20° to 250° at a temperature gradient of 10° C./minute. The DSC scan of the crystalline compound is shown in FIG. 3.

Example 4C—Thermogravimetric Analysis (TGA)

Figure 4:
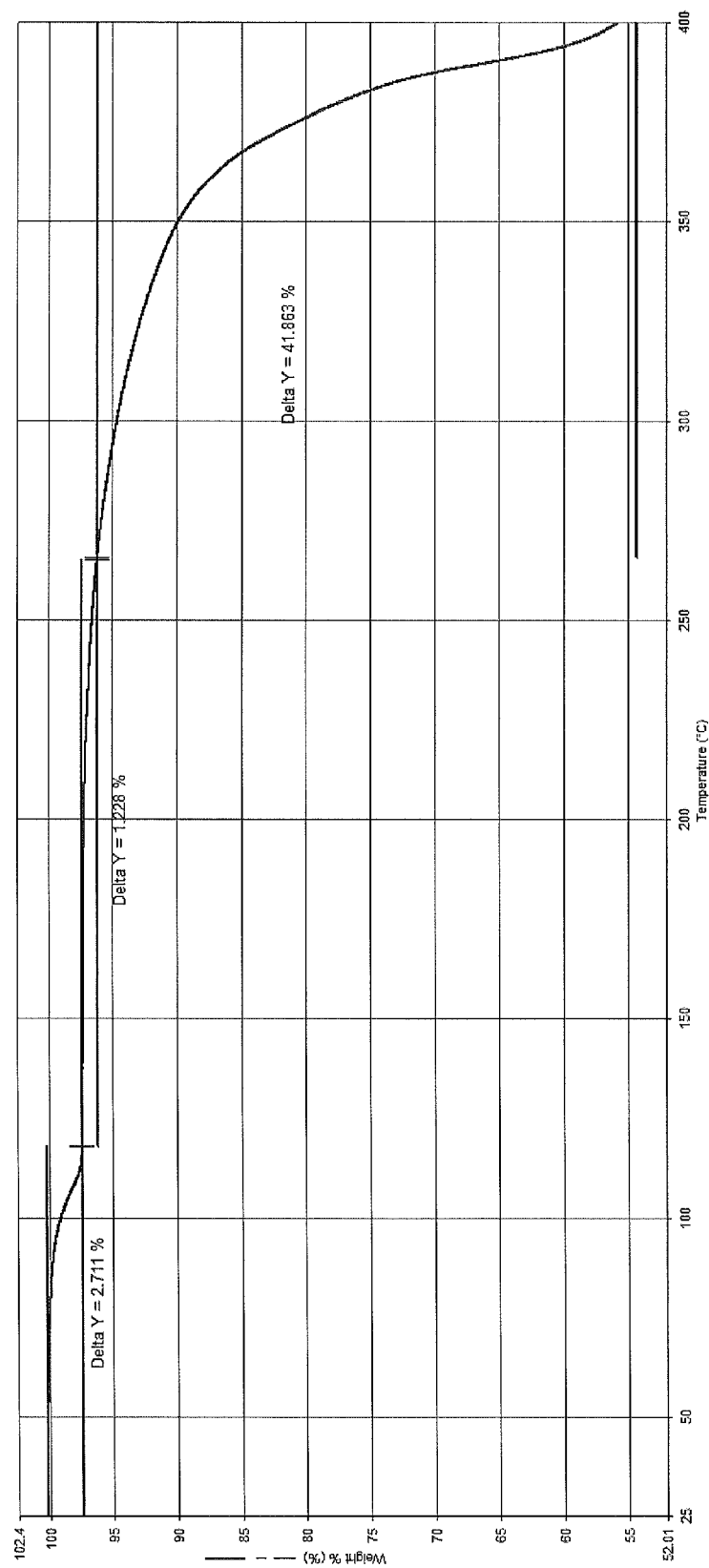
FIG. 4 is a weight loss profile obtained by thermogravimetric analysis of crystalline form B of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide.

Crystals of crystalline Form B Compound 1 were prepared according to the method of Example 3. Approximately 7 mg of sample was placed into a platinum HT TGA pan which had been cleaned using a butane blow torch and tared using the instrument's automated tare function. The samples were heated under a nitrogen atmosphere from 25 to 800° C. at a rate of 10° C./min. The weight loss profile of the crystalline compound is shown in FIG. 4.

Example 4D—Dynamic Vapour Sorption Analysis

Figure 5:
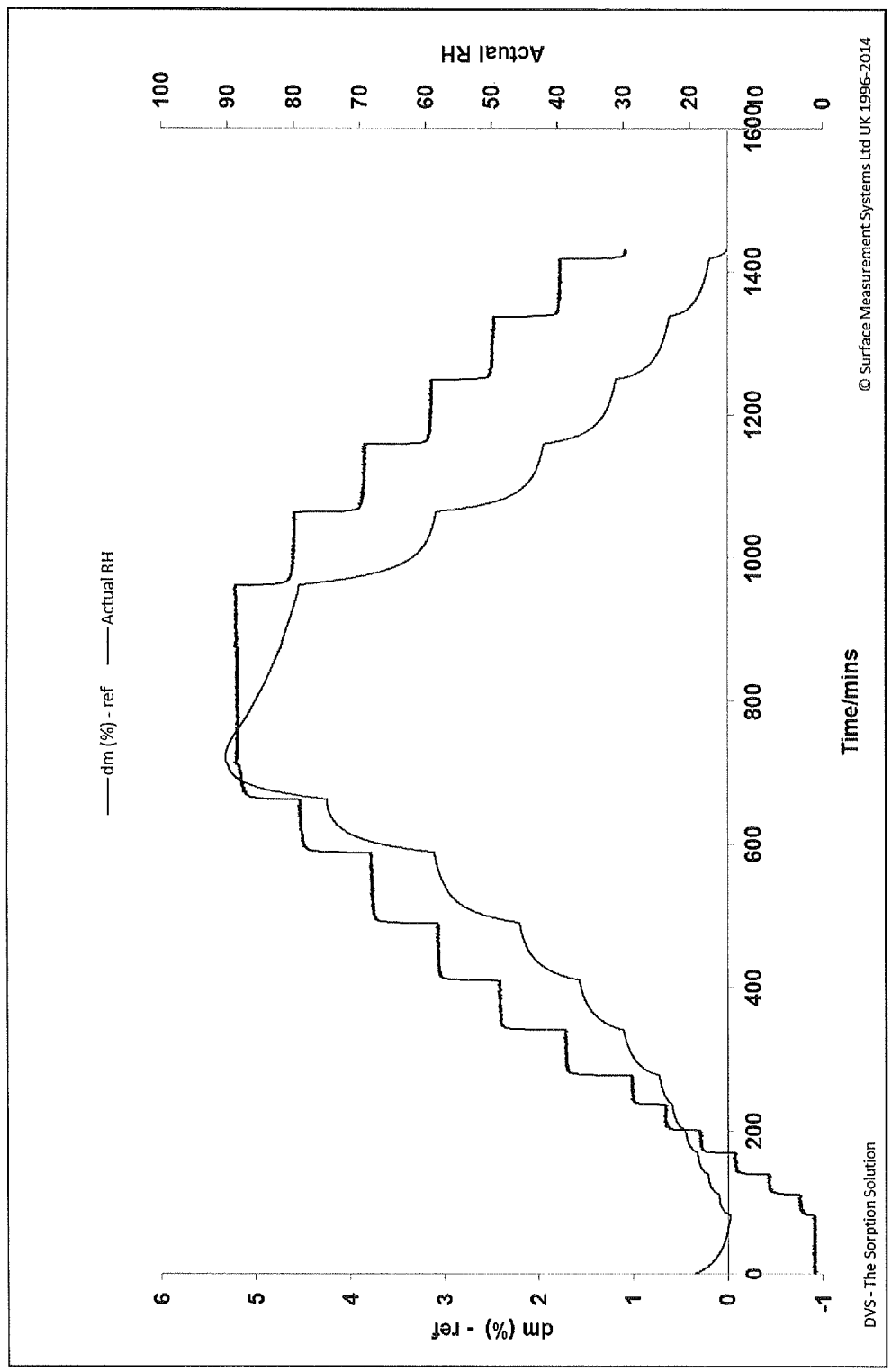
FIG. 5 is shows the weight profile of crystalline form B of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide at varying humidities obtained by dynamic vapour sorption analysis.

Crystals of crystalline Form B Compound 1 were prepared according to the method of Example 3. Approximately 20 mg of sample was weighed into an aluminium pan and loaded into an DVS Intrinsic instrument held at 25° C. The sample was allowed to equilibrate for three hours at 0% RH before ramping the humidity from 0-30% RH at 5% increments. This was followed with ramping at 10% increments up to 90% RH. A similar ramp profile was used for the desorption phase. At each step, a rate of change in mass per time unit (dt) of 0.002%/min was set as the equilibrium parameter. The vapour sorption/desorption profile of the compound is shown in FIG. 5.

Example 4E—Single Crystal X-Ray Diffraction Studies

The single crystal X-ray structure of the Form B of the compound of formula (1) was determined at 100K using a crystal obtained by slow evaporation from isopropyl acetate.
Data were collected on a Rigaku Oxford Diffraction Supernova Dual Source, Cu at Zero, Atlas CCD diffractometer equipped with an Oxford Cryosystems Cobra cooling device. The data were collected using Cu Kα. Structures were solved and refined using the Bruker AXS SHELXTL suite. Full details can be found in the Table below. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter. A reference diffractogram for the crystal structure was generated using Mercury (C. F. a. Macrae, "Mercury: visualization and analysis of crystal structures," J. Appl. Cryst., vol. 39, pp. 453-457, 2006).

Data Collection and Structure Refinement

| | |
|---|---|
| Diffractometer | SuperNova, Dual, Cu at zero, Atlas |
| Radiation source | SuperNova (Cu) X-ray Source, CuKα |
| Data collection method | scans |
| Theta range for data collection | 3.460 to 66.589° |
| Index ranges | $-14 \leq h \leq 15, -10 \leq k \leq 9, -14 \leq l \leq 15$ |
| Reflections collected | 24752 |
| Independent reflections | 4834 [R(int) = 0.0371] |
| Coverage of independent reflections | 97.4% |
| Absorption correction | Semi-empirical from equivalents |
| Max. and min. transmission | 1.00000 and 0.80872 |
| Structure solution technique | Direct Methods |
| Structure solution/refinement program | SHELXTL (Sheldrick, 2013) |
| Refinement technique | Full-matrix least-squares on F2 |

Crystal Data

| | |
|---|---|
| Crystallisation solvent | Isopropyl acetate |
| Crystallisation method | Slow evaporation |
| Empirical formula | $C_{29}H_{33}ClFN_5O_6$ |
| Formula weight | 602.05 |
| Temperature | 100(2) K |
| Wavelength | 1.54178 Å |
| Crystal size | 0.180 × 0.060 × 0.050 mm |
| Crystal habit | Colourless block |
| Crystal system | Monoclinic |
| Space Group | $P2_1$ |
| Unit cell dimensions | a = 12.6616(2) Å    a = 90° |
| | b = 9.0139(2) Å    b = 103.2380(10)° |
| | c = 13.1214(2) Å    g = 90° |
| Volume | 1457.76(5) Å$^3$ |

The crystals were found to be monoclinic, space group P21 with the final R1=[I>2s(I)]=2.93%.

The absolute stereochemistry of the compound has been determined using the diffraction data and has been confirmed to be as depicted in formula (1) herein with the Flack parameter=−0.004 (7).

In the asymmetric unit there is one molecule of the compound of formula (1) and one water molecule, both fully ordered, confirming that the crystalline Form B is a monohydrate of the compound of formula (1).

EXAMPLE 5

Solubility Determinations of Crystalline Form B of Compound (1) in Aqueous Solvents The solubilities of crystalline form B and the amorphous form of the compound of formula (1) were determined in purified water and buffers at the same concentration up to 24 h stir time at 18 to 23° C. The pH and temperatures of the solutions were monitored to confirm that pH drift did not occur towards the end of the experiment.

General Procedure

The samples of the compound of formula (1) (50 mg) were each suspended in purified water (2 mL) or the appropriate buffer and stirred at ambient temperature (18-23° C.) for 20 to 24 h. After this time the slurries were centrifuged, diluted if appropriate by HPLC sample diluent (acetonitrile/water, 1/1, v/v) and analysed by HPLC peak area. The measured values were compared against a relevant calibration curve for the compound of formula (1). The approximate solubilities were calculated and compensation factors were applied for the appropriate dilution factors and % w/w assays. The dilution factor ensured that the peak area values fell within the desired calibration curve ranges.

The plug of solid that remained in the centrifuge tube was dried in vacuum oven and analysed by XRPD. If the specimen exhibited any evidence of crystallinity other than the expected diffraction pattern for the crystalline form of compound (1) then further analysis by $^1$H NMR was performed to confirm chemical identity.

The preparations of the buffers used in the study are described below:

pH 1.2—Mix 50 mL of 0.2M potassium chloride solution with 85 mL of 0.2M hydrochloric acid solution.

pH 2—Mix 50 mL of 0.2M potassium chloride solution with 13 mL of 0.2M hydrochloric acid solution.

pH 3—Mix 100 mL of 0.1M potassium hydrogen phthalate with 44.6 mL of 0.1M hydrochloric acid solution.

pH 4—Mix 100 mL of 0.1M potassium hydrogen phthalate with 0.2 mL of 0.1M hydrochloric acid solution.

pH 5—Mix 100 mL of 0.1M potassium hydrogen phthalate with 45.2 mL of 0.1M sodium hydroxide solution.

pH 6—Mix 100 mL of 0.1M potassium dihydrogen orthophosphate with 11.2 mL of 0.1M sodium hydroxide solution.

pH 7—Mix 100 mL of 0.1M potassium dihydrogen orthophosphate with 58.2 mL of 0.1M sodium hydroxide solution.

pH 8—Mix 100 mL of 0.1M potassium dihydrogen orthophosphate with 93.4 mL of 0.1M sodium hydroxide solution.

Results

| Input | Chemical purity of input (% area) | Buffer | Equilibrium pH/ T ° C. measurements (t = 24 h) | Measured solubilities (mg/ml) | Descriptive term |
|---|---|---|---|---|---|
| Amorphous Form of the Compound of Formula (1) | 97.48 | Purified water | 7.73/20.6 | <0.1 mg/ml (0.0234 mg/ml) | Practically insoluble |
| | | pH 1.2 Buffer | 1.12/20.2 | ≥0.1 mg/ml (0.1249 mg/ml) | Very slightly soluble |
| | | pH 2 Buffer | 2.00/19.2 | <0.1 mg/ml (0.0226 mg/ml) | Practically insoluble |
| | | pH 3 Buffer | 3.07/20.2 | <0.1 mg/ml (0.0257 mg/ml) | Practically insoluble |
| | | pH 4 Buffer | 3.98/19.1 | <0.1 mg/ml (0.0418 mg/ml) | Practically insoluble |
| | | pH 5 Buffer | 4.99/19.4 | <0.1 mg/ml (0.0268 mg/ml) | Practically insoluble |
| | | pH 6 Buffer | 6.01/19.4 | <0.1 mg/ml (0.0149 mg/ml) | Practically insoluble |
| | | pH 7 Buffer | 6.97/21.0 | <0.1 mg/ml (0.0136 mg/ml) | Practically insoluble |
| | | pH 8 Buffer | 8.16/19.8 | <0.1 mg/ml (0.0138 mg/ml) | Practically insoluble |

Conclusions and Observations

Both the crystalline and amorphous forms of the compound of formula (1) were practically

| Input | Chemical purity of input (% area) | Buffer | Equilibrium pH/ T ° C. measurements (t = 24 h) | Measured solubilities (mg/ml) | Descriptive term |
|---|---|---|---|---|---|
| Crystalline Form B of the Compound of Formula (1) | 99.10 | Purified water | 7.88/22.1 | <0.1 mg/ml (0.0187 mg/ml) | Practically insoluble |
| | | pH 1.2 Buffer | 1.11/20.8 | <0.1 mg/ml (0.0154 mg/ml) | Practically insoluble |
| | | pH 2 Buffer | 2.01/20.4 | <0.1 mg/ml (0.0034 mg/ml) | Practically insoluble |
| | | pH 3 Buffer | 3.08/20.7 | <0.1 mg/ml (0.0045 mg/ml) | Practically insoluble |
| | | pH 4 Buffer | 4.00/20.4 | <0.1 mg/ml (0.0049 mg/ml) | Practically insoluble |
| | | pH 5 Buffer | 5.00/20.7 | <0.1 mg/ml (0.0031 mg/ml) | Practically insoluble |
| | | pH 6 Buffer | 6.02/20.5 | <0.1 mg/ml (0.0027 mg/ml) | Practically insoluble |
| | | pH 7 Buffer | 6.98/20.5 | <0.1 mg/ml (0.0017 mg/ml) | Practically insoluble |
| | | pH 8 Buffer | 8.02/20.2 | <0.1 mg/ml (0.0020 mg/ml) | Practically insoluble |
| | | Purified water | 7.71/20.4 | <0.1 mg/ml (0.0012 mg/ml) | Practically insoluble |
| | | pH 1.2 Buffer | 1.19/19.5 | <0.1 mg/ml (0.0164 mg/ml) | Practically insoluble | insoluble in buffers at pH 1.2 to 8.0 (ca <0.1 mg/ml).

Solubility Determinations of Crystalline Form B of Compound (1) in Non-Aqueous Solvents Procedure Form B of Compound (1), prepared as described in Example 3, was charged to the appropriate solvent (2 ml) at intervals of approximately 1 hour. The solutions were purposefully saturated and allowed to stir over 72 h at 18 to 23° C. After this time, the suspensions were centrifuged, their supernatants were sampled, diluted accordingly and the peak areas of the corresponding analytes were measured by HPLC and compared against those of the standard calibrants. The approximate solubilities were calculated and solubilities were physically checked on an anhydrous solvent free basis to confirm that the results were consistent.

Observations and Results

| | Ethanol (2 ml) | Glycerol (2 ml) | PEG 400 (2 ml) | Propylene glycol (2 ml) |
|---|---|---|---|---|
| First charge/ stir 1 h @ 18 to 23° C. | 198.74 mg | 200.30 mg | 198.96 mg | 200.91 mg |
| Second charge/ stir + 1 h @ 18 to 23° C. | 200.07 mg | — | 200.78 mg | 201.03 mg |
| Third charge/ stir + 1.5 h @ 18 to 23° C. | 200.94 mg | — | 200.27 mg | 201.17 mg |

-continued

| | Ethanol (2 ml) | Glycerol (2 ml) | PEG 400 (2 ml) | Propylene glycol (2 ml) |
|---|---|---|---|---|
| Fourth charge/ stir + 72 h @ 18 to 23° C. | 200.12 mg | — | — | 199.76 mg |
| Fifth charge/ stir + 2 h @ 18 to 23° C. | 200.34 mg | — | — | — |

The saturated solutions were centrifuged and 100 µl of the clarified supernatant was added to 250 ml volumetric (ethanol) or 100 ml volumetrics (remainder) and made to volume with sample diluent. The diluted samples were then analysed by HPLC peak area and the estimated maximum solubilities were calculated and are reported in the table below.

| Solvent | Estimated maximum solubilities (mg/ml), at 18 to 23° C. |
|---|---|
| Ethanol | 337 |
| Glycerol | 5 |
| PEG 400 | 229 |
| Propylene glycol | 289 |

To confirm the estimated solubilities were of the right order of magnitude solutions were prepared up to the estimated maximum measured concentrations and the mixtures were stirred overnight under the same conditions to confirm dissolution.

CONCLUSION

The compound of formula (1) has been shown to have a significantly greater solubility in ethanol, PEG 400 and propylene glycol than in water.

EXAMPLE 6

Liquid Formulations—I
Solvents
a. Propylene glycol—P4347 SIGMA-ALDRICH (meets USP testing specifications)
b. Ethanol—29221 SIGMA-ALDRICH (tested according to Ph.Eur.)
c. Super Refined™ PEG 400—Croda (JP, USP-NF, PhEur)
d. Combination of propylene glycol and ethanol, 75:25 (% w/w)
e. Combination of propylene glycol and ethanol, 85:15 (% w/w)

Protocol

The compound of formula (1) is incubated in each of the solvents at 500 mg/mL in glass vials (at 25° C. using an RS9000 heater block) and left under constant agitation. At T=1, 3, 7, 24 and 48 hours.

The resulting suspension is ultra-centrifuged (i.e. 500 to 1000 µl sample size) for 15 minutes at 13,000 rpm and visually inspected to confirm clarification. If satisfactory clarification is not achieved then the centrifuge procedure is repeated to sediment any remaining non-dissolved compound. The supernatant is sampled as relevant (e.g. 100 µl to 1000 µl), diluted as appropriate and analysed by HPLC-UV in order to establish the actual concentration.

EXAMPLE 7

Liquid Formulations—II
The following liquid formulations were prepared.
7-1. Compound of formula (1) dissolved in 5 g TPSG and 5 g propylene glycol.
7-2. Compound of formula (1) dissolved in 6 g TPSG and 6 g propylene glycol.
7-3. Compound of formula (1) dissolved in 2.5 g TPSG and 7.5 g propylene glycol.
7-4. Compound of formula (1) dissolved in TPGS (20% w/w), Ethanol (15% w/w) and propylene glycol (65% w/w)
7-5. Compound of formula (1) dissolved in propylene glycol (100% w/w)
7-6. Compound of formula (1) dissolved in TPGS (10% w/w), Ethanol (10% w/w) and propylene glycol (80% w/w)

The concentration of the compound of formula (1) in each formulation was 100 mg/mL.

Each formulation was subjected to dilution studies in simulated gastric fluid and simulated intestinal fluid by the methods described below. In the tests, concentrations of the compound of formula (1) were determined using the following HPLC-UV method.

LC Method Parameters
Column: Halo C18 150×4.6 mm; 2.7 µm
Inj. Volume: 5 µL
Detection: UV @ 221 nm
Mobile Phase A: Water/Acetonitrile/TFA (5/95/0.05 v/v/v)
Mobile Phase B: Water/Acetonitrile/TFA (95/5/0.5 v/v/v)

| Time (mins) | % A | % B |
|---|---|---|
| 0.0 | 100 | 0 |
| 2.0 | 100 | 0 |
| 24.0 | 60 | 40 |
| 28.0 | 50 | 50 |
| 33.0 | 0 | 100 |
| 36.0 | 0 | 100 |
| 36.1 | 100 | 0 |
| 40.0 | 100 | 0 |

Flow rate: 1.0 mL/min
Column Temperature: 40° C.
Run Time: 40 minutes
Integration Time: 36 minutes
Wash vial: Sample diluent
Dilution Studies Each formulation was charged into 50 mL of FaSSGF (prepared according to the method described in http://biorelevant.com/fassif-fessif-fassgf/how-to-make/) and sampled at three time points (T=5 minutes, 15 minutes and 30 minutes) wtihdrawing at least 2 mL per sample.

The mixture was then further diluted with 44 mL of fasted state simulated intestinal fluid FaSSIF (prepared according to the method described in http://biorelevant.com/fassif-fessif-fassgf/how-to-make/) and sampled at eight time points (T=5 minutes, 15 minutes, 30 minutes, 45 minutes, 1 hour, 3 hours, 5 hours, and 7 hours). Samples were analysed for the compound of formula (1) concentration by HPLC-UV.

For Formulations 7-1 and 7-2, around 65% of the compound of formula (1) remained solubilised after 30 minutes of dilution in FaSSGF. Upon the next dilution step, when moving into FaSSIF, the amount of the compound solubilised remained around 50% up to 3 hours and then gradually decreased. Extrapolating from the results of this dilution study to a "human dilution scenario", it was expected that >60% of a 1000 mg dose of the compound of formula (1) would dissolve in Formulation 7-1 or Formulation 7-2 (i.e. around 600 mg) and would remain in solution when entering the stomach.

For Formulation 7-3, after 30 minutes of dilution in FaSSGF around 33% of the drug remained still solubilised. Upon the next dilution step, when moving into FaSSIF, the amount of the drug solubilised remained at around 27% up to 3 hours and then gradually decreased. Extrapolating from the results of this dilution study to a "human dilution scenario", it was expected that >30% of a 1000 mg dose would dissolve in Formulation 7-3 (i.e. around 300 mg) and would remain in solution when entering the stomach.

For Formulation 7-4, after 30 minutes of dilution in FaSSGF around 30% of the drug remained still solubilised. Upon the next dilution step, when moving into FaSSIF, the amount of the drug solubilised remained around 24% up to 3 hours and then gradually decreased. Extrapolating from the results of this dilution study to a "human dilution scenario", it was expected that >30% of a 1000 mg dose would dissolve in Formulation 7-4 (i.e. around 300 mg) and would remain in solution when entering the stomach.

For Formulation 7-5, after 30 minutes of dilution in FaSSGF around 2% of the drug remained still solubilised. Upon the next dilution step, when moving into FaSSIF, the amount of the drug solubilised remained around 2%.

For Formulation 7-6, after 30 minutes of dilution in FaSSGF around 17% of the drug remained still solubilised. Upon the next dilution step, when moving into FaSSIF, the amount of the drug solubilised remained around 11%.

Formulation 7-6 was found to be particularly advantageous. The placebo version (i.e. vehicle alone and no compound of formula (1) present) of this formulation initially formed a clear liquid containing some sediment but the sediment was redissolved by heating to 50° C. and the liquid remained clear with no sediment or cloudiness after 24 and 96 hours. The active version of formulation 7-6 containing 100 mg/ml of the compound of formula (1) formed a clear solution that remained as a clear liquid with no precipitate or cloudy solution after 24 and 192 hours at room temperature.

EXAMPLE 8

Biological Activity

Example 8A—ERK2 In Vitro Inhibition Assay

The inhibitory activity of the compound of the invention was determined using the protocol set out below.

Activity of ERK2 enzyme (Life Technologies) was determined using a time-resolved fluorescence format measuring the phosphorylation of a truncated version of Activating transcription factor 2 labelled with green fluorescent protein (ATF2-GFP) (Life Technologies). Assay reactions containing 50 mM Tris pH 7.5, 10 mM $MgCl_2$, 1 mM EGTA, 0.01% Triton X-100, 1 mM DTT, 2.5% DMSO, 0.4 µM ATF2-GFP, 20 µM ATP and 0.25 nM ERK2 were set up in the presence of compound and allowed to proceed for 30 min at room temperature. Reactions were then stopped using TR-FRET dilution buffer (Life Technologies), 25 mM EDTA and 2 nM Tb-Anti-pATF2 (Thr71) (Life Technologies). After a further incubation period of at least 30 minutes, fluorescence was read on a Pherastar reader (Lanthascreen optic module; excitation 340 nm, emission 520 nm (channel A), 495 nm (channel B)). The ratio between A and B counts was used to calculate signal. $IC_{50}$ values were calculated using a sigmoidal dose response equation (Prism GraphPad software, La Jolla, Calif., USA).

In the assays using ERK2, the compound of formula (1) has an $IC_{50}$ value of 0.0027 µM.

Example 8B—Anti-Proliferative Activity

The anti-proliferative activities of the compound of the invention was determined by measuring the ability of the compound of formula (1) to inhibit growth in the Human melanoma cell line A375.

Cell proliferation was determined by measuring the conversion of rezasurin (Alamar Blue) to resorufin in reponse to mitochondrial activity (Nociari, M. M, Shalev, A., Benias, P., Russo, C. *Journal of Immunological Methods* 1998, 213, 157-167). A375 cells (American Type Culture Collection, Teddington, UK) were grown in Dulbecco's Modified Eagle Medium+10% FBS. Each well of a black 96-well flat-bottomed plate was seeded with $2 \times 10^3$ cells in 200 µl of complete culture medium one day before the compound treatment. Cells were incubated with compound in 0.1% (v/v) dimethyl sulfoxide (DMSO) for 4 days before addition of 20 µl Alamar blue. After a further 6 h incubation at 37° C. the plate was read on a Spectramax Gemini reader (Molecular Devices; excitation 535 nm, emission 590 nm). $GI_{50}$ values were calculated using a sigmoidal dose response equation (Prism GraphPad software, La Jolla, Calif., USA).

In the assays using A375 cells, the compound of formula (1) has a $GI_{50}$ value of 0.0034 µM.

Combination Protocol for Cell Proliferation

The effect of a compound of formula (1) (Compound I) in combination with an anticancer agent (Compound II) can be assessed using the following technique. Human cancer cell lines (e.g. A375) were seeded onto 96-well tissue culture plates at a concentration of $2 \times 10^3$-$4 \times 10^3$ cells/well. Cells were allowed to recover for 16-24 hours prior to addition of compound(s) or DMSO control (0.1-0.5% DMSO). Cells were incubated with compound in 0.1%-0.5% (v/v) dimethyl sulfoxide (DMSO) for 72-96 hours, before addition of 20 µl Alamar blue. After a further 6 h incubation at 37° C. the plate was read on a Spectramax Gemini reader (Molecular Devices; excitation 535 nm, emission 590 nm). $GI_{50}$ values were calculated using a sigmoidal dose response equation (Prism GraphPad software, La Jolla, Calif., USA). The $GI_{50}$ for Compound II in the presence of varying doses of Compound I was determined. Synergy was determined when the $GI_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $GI_{50}$ to shift upwards, i.e. those where the response to the two compounds was less than the sum of the effect of the two compounds.

EXAMPLE 9

Pharmaceutical Formulations
(i) Tablet Formulation

A tablet composition containing the compound of formula (1) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg (e.g 100 mg) of the compound of formula (1) with an equivalent amount of lactose (e.g. 100 mg) and filling the resulting mixture into standard opaque hard gelatin capsules. An appropriate disintegrant and/or glidant can be included in appropriate amounts as required.

(iii) Injectable Formulation I

A parenteral composition for administration by injection can be prepared by dissolving a compound of formula (1) (e.g. in a salt form) in water containing 10% propylene glycol to give a concentration of active compound of 1.5% by weight. The solution is then sterilised by filtration, filled into an ampoule and sealed. Optionally the solution can be made isotonic before sterilisation.

(iv) Injectable Formulation II

A parenteral composition for injection is prepared by dissolving in water a compound of formula (1) (e.g. in salt form) (2 mg/ml) and mannitol (50 mg/ml), sterile filtering the solution and filling into sealable 1 ml vials or ampoules or pre-filled syringe.

(v) Injectable Formulation III

A formulation for i.v. delivery by injection or infusion can be prepared by dissolving the compound of formula (1) (e.g. in a salt form) in water at 20 mg/ml and optionally then adjusted for isotonicity. The vial is then sealed and sterilised by autoclaving. Alternatively it may be filled into an ampoule or vial or pre-filled syringe, sterilised by filtration and sealed.

(vi) Injectable Formulation IV

A formulation for i.v. delivery by injection or infusion can be prepared by dissolving the compound of formula (1) (e.g. in a salt form) in water containing a buffer (e.g. 0.2 M acetate pH 4.6) at 20 mg/ml. The vial is then sealed and sterilised by autoclaving. Alternatively a pre-filled syringe is then sealed and sterilised by autoclaving or sterilized by filtration and sealed.

(vii) Subcutaneous or Intramuscular Injection Formulation

A composition for sub-cutaneous (or intramuscular) administration is prepared by mixing a compound of formula (1) with pharmaceutical grade corn oil to give a concentration of 5-50 mg/ml (e.g. 5 mg/ml). The composition is sterilised and filled into a suitable container.

(viii) Lyophilised Formulation

Aliquots of formulated compound of formula (1) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (1) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving the compound of formula (1) in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with the compound of formula (1). The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:

1. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, having the formula (1):

or a tautomeric form thereof, in a substantially crystalline form.

2. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 55% crystalline.

3. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 having an X-ray powder diffraction pattern characterised by the presence of major peaks at the diffraction angles 14.0° and/or 20.6° and/or 24.0° and/or 24.2° (±0.2°).

4. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-

2-hydroxyethyl]propanamide according to claim 1 having an X-ray power diffraction pattern characterised by the presence of major peaks at the diffraction angles and interplanar spacing set forth in Table A:

TABLE A

| Diffraction Angle (°) | Relative Intensity |
|---|---|
| 14.0 | 100 |
| 20.6 | 85 |
| 24.0 | 74 |
| 24.2 | 71. |

5. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 4 wherein the X-ray powder diffraction pattern is further characterised by the presence of one or more additional peaks at the diffraction angles and interplanar spacings set forth in Table B.

TABLE B

| Diffraction Angle (°) | Relative Intensity |
|---|---|
| 8.8 | 23 |
| 13.0 | 23 |
| 13.8 | 39 |
| 14.4 | 20 |
| 17.3 | 22 |
| 19.3 | 36 |
| 21.3 | 45 |
| 28.7 | 22. |

6. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which exhibits peaks at substantially the same diffraction angles as those of the X-ray powder diffraction pattern shown in FIG. 2.

7. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 having an X-ray powder diffraction pattern substantially as shown in FIG. 2.

8. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which exhibits an endothermic event having an onset temperature between 100° C. to 110° C. when subjected to differential scanning calorimetry.

9. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which exhibits an endothermic event having a peak between 110° C. and 125° C. when subjected to differential scanning calorimetry.

10. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which exhibits a weight loss between 85° C. and 130° C. when subjected to thermogravimetric analysis.

11. A process for making a substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1; which method comprises:

(i) forming an aqueous suspension of an acid addition salt of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide and stirring the suspension at a temperature of between 25° C. and 75° C. for a period of time sufficient to allow disproportionation of the acid addition salt and formation of the crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide to occur, and thereafter isolating the crystalline form; or (ii) forming an aqueous suspension of an amorphous form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, wherein the aqueous suspension is unbuffered or is buffered to a pH of from 1.75 to 7.25, and stirring the aqueous suspension at a temperature of between 25° C. and 55° C. for a period of time sufficient to allow conversion of the amorphous form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide to the crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide to occur, and thereafter isolating the crystalline form.

12. A process for making (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide, which process comprises:

a) reacting a compound of formula (5):

(5)

(5)

with a compound of formula (6)

(2)

-continued

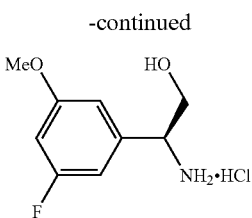

to give a compound of formula (2):

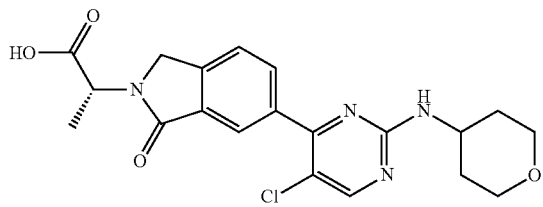

and:
b) reacting the compound of formula (2) with a compound of formula (3):

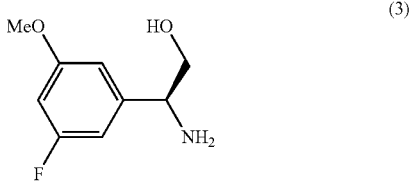 [SMILES: COc1cc(F)cc([C@H](N)CO)c1]

to give the compound of formula (1):

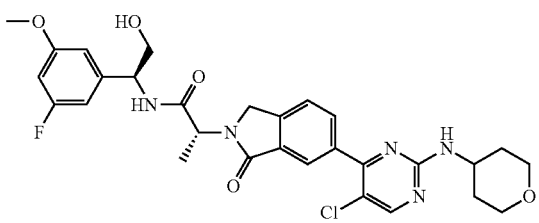

and thereafter optionally forming a salt or crystalline form thereof.

13. A pharmaceutical composition comprising (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide and a vehicle selected from:
   a $C_{2-4}$ alcohol;
   a polyether compound;
   mono-esters of $C_8$ to $C_{18}$ long chain fatty acids with glycerol or propylene glycol;
   di- or tri-glycerides of $C_8$ to $C_{10}$ long chain fatty acids; and mixtures thereof; and optionally a non-ionic surfactant.

14. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide in the form of particles having a mass median diameter of between 1 μm and 100 μm.

15. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 8 which exhibits an endothermic event having an onset temperature of 101° C. to 108° C. when subjected to differential scanning calorimetry.

16. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 9 which exhibits an endothermic event having a peak between 111° C. and 113° C. when subjected to differential scanning calorimetry.

17. A substantially crystalline form of (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 10 which exhibits a weight loss at 90-120° C. when subjected to thermogravimetric analysis.

18. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 60% crystalline.

19. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 70% crystalline.

20. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 80% crystalline.

21. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 90% crystalline.

22. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 95% crystalline.

23. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 98% crystalline.

24. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 99% crystalline.

25. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 99.5% crystalline.

26. (2R)-2-(6-{5-chloro-2-[(oxan-4-yl)amino]pyrimidin-4-yl}-1-oxo-2,3-dihydro-1H-isoindol-2-yl)-N-[(1S)-1-(3-fluoro-5-methoxyphenyl)-2-hydroxyethyl]propanamide according to claim 1 which is at least 99.9% crystalline.

* * * * *

UNITED STATES PATENT AND TRADEMARK OFFICE
CERTIFICATE OF CORRECTION

PATENT NO. : 11,142,518 B2
APPLICATION NO. : 16/604002
DATED : October 12, 2021
INVENTOR(S) : Reader et al.

Page 1 of 1

It is certified that error appears in the above-identified patent and that said Letters Patent is hereby corrected as shown below:

In the Claims

Column 75, Line 2: Claim 4, Delete "X-ray power" and insert -- X-ray powder --

Column 76, Lines 55-65, through Column 77, Lines 1-9: Claim 12,
Delete "with a compound of formula (6)

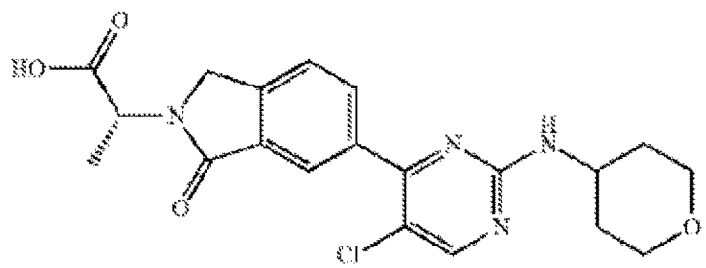

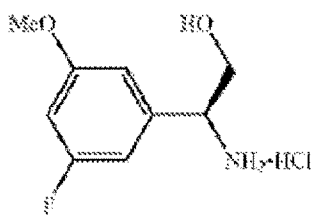

"

And insert -- with a compound of formula (6)

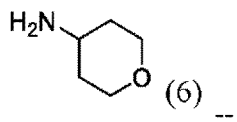

--

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*